US011608352B2

(12) United States Patent
Kerr et al.

(10) Patent No.: US 11,608,352 B2
(45) Date of Patent: Mar. 21, 2023

(54) GLYCOLIPOPEPTIDE BIOSURFACTANTS

(71) Applicant: Croda International Plc, Goole (GB)

(72) Inventors: Russell Greig Kerr, Charlottetown (CA); Bradley Arnold Haltli, New Haven (CA); Douglas Hubert Marchbank, Stratford (CA); Fabrice Berruè, Halifax (CA)

(73) Assignee: CRODA INTERNATIONAL PLC, Goole (GB)

( * ) Notice: Subject to any disclaimer, the term of this patent is extended or adjusted under 35 U.S.C. 154(b) by 122 days.

(21) Appl. No.: 16/817,193

(22) Filed: Mar. 12, 2020

(65) Prior Publication Data

US 2020/0207799 A1 Jul. 2, 2020

Related U.S. Application Data

(62) Division of application No. 16/090,888, filed as application No. PCT/EP2017/058296 on Apr. 6, 2017, now abandoned.

(30) Foreign Application Priority Data

Apr. 6, 2016 (GB) ..................................... 1605875

(51) Int. Cl.

| | |
|---|---|
| ***C12P 19/40*** | (2006.01) |
| ***C07H 15/04*** | (2006.01) |
| ***C07H 1/08*** | (2006.01) |
| ***C12P 19/44*** | (2006.01) |
| ***C11D 1/66*** | (2006.01) |
| ***C12N 15/52*** | (2006.01) |
| ***C02F 3/34*** | (2023.01) |
| ***C11D 1/00*** | (2006.01) |
| ***C11D 3/38*** | (2006.01) |
| ***C12N 1/20*** | (2006.01) |
| *C11D 1/10* | (2006.01) |
| *C12R 1/01* | (2006.01) |

(52) U.S. Cl.

CPC ............... *C07H 15/04* (2013.01); *C02F 3/34* (2013.01); *C07H 1/08* (2013.01); *C11D 1/008* (2013.01); *C11D 1/662* (2013.01); *C11D 3/381* (2013.01); *C12N 1/205* (2021.05); *C12N 15/52* (2013.01); *C12P 19/44* (2013.01); *C11D 1/10* (2013.01); *C12R 2001/01* (2021.05)

(58) Field of Classification Search

CPC .......... C12N 1/36; C12N 9/10; C12N 9/1051; C12N 9/16; C12P 19/44; C12P 7/64

USPC ............................... 435/74, 274, 174, 252.3

See application file for complete search history.

(56) References Cited

U.S. PATENT DOCUMENTS

| | | | |
|---|---|---|---|
| 2008/0274959 A1 | 11/2008 | Haltli et al. |
| 2013/0085067 A1 | 4/2013 | Schofield et al. |
| 2013/0331466 A1 | 12/2013 | Gross et al. |

OTHER PUBLICATIONS

Devos et al., (Proteins: Structure, Function and Genetics, 2000, vol. 41: 98-107.*

Whisstock et al., (Quarterly Reviews of Biophysics 2003, vol. 36 (3): 307-340.*

Witkowski et al., (Biochemistry 38:11643-11650, 1999.*

Kisselev L., (Structure, 2002, vol. 10: 8-9.*

Abdel-Mawgoud et al., "Rhamnolipids: Detection, Analysis, Biosynthesis, Genetic Regulation, and Bioengineering of Production", Biosurfactants, Microbiology 20, pp. 13-55.

Altschul et al., "Gapped BLAST and PSI-BLAST: A New Generation of Protein Database Search Programs", Nucleic Acids Res., 1997, vol. 25, No. 17, pp. 3389-3402.

Aziz et al., "The RAST Server: Rapid Annotations using Subsystems Technology", BMC Genomics 9, 2008, pp. 1-15.

Bachman et al., "Methods for In Silico Prediction of Microbial Polyketide and Nonribosomal Peptide Biosynthetic Pathways from DNA Sequence Data", Methods in Enzymology, 2009, vol. 458, pp. 181-217.

Baltz, R., "MbtH Homology Codes to Identify Gifted Microbes for Genome Mining", J. Ind. Microbiol Biotechnol, 2014, vol. 41, pp. 357-369.

Breton et al., "Structures and Mechanisms of Glycosyltransferases" Glycobiology, 2006, vol. 16, No. 2, pp. 29R-37R.

Brettin et al., "RASTtk: A Modular and Extensible Implementation of the RAST algorithm for Building Custom Annotation Pipelines and Annotating Batches of Genomes", Scientific Reports, 5:8365, pp. 1-6.

Cai et al., "Efficient synthesis of a 6-deoxytalose tetrasaccharide related to the antigenic O-polysaccharide produced by aggregatibacter actinomycetemcomitans serotype c.", Carbohydr. Res. 2010, 345, 1230 (Spec., p. 16).

Chaisson et al., "Taxon Ordering in Phylogenetics Trees by Means of Evolutionary Algorithms", BMC Bioformatics, 2012, 13:238, pp. 1-17.

Chin et al., "Nonhybrid, Finished Microbial Genome Assemblies From Long-Read SMRT Sequencing Date", Nature Methods, Jun. 2013, vol. 10, No. 6, pp. 563-569.

(Continued)

*Primary Examiner* — Robert B Mondesi
*Assistant Examiner* — Mohammad Y Meah
(74) *Attorney, Agent, or Firm* — RatnerPrestia

(57) ABSTRACT

Surfactants based on a newly discovered class of compounds include a hydrophobic lipid oligomer covalently linked to a peptide or peptide-like chain and a carbohydrate moiety, and a serine-leucinol dipeptide linked to the lipid oligomer. Such surfactants can be used to create an oil-in-water or water-in-oil emulsion by mixing together a polar component; a non-polar component; and the surfactant. Biosurfactants of the newly discovered class can be made by isolating and culturing a microorganism which produces the biosurfactant, and then isolating the biosurfactant from the culture. A microorganism can be engineered to produce biosurfactant of this newly discovered class by expressing a set of heterologous genes involved in the biosynthesis of the biosurfactant in the microorganism.

23 Claims, 23 Drawing Sheets

Specification includes a Sequence Listing.

(56) References Cited

OTHER PUBLICATIONS

Coin et al., "Solid-phase peptide synthesis: from standard procedures to the synthesis of difficult sequences" Nat. Protoc. 2007, 2, 3247 (Spec, p. 22).
Déziel et al., "rhlA is Required for the Production of a Novel Biosurfactant Promoting Swarming Motility in Pseudomonas Aeruginas: 3-(3-Hydroxyalkanoyloxy) Alkanoic Acids (HAAs), the Precursors of Rhamnolipids", Microbiology (2003), 149, pp. 2005-2013.
Du et al., "PKS and NRPS Release Mechanisms", Nat. Prod. Rep., 2010, vol. 27, pp. 255-278.
Dubeau et al.,"Burkholderia Thailandensis Harbors Two Identical rhl Gene Clusters Responsible for the Biosynthesis of Rhamnolipids", BMC Microbiology, 2009, 9:263, pp. 1-12.
Franzetti et al., "Environmental Fate, Toxicity, Characteristics and Potential Applications of Novel Bioemulsifiers Produced by Variovorax Paradoxus 7bCTS", Bioresource Technology 108, (2012), pp. 245-251.
Gampe et al., "Modular Synthesis of Diphospholipid Oligosaccharide Fragments of the Bacterial Cell Wall and their use to Study the Mechanism of Moenomycin and other Antibiotics", Tetrahedron, Dec. 23, 2011 67(51), pp. 9771-9778.
Graupner et al., "Imaging Mass Spectrometry and Genome Mining Reveal Highly Anti fungal Virulence Factor of Mushroom Soft Rot Pathogen", Angew. Chem. Int. Ed., 2012, vol. 51, pp. 13173-13177.
Grunewald et al., "Chemoenzymatic and Template-Directed Synthesis of Bioactive Macrocyclic Peptides", Microbiology and Molecular Biology Reviews, Mar. 2006, pp. 121-146.
Han et al., "Genome of the Root-Associated Plant Growth-Promoting Bacterium Variovorax Paradoxus Strain EPS", Genome Announcements, Sep./Oct. 2013, vol. 1, Issue 5, 2 pages.
Hansen et al., "The Loading Module of Mycologist: An Adenylation Domain with Fatty Acid Selectivity", J. Am. Chem. Soc., 2007, 129, pp. 6366-6367.
Herbst et al., "Structural Basis of the Interaction of MbtH-like Proteins, Putative Regulators of Nonribosomal Peptide Biosynthesis, with Adenylating Enzymes", Journal of Biological Chemistry, Jan. 18, 2013, vol. 228, No. 3, pp. 1991-2003.
International Search Report and Written Opinion for International Application No. PCT/EP2017/058296, dated Oct. 25, 2017, 17 pages.
Irwin et al., "Molecular Cloning" A Laboratory Manual, Third Edition, 2001, 3 pages.
Konz et al., "How do Peptide Synthetases generate Structural Diversity" Chemistry and Biology, Feb. 1999, 6, pp. R39-R48.
Kopp et al., "Harnessing the Chemical Activation Inherent to Carrier Protein-bound Thioesters for the Characterization of Lipopeptide Fatty Acid Tailoring Enzymes", J. Am. Chem. Soc., 2008, 130, pp. 2656-2666.
Kraas et al., Functional Dissection of the Surfactin Synthetase Initiation Module Reveals Insights into the Mechanism of Lipoinitiation, Chemistry and Biology 17, Aug. 27, 2010, pp. 872-880.
Maddocks et al., "Structure and Function of the LysR-type Transcriptional Regulator (LTTR) Family Proteins", Microbiology (2008), 154, pp. 3609-3623.
Marchler-Bauer et al., "CD-Search: Protein Domain Annotations on the Fly", Nucleic Acids Research, vol. 32, Web Server Issue, pp. W327-W331.
May et al., "The dhb Operon of Bacillus Subtilis Encodes the Biosynthetic Template for the Catecholic Siderophore 2,3Dihydroxybenzoate-Glycine-Threonine Trimeric Ester Bacillibactin", The Journal of Biological Chemistry, 2001, vol. 278, No. 10, Issue of Mar. 9, pp. 7209-7217.
Miao et al., "Rhamnolipids as Platform Molecules for Production of Potential Antizoospore Agrochemicals", Journal of Agricultural and Food Chemistry, 2015, vol. 63, pp. 3367-3376.
Mootz et al., "Tyrocidine Biosynthesis Operon of Bacillus Brevis: Complete Nucleotide Sequence and Biochemical Characterization of Functional Internal Adenylation Domains", Journal of Bacteriology, Nov. 1997, vol. 179, No. 21, pp. 6843-6850.
Myers et al., "A Whole-Genome Assembly of *Drosophila*", Science, Mar. 24, 2000, vol. 287, pp. 2196-2204.
Needleman et al., "A General Method Applicable to the Search of Similarities in the Amino Acid Sequence of Two Proteins", J. Mol. Biol. 1970, vol. 48, pp. 443-453.
Nguyen et al., "Characterization and Emulsification Properties of Rhamnolipid and Sophorolipid Biosurfactant and their Applications", Int. J. Mol. Sci., 2011, 12, pp. 1232-1244.
Overbeek et al., "The SEED and the Rapid Annotation of Microbial Genomes using Subsystems Technology (RAST)", Nucleic Acids Research, 2014, vol. 42, pp. D206-D214.
Pandey et al., "Efficient Total Synthesis of (-)(3S,6R)-3,6-Dihydorxy-10-methylundecanoic Acid", Eur. J. Org. Chem, 2007, pp. 369-373.
Rahim et al., "Involvement of the rml Locus in Core Oligosaccharide and O Polysaccharide Assembly in Pseudomonas Aeruginasa", Microbiology (2000), 146, pp. 2803-2814.
Reis et al., "Gene Regulation of Rhamnolipid Production in Pseudomonas Aeruginosa—A Review", Bioresource Technology, 102, (2011), pp. 6377-6384.
Rice et al., "Emboss: The European Molecular Biology Open Software Suite", TIG, 2000, vol. 16. No. 6, pp. 276-277.
Santos et al., "Biosurfactants: Multifunctional Biomolecules of the 21st Century", International Journal of Molecular Sciences, (2016), 17-31 pages.
Schneekloth et al., "Neurotrophic Peptide Aldehydes: Solid Phase Synthesis of Fellutamide B and a Simplified Analog", Bioorg. Med. Chem. Lett., Jul. 15, 2006, 16(14), pp. 3855-3858.
Scott, P.J.H., "Linker Strategies in Solid-Phase Synthesis", John Wiley & Sons Ltd: Chichester, U.K., 2009; pp. 50-51 (Spec, p. 22).
Stachellhaus et al., "The Specialty-Conferring Code of Adenylation Domains in Nonribosomal Peptide Synthetases", Chemistry 7 Biology, Aug. 1999, 6, pp. 493-505.
Takahashi et al., "The anomeric effect revisited. A possible role of the CH/n hydrogen bond", Carbohydr. Res. 2007, 342, pp. 1202-1209.
Toribio et al., "Rhamnolipids: Production in Bacteria other than Pseudomonas Aeruginosa", Eur. J. Lipid Sci. Technol., 2010, 112, pp. 1082-1087.
Valeur et al., "Amide bond formation: beyond the myth of coupling reagents", Chem. Soc. Rev. 2009, 38, pp. 606-631.
Wittman et al., "Role of DptE and DptF in the Lipidation Reaction of Daptomycin", FEBS Journal, 275, (2008), pp. 5343-5354.
Wu et al., "Programmable One-pot Glycosylation", Top. Curr. Chem. 2011, 301, pp. 223-252.
Ziemert et al., "The Natural Product Domain Seeker NaPDoS: A Phylogeny Based Bioinformatic Tool to Classify Secondary Metabolite Gene Diversity", PLoS One, Mar. 2012, vol. 7, Issue 3, 9 pages.
Clayden et al., Organic Chemistry, front cover of book, 1st edition, 2000, 1 page.

* cited by examiner

SEQ ID NO 1
LENGTH: 12721
TYPE: DNA
ORGANISM: *Variovorax paradoxus*

SEQUENCE: 1 gtcgtgtctccttcttttcgtggggtgttccaacgggccgactgggaggtcggctgaaaaccgctcgccagtgtgcg
tgccgcaaggtttgccttcaataaaataatcaagctaagtaatatgaatggcatgcatatcgactcggtcgacctca
atctgctgcgcctgttcgatgcggtctaccgcgagcgcagcgtgagccgcgccgcggagtcgctgggcctcacgcag
cctgcggcaagccatgggctgggacggctgcggctgcttttgaaagacgcgctcttcacgcgtgcccccggcggcgt
ggcgcccacgccgcgcgccgaccggctcgcggtggcggtgcaggcggcgctcggcacgatcgaagcggcgctgcacg
agcccgatcgcttcgagccccaggtgtcgcgcaagagctttcgtattcacatgagcgacatcggcgaggggcgcttc
ctgcccgcgctgatggcgcggctcggcgagctggcgcccggcgtgcggctggagaccctgccgctcttgcctgcgga
ggttgcgcccgcactcgacagcggccgcatcgatttcgccttcggctttctctcgaccgtgcgcgacacgcagcgca
cgcatcttctgaaagaccgctacatcgtgctgctgcgcaagggccatccctttgtgaagcgccggcgcaagggcag
gcgctgctcgaggcgctgcaggagctcgactacgtggcggtgcgcacgcacgccgacacgctgcgcatcttgcagtt
gctcaacctcgaagaccgcctgcgcctcacgaccgagcacttcatggtgctaccggccatcgtgcgcgccaccgatc
tcgcggtggtgatgccgcgcaacatcgcgcgagggtttgcggaggagggcggctacgcgatcgtcgagccgccgttt
ccgctgcgcgatttcagcgtgtcgctgcactggagcaagcgcttcgagggcgacccggccaaccgttggttgcggca
ggtgatcacggcgctgttctccgagcgcggctgaagttcgaccaccaaagtacgcgccgcgcggtgcaagcgcgcgc
gactgcgcgagtaacacgccgagagattcccctacagctttctcgcccagttgctgcatcgcaacattcttttgggg
tgcatgacgcgcgaaatacgatgaaagccttcgattccgaaagccgcgattcaggtcgcaacttcgggatgaaatct
ttcgcgctcaaagacgttcgtgaaatgttttcttccctaaaaccgtcactgaaagtgttgaaaccacttgtacagtg
gactggcaatgtgaacggattgttaccgcggagcaccggcatttctccttgagcggccgatgcacgacgcgtccatt
tcacgcgcacatgcatcgttgccaatttcactcaagacctggagaagtgcatgagtaccgtcgatcagctgggccgc
accgccccccttacctcggggcagatggcgatgtggctcggcgcaaagttcgcgtcgcccgacaccaatttcaatct
cgccgaagccatcgacatcgcaggcgagatcgaccccgcgatcttcctggcggccatgcgacaggtggccgatgaag
tcgaggccacgcgcctgagcttcatcgataccccgcaagggccacgacaggtcgtcgcgcccgttttcaccggcgag
atcccctacctcgacctcagcggcgagagcgatccgcaggccgaggccgagcgctggatgcatgcggactacacccg
cagcatcgacctcgcgcacgggcagctgtggctgtccgcgctgatccgcctcgcgcccgatcgccacatctggtacc
accgcagccatcacatcgcgctcgacggcttcagcggcggcctcatcgcacgccgcttcgccgacatctacaccgcg
atggtcgacaacaacgcagcggtgcccgaagactcgcgccttgcaccgatctcgcagctggccgacgaagaacatgc
ctatcgcgagtccggccgcttcccgcgcgaccgccagtactggaccgagcgcttcgccgatgcacccgatccgttga
gcctcgcctcgcaccgctcggtcaacgtcggtggcctcttgcgccagacggtgcacctgccggcggccagcgtgcaa
gccctgcagaccatcgcgcaagagctcggcaccacgctgccgcaaatcctcatcgccaccaccgcggcctacctgta
ccgcgcaacgggcatcgaggacatggcaatcggcatccccgtcaccgcgcgccacaacgaccgcatgcgccgcgtgc
ccgcgatggtggccaacgcgctgccgctgcgcctggcgatgcgcgcggacctgccgattccggaactgatccgcgaa
gtcggccggcagatgcggcagatcctgcggcaccagtcgtatcgctacgagcatttgcgcagcgacctcaacatgct
ggtgaacaaccggcagctcttcaccaccgtggtcaacgtcgagcccttcgactacgacttccgctttgcgggccatg
ccgcgaagccgcgcaacctctcgaacggcacggccgaggacctcggcatcttcctgtacgagcgcggcaacgggcag
gacctgcagatcgacttcgacgccaaccccgcggtgcacaccgcagaggaactggccgatcaccagcgccggctgct
tgccttcatcgacgccgtgatccgcctgccgttgcaggccgtcggccagatcgacctgctcggtgccgaagagcggc
agcaattgctggtcgagtggaacgacacggcccacgccgtgcccgacacccatctcaccgcgttgatcgaagcgcag
ctcgcagccgatccgcaagccatcgcattgcgcttcgacggcgaggcgatgaacaacgaagaactgaaccgccgcgc
caaccgtctcgcccacctgctgcgcgcacgcggcgctggcccggagcgcaccgtggcgctcgcgatcccgcgttcga
tggacctgatgattgccttgctcgccacgttgaagaccggcgcggcctacctgccggtcgatccggatttcccggcg
gaccgcatcgccttcatgctcggcgatgcgcagcccgtgtgcctcgtcacgaccgaagccctcgcggagtcgctgcc

Fig. 4 ggcagccgcccccacattgctgctcgatgtagcgcaaacgattgcggatctggagagttgcaacgacaccaacccgg
gcatcgcgatcgacccttcgcatccggcctatgtgatctacacctcgggctcgaccggcatgcccaagggtgcggtc
gtgtcgcaccgcgccatcgtcaaccgcctgcgctggatgcaggaccgctacggccttcaggccgacgaccgcgtgct
gcagaagacgccttccagcttcgacgtgtcggtgtgggagttcttctggccgctgatcgacggtgccacgctggtgc
ttgcgaaaccgggcggccacaaggatgcggcctacctcgcggggctgatcgcggaggagggcatcaccacgatccac
ttcgtgccgtcgatgctcgaggtcttcctgctcgagcccacggcgggcgcatgcaccacgctgcgccgcgtgatctg
cagcggcgaagccttgtcgcccgcgctgcaatcgcagttccagcagcacctctcgtgcgagctgcacaacctctacg
gtccgaccgaggccgcggtcgacgtcacctcgtgggagtgcgaacgcacggacgacgcagaagcctcgagcgttccc
atcggccgcccgatctggaacacccagatgcacgtgctcgacagcggcctgcagcccgtgccggccggcgtgactgg
cgagctgtacatcgcgggcgtcggcctcgcacgcggctacctcaagcgcccgttgctgagcgccgagcgtttcatcg
ccaacccctacggcacacccggcagccgcatgtaccgcaccggcgacctcgcgcgctggcgcaaggacggcagcctt
gacttcctcggccgcgccgaccagcaggtgaagatccggggcctgcgcatcgagccgggagagatcgaatccgtgct
gctgcagcatccgcaagtcgcgcaggccgccgtggtggcgcgcgaagacgtaccgggcgaaaagcgtctcgtggcct
acgtcgttgcgacggacgctgccgatccgcaagcggccgaactgcgcacgcgcctcgcgcaatcgctgcccgagtac
atggtgccttcggccttcgtcagcctcccgtcgctgccgctcggacccagcggcaagctcgaccgcaaggcgctgcc
gccccccgaagtgcaggccgccacgccgtacgccgcgccgcgcacgccgaccgaaaagatcctggccggcctctggg
ccgagacgctgcatttgccgcgcgtcggtgtcaacgacaacttcttcgaactcggcggccactcgctgatgatcgtg
cagctcatgtcgatgatccggcagcaattcatgatcgacctgccggtcgacacgctgttccaggtctccaccatcgc
gggccttgccgagctgctcgaccaggaatcggtcgcccgtccgagcctgactccgatgccgcgccccgcgcgcattc
cgctgtccttcgcgcagcgccgcctgtggctgatgaaccagctcgaaggcgcgaacccggcctacaacatgccgctc
gcgctgcgcctgtcgggtgtgctcgatcgcaccgcattgcatgcggcgctcggcgacctggtgcagcgccacgagag
cctgcgcacggtctacccgaacgaagacgggctgccgtaccagcacatcctcgacggcgcggatgcgcgtccggcgg
tgatcgaggccgacagcagcgaagaagaaatcgcggcgcagcttcacgccgctgcgggccatgccttcgatctcggc
agcgcggcgcccttgcgcgtctacctgttcaagctcgccggcgacgaacacgtgctgctgctgctcacgcaccacat
tgccggcgatggcgcctcgctgctgccgctagcgcgcgacatcagcgtggcctatgccgcgcgctgcgaaggcaagg
cgccgggctgggagccgctgccgctgcaatacgccgactacgcgctgtggcagcaggagctgctcggcagcgaagac
gatgccgagagcatggccggccgccagcgtgagttctggcgttcctcgctgagcgacctgcccgagcaactggcgct
gcccgtcgaccacgcacggccgctcgtgccgacctaccgcggcgatgtggtcccgctgcagattccgtcgcatgtgc
atgaacgcatcctgcaactggcgcgcgacgggcaggccagcgtcttcatggtgctgcaggccgcactcgcgggcctc
ctgagccgcctcggcgcgggcgacgacatcgtcatcggcagcccggtcgcggggcgcagcgaccatgcgctggacga
actcatcggctgcttcgtcaacacgctggtgctgcgcactgacacctcgggccagccgagcctgcgcgagctggtct
cgcgcgtgcgcgccaccaacctcgcggcctatgcgaaccaggagtttccgtacgaccgcctcgtggagctgctgcgt
ccgggccgctcgcgcgccaacctgccgctgttccaggtcatgctgggcttccagggcacgagccgcctgtcgttcag
cctgccgggcctgtcgatcgcgccgcagccggtggccatcgacaccgcgaagttcgacctgtcgttcatcctcggcg
agcaacgcggtgccgatggcctgccgggcggcatctccggcggcatccagtacagcaccgacctgttcgagcgcagc
acggtcgaggccatgggcgcgcggctggtgcgtttgctggaagaggcctgcgaggcgcccgacgatgcggtgagtgg
cctcgccatcctgagcgcggaagaaacgaccgcctgctgtccgactggagcggccgcacgcgcgaccttgcgccgc
tctcgttcgccgacatggtggcctcgcatgccgcggagcgcccgcttgcagatgcagtggtgctcgacgacgcgacc
gtcagctacgccgaactcgatgcacgcgccaaccggctctcgcacctgctgcgtgcgcaaggcatcggggttggcgc
catcgtcgcgacagtgctgccgcgttcgctcgacctcatcgtggcgcacttggccatcgtgaaggccggcgcggcct
acctgcccatcgaccccaaccacatggccgcgcgcagcgccttcgtgttcgaggaggccgcgcccgccgcggtgctg
acgcacgatgcgctgttgcccgagctggtcggcgttccccgctgcatcgcgctcgacagcgacagcatggttgccgc
gctggccatccagtcggatacgccgctggtgcatgcggccaatccacaggatgccgcctacctcatctacacctccg
gctccaccggcatgcccaagggcgtggtggtgccgcatgcgggcctgggcagcctcggcaccgcgatggcggagcgg
ctcgtcatcggccacggctcgcgcgtgctgcagttctcctccagcggcttcgacgcgtcggtgatggaccagctgat
ggcctttggcgccggtgccgcgctggtggtgccggggccggagcaactgctcggcacggagctggccgatctgctcg
agaagcaggccgtgagccacgcgctgattccgcccgccgcgctcgcgaccctgccgcacggcgagttcccgcacctg
cagacgctggtggtcggcggcgatgcctgcaccgccgcgctggcggcgaagtggtcgcaaggccgccgcatgatcaa
cgcctacggcccgaccgagatcaccatctgcgcgagcatgagcgcgccgatgacggccgaggagttgccctccatcg

Fig. 4 (Cont. 1)

gccagccgatctggaacacgcggatgtatgtgctcgacagcgccctgcaaccggtgccgccgggtgtcgcgggcgag
ctctacatcgccggcagcggcgtggcgcgcggctatctcaaccggccggcattgagtgcggaacgcttcatcgccga
cccgcatggcgcgcccggcagccgcatgtaccgcagcggcgacctcgcacgctggcgcgccgacggcacgctcgact
tcctcggccgcgccgaccagcaggtgaagatccggggcttccgcatcgagccgggcgagatcgaatccgtgctgctc
aagcacccgttgatcacgcaggccgccgtgatcgcccgcgaggacgtgcccggcgagaagcgcctggtcgcctactt
cgtcgccggttccgagccgcagcccaccgagctgcgcgcccacatggcgcaggccttgcccgactacatggtgcctt
cggccttcgtgcgcctgccgtcgctgccgctcacgcaaagcggcaagctcgacaagaaggcgctgccggtgcccgac
cagcagcccgccgcgctgtacgtggagccccgcacgccgaccgagaaactgctcgcgggcctctggtccgagacgct
gcacctggagcgtgtcggcatccacgacaacttcttcgagatcggcgggcattcgctcatggcgatccagctgggca
tgcgcatccgccagcaggtgcgcgcggacttcccgcacgccgaggtctacaaccgcccgacgattgccgacctggcc
gcctggctcgacaacgaaggcggcacggtcgaggcgctggacctgtcgcgcgagctcgacctgcccgcgcacatccg
cccgcaggccactgcaccgaagctcgcaccgcgccgcgtgttcctcaccggcgcgagcggcttcgtcggcagtcacc
tgctggccgcgctgttgcgcgacaccgcggcctgcgtggtctgccacgtgcgcgcgcccgacgagcaggccggcgag
cagcgcctcaagcgcacgctggcccagcgccagctcggtgcgatctgggacaacgcgcgcatcaaggtcgtgaccgg
cgacctcggcaagccgcgcctgggcctcgatgacgctgccgtgcaactggtgcgcgacggctgcgacgccatctacc
actgcgccgcgcaggtcgacttcctgcatccctacgcgagcctcaagcccgcgaacgtcgacagcgtggtcacgctg
ctcgaatggacggcgcaggggcgcgcgaagagcatgcactacgtctccacgctggctgtgatcgaccagaacaacaa
ggaagacaccatcaccgagcaatcggcgctggcctcatggagcgggctggtcgacggctacagccagagcaagtggg
tcggcgatgcgctggcccgcgaggcgcaggcgcgcggcatgccggtggcgatctaccggctgggggcagtcaccggc
gaccacacgcacgcgatctgcaatgccgacgacctgatctggcgcgtggcgcatctctatgccgacctggaagcgat
tcccgatatggacctgccgctcaacctcacaccggtggacgacgtggcgcgcgccatcctcggccttgcggcgcagg
aggcctcgtggggccaggtgttccacctgatgagccaggcggcgctgcgggtgcgcgacattccgcacgtcttcgag
cgcatgggcatgcggctggagccggtcgggctggagccctggctgcagcgcgcgcatgcacggctggccgtcgcgca
tgaccgcgacctggccgcggtgctcgccatcctcgaccgctacgacaccacggccacgccgccgcaggtgagcggcg
cggccacgcatgcgcagctcgaggccatcggcgcgccgatccgcccggtggaccgcgacctgctgcagcgctacttc
gtcgacctgggcatcgacaccaaggcgcgccgcgccctggaaaccaccacttcataggagcacacggaatggcacgc
tatctcatcgcagcaaccgccttgccgggacacgtcctgccgatgctggccatcgcgcagcatctggtgaaccaggg
gcacgaggtgcgggtgcacaccgcgagccagttcagggcgcaggccgaggcgaccggtgcgggcttcacgcccttcg
agcgcacgatcgacttcgactaccgcgacctggacaagcgctttcccgagcgccagcgcatcgcctcggcgcatgcg
cagctgtgcttcggcctgaagcacttctttgccgatgcgatggccgcgcagcatgcgggcctgcaatcgatcctcga
agacttcgaggccgatgccatcgtggtcgacacgatgttctgcggcactttcccgctgctgctaggcaaggagcgcg
aagaccgcccggccatcgtcggcatcggcatctcggcgctgccgctctcgagctgcgacaccgccttcttcggcacc
gcgctgccgccgtcgtccacgccggaagggcgggtgcgcaacaaggcgatgaacgccaacctcaaacaggcgatgtt
cggcgaggtgcaacgctacttcgacacgctgctcgcgcgttcgggcctggccgcgctgcccgatttcttcgtcgatg
cgatggtgaagctgcccgatctttacctgcagctcaccgcgccttcgttcgaatacccgcgcagcgacctgcccgcg
tcggtgcatttcgtcggcccgctgctctcgcccgcgagccgcgacttcacgccgcccgagtggtggcacgagctgga
cgacggccgctcggtcgtgctggtcacgcagggcacgctggccaaccagaatccgtcgcagctgatcggcccgacgc
tgcaggcgctggccggcgacaagaacatcctcgtcatcgccaccaccggcggcccggtgccgcccgccctgacggtg
aacctgcccgccaacgcccgcgtggtgccgttcctgccctacgaccggctgctgcccaagctgcacgcgatggtcac
caacggcggctacggctcggtcaaccatgcattgagcctcggtgtgccgctggtggtggccggcacctccgaagaga
agcccgagatcgccgcgcgcgtggcctggtcgggcgcgggcatcaacctcgccaccggccagccgaccgcgcgccag
gtcggcgacgcggtgcgcaaggtactgggcaactcgacctatcgccagcgtgcggcggtgctgcgtgaggacttcgc
ttgccatcgcgcgctgaccggcatcgccggcgccctcgaggcacttctgcaaaccttcgcatccgcggaaatggctt
gaacctgaaccccatacgacaaaggaaatcccagatgagcaacccgttcgacgacaagaacgccagcttccaggtgc
tggtgaacgacgagggccagcactcgctgtggcccgccttcatcgccgtgcccgccggctggcaggtggcgctggcg
ccgaccgaccgcgacgcctgcagcgcctacatcgcggcgaactggcaggacatgcgcccgcgttcgctggtggtggc
cacggcggccggctgacgccgaggatgtccttcccgttcggtgccgtcgtcgtcacctatttcccgaccggcgagca
agtggcgaacctccattcgctggcggcctcgtgtccgcacctctgcgtggtcgacaacacgccgcaggtgggcgatt
ggcatgcggcgctcgtcgatgcgggcgtttcggtgctgcacaacggcaaccgcggcggcatcgcgggcgccttcaac

Fig. 4 (Cont. 2)

cgcggcatcatcgacctcgaagcgcggggcgccgaactcttcttcctgctcgaccaggattcgaagctgccacccgg
ctacttcgatgccatgtgcgaggctgcgatggtggcccgggagcggaagggcgagggcaatggtgaggaagacgcgg
ccttcctgatcggcccgctcgtccacgacacgaacctggacgcgctgatcccgcaattcggcctccagggcaaacgc
gtctaccagttcgacctgcggcagcccttcaccgagccgctgatgcgctgcgccttcatgatttcctcgggctccct
gatttcgcgcggcgcctgggcccggatcggccggttcgacgagcgctatgtgatcgaccacgtggacaccgactact
gcatgcgtgccctgggtcgcggcgtgccgctctacctgaatccgcacgtcgtgctgcggcaccagattggcgacatc
cgtgcccggtcgctgttcggctggaagatccacttcatcaactacccggccgcgcggcgctactacatcgcgcgcaa
tgccatcgatctctcgcgggcgcatgtgcgcgcctttcccgcgatcctgttcatcaacgtttacacgctcaagcaga
tcctgccgatgctgatgttcgagcgcgaccgcttcaagaagaccatcgcgctgatgctcggctgcttcgatggcctg
ttcgggcggctcgggggcctcggcgaggtgcatccgcggatgggcaaatacctgggccgcagcgattgaccgccacc
cttccagcgccgcgcgtacgccgcgccgcgctcgccttcatcttcgtcacggtgctgatcgacttcatggcgttcgg
cctgatcctgcccggcctgccgcacctggtggagcggctggccggcggcagcacggtaacggcggcgtactggatcg
ctgtgttcggcaccgcgttcgcggcgatccagttcgtgagctcgccgatccagggcgcgctgtccgaccgcttcggg
cggcggccggtgatcctgctgtcgtgcttcggcctcggcgtggatttcgtgttcatggccctggccgacagcctgcc
gtggctgttcgtcggccgggtggtctccggcgtgttctcggccagcttcaccatcgccaatgcctacatcgccgatg
tgacgctgccggaggagcgcgcccgcagctacggcatcgtgggggccgcgttcggcatgggcctggtgttcgggccg
gtgctcggcgggcaactgagccacatcgatccgcgcctgccgttctggttcgcggccggcttgacgctgctcagctt
ctgctacggatggttcgtgttgcccgaatcgctgccgcccgagcggcgtgcccgcaagttcgactggtcgcatgcca
atccggttgggacgctggtgctgctcaagcgctatccgcaggtgttcggactggcggcggtgatcttcctcgtgaac
ctggctcagtacgtctatcccagcgtgttcgtgctgttcgccgactaccggtatcactggaaggaagacgccgtggg
ctgggtgctcggcgcggtgggcgtgctcagcgtgctggtcaatgcgctgttgatcgggccgggcgtgaagcgcttcg
gcgagcgccgcgccctgttgctcggcatgggcttcggcgtgctcggcttcgtcatcatcgggtttgccgacgctgga
tggatcctcctggccggggtgccgttcggcattctgctggcgttcgccggaccggcggcgcaggcgctggtcacgct
gcaggtcggcaccgccgagcagggccgcatccagggggcgctcaccagcctggtgtcggtggcgggcatcgtcgggc
cggcgatgttcgccggcagcttcggttacttcatcggcgcggacgcgccggtgcacttgccgggcgcgccgtttttc
ctcgctgcggcgttcctctgcatcggcacgctgatcgcgtggcgctacgcacagccgaagcccgcgacggcagcggt
gcccgagccgacctga

Fig. 4 (Cont. 3)

```
SEQ ID NO 2
LENGTH: 3959
TYPE: DNA
ORGANISM: Variovorax paradoxus

SEQUENCE: 2
   1 CCGCTGCGCC TCGCAACGGG TTTGCTCCTT CGGTGCATCG CGATCCCTGC GGGTGCGATG
  61 GCTCTCCAGA CGGCGTTTGA TGTGATGCAG TACTGACCCC CTGTTCGGGC CGACCTGAGC
 121 GTTTATGGGA GTTTGCGCCT TCGGTAGGGC CACCGGGGTG GCCCGCTCTC CTGCAGTGGG
 181 GCGATTGTAG GTGGGCACTG CCAATGCGCC AACCCCGGGA GTTTCGGCCC TTGGGCCGAT
 241 GGGATAATCA TCCGTTCATT CGCCGGAGGG CGATCGTTCG ACAACAACAG GGGACCCCAT
 301 GATCCTGGTA ACCGGCGGCG CAGGCTTCAT TGGCGCCAAT TTCGTACTCG ACTGGCTCGC
 361 ACAGAGCGAT GAACCGGTCG TGAACCTAGA CAAGCTGACC TACGCGGGCA ACCTCGAGAC
 421 GCTCGCATCG CTCAAGGACA ACCCGAAGCA CATCTTCGTG CAGGGCGACA TCGGCGACAG
 481 CGCGCTGCTC GACCGCCTGC TGGCCGAGCA CAAGCCGCGT GCCGTGGTCA ACTTCGCGGC
 541 CGAATCGCAC GTCGACCGCT CGATCCACGG CCCCGAAGAC TTCGTGCAGA CCAACGTGCT
 601 GGGCACCTTC CGCCTGCTCG AATCCGTGCG CGGTTTCTGG AATGCCCTGC CGGCCGACCA
 661 GAAGGCCGCC TTCCGCTTCC TGCATGTGTC GACCGACGAG GTCTACGGCT CGCTCTCCAA
 721 GACCGACCCG GCCTTCACCG AAGAGAACAA GTACGAGCCC AACAGCCCGT ACTCGGCCAG
 781 CAAGGCCGCC AGCGACCACC TCGTGCGCGC CTGGCACCAC ACCTACGGCC TGCCGGTGGT
 841 CACCACCAAC TGCTCGAACA ACTACGGGCC GTTCCACTTC CCCGAGAAGC TCATTCCCCT
 901 GATGATCGTC AACGCGCTGG CGGGCAAGCC GCTGCCCGTG TACGGCGACG GCATGCAGGT
 961 GCGCGACTGG CTCTACGTGA AGGACCACTG CAGCGCCATC CGCCGCGTGC TCGAAGCCGG
1021 CAAGCTCGGC GAGACCTACA ACGTGGGCGG CTGGAACGAG AAGCCCAACA TCGAGATCGT
1081 CAACACCGTC TGCGCGCTGC TCGACGAGCT GAGCCCCAAG GCCGGCGGCA AGCCGTACAA
1141 GGAACAGATC ACCTATGTGA CCGACCGCCC CGGCCACGAC CGCCGCTACG CGATCGACGC
1201 ACGCAAGCTC GAGCGCGAAC TCGGCTGGAA ACCTGCCGAG ACCTTCGACA GCGGCATCCG
1261 CAAGACGGTC GAGTGGTACC TCGCGAACGG CGAGTGGGTG CGCAACGTGC AAAGCGGCGC
1321 GTACCGCGAG TGGGTCGAGA AGCAATACGA CGCCGCACCG GCGAAGGCCA CCGCATGAAG
1381 CTGCTGCTGC TGGGCAAGGG CGGACAGGTC GGCTGGGAGC TGCAACGCAG CCTCGCGCCC
1441 CTGGGCGAAC TGGTGGCGCT CGATTTCGAC AGCACCGACT TCAACGCCGA CTTCAGTCGC
1501 CCCGAGCAGC TGGCCGAGAC AGTGCTGAAG GTGCGCCCCG ACGTCATCGT CAATGCCGCA
1561 GCGCACACCG CGGTCGACAA GGCCGAGAGC GAGCCCGAGT TCGCGCGCAA GCTCAACGCC
1621 ACCTCGCCCG GCGTGGTGGC CGAAGCCGCG CAGCAGATCG GCGCGCTGAT GGTTCACTAC
1681 TCGACCGACT ACGTCTTCGA CGGCAGCGGC AGCAAGCCGT GGAAAGAAGA CGATGCGACC
1741 GGCCCGCTCA GCGTCTACGG CAGCACCAAG CTCGAAGGCG AGCAACTGGT GGCAAAGCAC
1801 TGTGCGAAGC ACCTGATCTT TCGCACCAGC TGGGTCTATG CCGCGCGCGG CGGCAACTTC
1861 GCCAAGACCA TGCTGCGCAT CGCCAAGGAG CGCGACAAGC TGACCGTCAT CGACGACCAG
1921 TTCGGCGCGC CCACCGGCGC GGAACTGCTG GCCGACATCA CCGCGCACGC GATTCGCGCG
1981 ACGCTGCAGG ACCCGTCCAA GGCCGGGCTC TATCACGCGG TGGCCGGTGG CGTGACCACG
2041 TGGCACGGCT ATGCGCGCTT CGTGATCGAG CAGGCCAAGG CGGCGGGCGT GGAACTGAAG
2101 GCCGGCCCCG AAGCGGTCGA GCCCGTGCCC ACCACGGCAT TCCCGACGCC GGCCAGGCGG
2161 CCGCACAACT CGCGCCTGGA CACCACCAAG CTGCAATCGA CCTTCGGCCT CGTGCTGCCC
2221 GAGTGGCAGT CCGGCGTCGC CCGCATGTTG CGCGAAACCT TCTGATATTC GCAGAGCAAG
2281 AGAGACACGA ACACCCCATG ACCAAGACGA CGCAACGCAA AGGCATCATC CTCGCCGGTG
2341 GCTCGGGCAC CCGCCTGCAC CCCGCGACGC TTGCCATGAG CAAACAACTG CTGCCGGTGT
2401 ACGACAAGCC GATGATCTAT TACCCGCTGA GCACGCTGAT GCTGGGCGGC ATGCGCGACA
2461 TCCTGATCAT CAGCACGCCG CAGGACACGC CGCGTTTCCA GCAACTGCTG GGGGATGGCA
```

Fig. 5

```
2521 GCCAATGGGG CATCAACCTG CAGTACGCGG TGCAGCCGAG CCCGGATGGT CTGGCGCAGG
2581 CGTTCATCAT CGGTGACAAG TTCGTGGGCA ACGACCCGAG TGCGCTGGTG CTGGGGGACA
2641 ACATCTTCTA TGGCCACGAC TTCGCCCATC TGCTGGCCGA TGCCGACGCC AAGACCTCGG
2701 GTGCGACGGT GTTCGCCTAC CACGTGCACG ACCCCGAGCG CTACGGCGTG GTGGCCTTCG
2761 ATGCCAAGGG CAGGGCGAGC AGCATCGAAG AAAAGCCGCT CAAGCCCAAG AGCAGCTATG
2821 CGGTCACGGG CCTCTACTTC TACGACAACC AGGTCGTCGA CATCGCCAAG GCCGTGAAGC
2881 CGAGCGCGCG CGGCGAACTC GAGATCACCG CGGTCAACCA GGCGTATCTC GACCTCGACC
2941 AGCTGAACGT GCAGATCATG CAGCGCGGCT ATGCGTGGCT CGATACCGGT ACGCACGACA
3001 GCCTGCTGGA AGCCGGGCAG TTCATTGCCA CGCTCGAGCA CCGCCAGGGG CTGAAGATCG
3061 CATGCCCCGA AGAGATCGCA TGGCGCAATG GCTTCATCTC AACCGAGCAA CTCGAAAAGC
3121 TCGCGGCGCC GCTGGAAAAG AGCGGCTACG GCAAGTACCT CAAGCACCTG CTGAACGACG
3181 AGGTGCGCTC GTGAAGGCCA CGCCCACCTC GATTCCTGAC GTGCTCGTGA TCGAGCCGAA
3241 GGTGTTTGGC GATGCACGGG GCTTCTTCTT CGAAAGCTTC AACCAGAAGG CCTTCGACGA
3301 AGCGATCGGC AAGCATGTCG ACTTCGTGCA GGACAACCAT TCGCGATCGG CCAAGGGTGT
3361 GCTGCGGGGG CTGCATTACC AGGTCCAGCA GCCGCAAGGC AAGCTCGTGC GGGTGGTGCG
3421 TGGTGCGGTG TTCGACGTGG CCGTCGACAT CCGCAAGTCG TCGCCGACTT TTGGCAAATG
3481 GGTGGGTGTC GAGTTGAACG AAGACAACCA CAAGCAGCTC TGGGTGCCGG CAGGATTCGC
3541 GCACGGTTTC CTGGTGTTGA GCGAGACCGC GGAATTCCTC TACAAGACCA CCGACTACTA
3601 CGCGCCCGCC CACGAGCGCG CGATTGTCTG GAACGACCCC GCTGTCGGTA TTCGATGGCC
3661 GGATGTGGGA GGGGCACCGG TCCTGTCGAA GAAGGACGAA GACGGGTGTC TTCTGCAAGC
3721 GGCAGAGGTT TTCTAGTGTC CTTTCGTCAG ATAGCGGGGC GGCTTCGCGT ATCGGGATCC
3781 CGCGTTGAGC CCGCAAGAGT GCCCTGAGAG GGGGGGCGAA AAACTCACAA CGCCACTGCC
3841 TCGAGCAAAC GTGCGTCTCG CAGCTTTCTG AAGTTGTTGC ACCTTCTTTT TTTTTCTCTT
3901 ACATCTTTGA AATGATTTTG AAAATCCGCG GCGATCGCAT GCATGCTGCT GGAATCACC
```

Fig. 5 (Cont.)

```
SEQ ID NO 3
LENGTH: 915
TYPE: DNA
ORGANISM: Variovorax paradoxus

SEQUENCE: 3
  1   ATGAATGGCA TGCATATCGA CTCGGTCGAC CTCAATCTGC TGCGCCTGTT CGATGCGGTC
 61   TACCGCGAGC GCAGCGTGAG CCGCGCCGCG GAGTCGCTGG GCCTCACGCA GCCTGCGGCA
121   AGCCATGGGC TGGGACGGCT GCGGCTGCTT TTGAAAGACG CGCTCTTCAC GCGTGCCCCC
181   GGCGGCGTGG CGCCCACGCC GCGCGCCGAC CGGCTCGCGG TGGCGGTGCA GGCGGCGCTC
241   GGCACGATCG AAGCGGCGCT GCACGAGCCC GATCGCTTCG AGCCCCAGGT GTCGCGCAAG
301   AGCTTTCGTA TTCACATGAG CGACATCGGC GAGGGGCGCT TCCTGCCCGC GCTGATGGCG
361   CGGCTCGGCG AGCTGGCGCC CGGCGTGCGG CTGGAGACCC TGCCGCTCTT GCCTGCGGAG
421   GTTGCGCCCG CACTCGACAG CGGCCGCATC GATTTCGCCT TCGGCTTTCT CTCGACCGTG
481   CGCGACACGC AGCGCACGCA TCTTCTGAAA GACCGCTACA TCGTGCTGCT GCGCAAGGGC
541   CATCCCTTTG TGAAGCGCCG GCGCAAGGGG CAGGCGCTGC TCGAGGCGCT GCAGGAGCTC
601   GACTACGTGG CGGTGCGCAC GCACGCCGAC ACGCTGCGCA TCTTGCAGTT GCTCAACCTC
661   GAAGACCGCC TGCGCCTCAC GACCGAGCAC TTCATGGTGC TACCGGCCAT CGTGCGCGCC
721   ACCGATCTCG CGGTGGTGAT GCCGCGCAAC ATCGCGCGAG GGTTTGCGGA GGAGGGCGGC
781   TACGCGATCG TCGAGCCGCC GTTTCCGCTG CGCGATTTCA GCGTGTCGCT GCACTGGAGC
841   AAGCGCTTCG AGGGCGACCC GGCCAACCGT TGGTTGCGGC AGGTGATCAC GGCGCTGTTC
901   TCCGAGCGCG GCTGA
```

Fig. 6

SEQ ID NO 5
LENGTH: 7476
TYPE: DNA
ORGANISM: Variovorax paradoxus

SEQUENCE: 5

```
   1  ATGAGTACCG TCGATCAGCT GGGCCGCACC GCCCCCCTTA CCTCGGGGCA GATGGCGATG
  61  TGGCTCGGCG CAAAGTTCGC GTCGCCCGAC ACCAATTTCA ATCTCGCCGA AGCCATCGAC
 121  ATCGCAGGCG AGATCGACCC CGCGATCTTC CTGGCGGCCA TGCGACAGGT GGCCGATGAA
 181  GTCGAGGCCA CGCGCCTGAG CTTCATCGAT ACCCCGCAAG GGCCACGACA GGTCGTCGCG
 241  CCCGTTTTCA CCGGCGAGAT CCCCTACCTC GACCTCAGCG GCGAGAGCGA TCCGCAGGCC
 301  GAGGCCGAGC GCTGGATGCA TGCGGACTAC ACCCGCAGCA TCGACCTCGC GCACGGGCAG
 361  CTGTGGCTGT CCGCGCTGAT CCGCCTCGCG CCCGATCGCC ACATCTGGTA CCACCGCAGC
 421  CATCACATCG CGCTCGACGG CTTCAGCGGC GGCCTCATCG CACGCCGCTT CGCCGACATC
 481  TACACCGCGA TGGTCGACAA CAACGCAGCG GTGCCCGAAG ACTCGCGCCT TGCACCGATC
 541  TCGCAGCTGG CCGACGAAGA ACATGCCTAT CGCGAGTCCG GCCGCTTCCC GCGCGACCGC
 601  CAGTACTGGA CCGAGCGCTT CGCCGATGCA CCCGATCCGT TGAGCCTCGC CTCGCACCGC
 661  TCGGTCAACG TCGGTGGCCT CTTGCGCCAG ACGGTGCACC TGCCGGCGGC CAGCGTGCAA
 721  GCCCTGCAGA CCATCGCGCA AGAGCTCGGC ACCACGCTGC CGCAAATCCT CATCGCCACC
 781  ACCGCGGCCT ACCTGTACCG CGCAACGGGC ATCGAGGACA TGGCAATCGG CATCCCCGTC
 841  ACCGCGCGCC ACAACGACCG CATGCGCCGC GTGCCCGCGA TGGTGGCCAA CGCGCTGCCG
 901  CTGCGCCTGG CGATGCGCGC GGACCTGCCG ATTCCGGAAC TGATCCGCGA AGTCGGCCGG
 961  CAGATGCGGC AGATCCTGCG GCACCAGTCG TATCGCTACG AGCATTTGCG CAGCGACCTC
1021  AACATGCTGG TGAACAACCG GCAGCTCTTC ACCACCGTGG TCAACGTCGA GCCCTTCGAC
1081  TACGACTTCC GCTTTGCGGG CCATGCCGCG AAGCCGCGCA ACCTCTCGAA CGGCACGGCC
1141  GAGGACCTCG GCATCTTCCT GTACGAGCGC GGCAACGGGC AGGACCTGCA GATCGACTTC
1201  GACGCCAACC CCGCGGTGCA CACCGCAGAG GAACTGGCCG ATCACCAGCG CCGGCTGCTT
1261  GCCTTCATCG ACGCCGTGAT CCGCCTGCCG TTGCAGGCCG TCGGCCAGAT CGACCTGCTC
1321  GGTGCCGAAG AGCGGCAGCA ATTGCTGGTC GAGTGGAACG ACACGGCCCA CGCCGTGCCC
1381  GACACCCATC TCACCGCGTT GATCGAAGCG CAGCTCGCAG CCGATCCGCA AGCCATCGCA
1441  TTGCGCTTCG ACGGCGAGGC GATGAACAAC GAAGAACTGA ACCGCCGCGC CAACCGTCTC
1501  GCCCACCTGC TGCGCGCACG CGGCGCTGGC CCGGAGCGCA CCGTGGCGCT CGCGATCCCG
1561  CGTTCGATGG ACCTGATGAT TGCCTTGCTC GCCACGTTGA AGACCGGCGC GGCCTACCTG
1621  CCGGTCGATC CGGATTTCCC GGCGGACCGC ATCGCCTTCA TGCTCGGCGA TGCGCAGCCC
1681  GTGTGCCTCG TCACGACCGA AGCCCTCGCG GAGTCGCTGC CGGCAGCCGC CCCCACATTG
1741  CTGCTCGATG TAGCGCAAAC GATTGCGGAT CTGGAGAGTT GCAACGACAC CAACCCGGGC
1801  ATCGCGATCG ACCCTTCGCA TCCGGCCTAT GTGATCTACA CCTCGGGCTC GACCGGCATG
1861  CCCAAGGGTG CGGTCGTGTC GCACCGCGCC ATCGTCAACC GCCTGCGCTG GATGCAGGAC
1921  CGCTACGGCC TTCAGGCCGA CGACCGCGTG CTGCAGAAGA CGCCTTCCAG CTTCGACGTG
1981  TCGGTGTGGG AGTTCTTCTG GCCGCTGATC GACGGTGCCA CGCTGGTGCT TGCGAAACCG
2041  GGCGGCCACA AGGATGCGGC CTACCTCGCG GGGCTGATCG CGGAGGAGGG CATCACCACG
2101  ATCCACTTCG TGCCGTCGAT GCTCGAGGTC TTCCTGCTCG AGCCCACGGC GGGCGCATGC
2161  ACCACGCTGC GCCGCGTGAT CTGCAGCGGC GAAGCCTTGT CGCCCGCGCT GCAATCGCAG
2221  TTCCAGCAGC ACCTCTCGTG CGAGCTGCAC AACCTCTACG GTCCGACCGA GGCCGCGGTC
2281  GACGTCACCT CGTGGGAGTG CGAACGCACG GACGACGCAG AAGCCTCGAG CGTTCCCATC
2341  GGCCGCCCGA TCTGGAACAC CCAGATGCAC GTGCTCGACA GCGGCCTGCA GCCCGTGCCG
2401  GCCGGCGTGA CTGGCGAGCT GTACATCGCG GGCGTCGGCC TCGCACGCGG CTACCTCAAG
2461  CGCCCGTTGC TGAGCGCCGA GCGTTTCATC GCCAACCCCT ACGGCACACC CGGCAGCCGC
2521  ATGTACCGCA CCGGCGACCT CGCGCGCTGG CGCAAGGACG GCAGCCTTGA CTTCCTCGGC
2581  CGCGCCGACC AGCAGGTGAA GATCCGGGGC CTGCGCATCG AGCCGGGAGA GATCGAATCC
2641  GTGCTGCTGC AGCATCCGCA AGTCGCGCAG GCCGCCGTGG TGGCGCGCGA AGACGTACCG
2701  GGCGAAAAGC GTCTCGTGGC CTACGTCGTT GCGACGGACG CTGCCGATCC GCAAGCGGCC
2761  GAACTGCGCA CGCGCCTCGC GCAATCGCTG CCCGAGTACA TGGTGCCTTC GGCCTTCGTC
```

Fig. 7

```
2821  AGCCTCCCGT CGCTGCCGCT CGGACCCAGC GGCAAGCTCG ACCGCAAGGC GCTGCCGCCC
2881  CCCGAAGTGC AGGCCGCCAC GCCGTACGCC GCGCCGCGCA CGCCGACCGA AAAGATCCTG
2941  GCCGGCCTCT GGGCCGAGAC GCTGCATTTG CCGCGCGTCG GTGTCAACGA CAACTTCTTC
3001  GAACTCGGCG GCCACTCGCT GATGATCGTG CAGCTCATGT CGATGATCCG GCAGCAATTC
3061  ATGATCGACC TGCCGGTCGA CACGCTGTTC CAGGTCTCCA CCATCGCGGG CCTTGCCGAG
3121  CTGCTCGACC AGGAATCGGT CGCCCGTCCG AGCCTGACTC CGATGCCGCG CCCCGCGCGC
3181  ATTCCGCTGT CCTTCGCGCA GCGCCGCCTG TGGCTGATGA ACCAGCTCGA AGGCGCGAAC
3241  CCGGCCTACA ACATGCCGCT CGCGCTGCGC CTGTCGGGTG TGCTCGATCG CACCGCATTG
3301  CATGCGGCGC TCGGCGACCT GGTGCAGCGC CACGAGAGCC TGCGCACGGT CTACCCGAAC
3361  GAAGACGGGC TGCCGTACCA GCACATCCTC GACGGCGCGG ATGCGCGTCC GGCGGTGATC
3421  GAGGCCGACA GCAGCGAAGA AGAAATCGCG GCGCAGCTTC ACGCCGCTGC GGGCCATGCC
3481  TTCGATCTCG GCAGCGCGGC GCCCTTGCGC GTCTACCTGT TCAAGCTCGC CGGCGACGAA
3541  CACGTGCTGC TGCTGCTCAC GCACCACATT GCCGGCGATG GCGCCTCGCT GCTGCCGCTA
3601  GCGCGCGACA TCAGCGTGGC CTATGCCGCG CGCTGCGAAG GCAAGGCGCC GGGCTGGGAG
3661  CCGCTGCCGC TGCAATACGC CGACTACGCG CTGTGGCAGC AGGAGCTGCT CGGCAGCGAA
3721  GACGATGCCG AGAGCATGGC CGGCCGCCAG CGTGAGTTCT GGCGTTCCTC GCTGAGCGAC
3781  CTGCCCGAGC AACTGGCGCT GCCCGTCGAC CACGCACGGC CGCTCGTGCC GACCTACCGC
3841  GGCGATGTGG TCCCGCTGCA GATTCCGTCG CATGTGCATG AACGCATCCT GCAACTGGCG
3901  CGCGACGGGC AGGCCAGCGT CTTCATGGTG CTGCAGGCCG CACTCGCGGG CCTCCTGAGC
3961  CGCCTCGGCG CGGGCGACGA CATCGTCATC GGCAGCCCGG TCGCGGGGCG CAGCGACCAT
4021  GCGCTGGACG AACTCATCGG CTGCTTCGTC AACACGCTGG TGCTGCGCAC TGACACCTCG
4081  GGCCAGCCGA GCCTGCGCGA GCTGGTCTCG CGCGTGCGCG CCACCAACCT CGCGGCCTAT
4141  GCGAACCAGG AGTTTCCGTA CGACCGCCTC GTGGAGCTGC TGCGTCCGGG CCGCTCGCGC
4201  GCCAACCTGC CGCTGTTCCA GGTCATGCTG GGCTTCCAGG GCACGAGCCG CCTGTCGTTC
4261  AGCCTGCCGG GCCTGTCGAT CGCGCCGCAG CCGGTGGCCA TCGACACCGC GAAGTTCGAC
4321  CTGTCGTTCA TCCTCGGCGA GCAACGCGGT GCCGATGGCC TGCCGGGCGG CATCTCCGGC
4381  GGCATCCAGT ACAGCACCGA CCTGTTCGAG CGCAGCACGG TCGAGGCCAT GGGCGCGCGG
4441  CTGGTGCGTT TGCTGGAAGA GGCCTGCGAG GCGCCCGACG ATGCGGTGAG TGGCCTCGCC
4501  ATCCTGAGCG CGGAAGAAAC CGACCGCCTG CTGTCCGACT GGAGCGGCCG CACGCGCGAC
4561  CTTGCGCCGC TCTCGTTCGC CGACATGGTG GCCTCGCATG CCGCGGAGCG CCCGCTTGCA
4621  GATGCAGTGG TGCTCGACGA CGCGACCGTC AGCTACGCCG AACTCGATGC ACGCGCCAAC
4681  CGGCTCTCGC ACCTGCTGCG TGCGCAAGGC ATCGGGGTTG GCGCCATCGT CGCGACAGTG
4741  CTGCCGCGTT CGCTCGACCT CATCGTGGCG CACTTGGCCA TCGTGAAGGC CGGCGCGGCC
4801  TACCTGCCCA TCGACCCCAA CCACATGGCC GCGCGCAGCG CCTTCGTGTT CGAGGAGGCC
4861  GCGCCCGCCG CGGTGCTGAC GCACGATGCG CTGTTGCCCG AGCTGGTCGG CGTTCCCCGC
4921  TGCATCGCGC TCGACAGCGA CAGCATGGTT GCCGCGCTGG CCATCCAGTC GGATACGCCG
4981  CTGGTGCATG CGGCCAATCC ACAGGATGCC GCCTACCTCA TCTACACCTC CGGCTCCACC
5041  GGCATGCCCA AGGGCGTGGT GGTGCCGCAT GCGGGCCTGG GCAGCCTCGG CACCGCGATG
5101  GCGGAGCGGC TCGTCATCGG CCACGGCTCG CGCGTGCTGC AGTTCTCCTC CAGCGGCTTC
5161  GACGCGTCGG TGATGGACCA GCTGATGGCC TTTGGCGCCG GTGCCGCGCT GGTGGTGCCG
5221  GGGCCGGAGC AACTGCTCGG CACGGAGCTG GCCGATCTGC TCGAGAAGCA GGCCGTGAGC
5281  CACGCGCTGA TTCCGCCCGC CGCGCTCGCG ACCCTGCCGC ACGGCGAGTT CCCGCACCTG
5341  CAGACGCTGG TGGTCGGCGG CGATGCCTGC ACCGCCGCGC TGGCGGCGAA GTGGTCGCAA
5401  GGCCGCCGCA TGATCAACGC CTACGGCCCG ACCGAGATCA CCATCTGCGC GAGCATGAGC
5461  GCGCCGATGA CGGCCGAGGA GTTGCCCTCC ATCGGCCAGC CGATCTGGAA CACGCGGATG
5521  TATGTGCTCG ACAGCGCCCT GCAACCGGTG CCGCCGGGTG TCGCGGGCGA GCTCTACATC
5581  GCCGGCAGCG GCGTGGCGCG CGGCTATCTC AACCGGCCGG CATTGAGTGC GGAACGCTTC
5641  ATCGCCGACC CGCATGGCGC GCCCGGCAGC CGCATGTACC GCAGCGGCGA CCTCGCACGC
5701  TGGCGCGCCG ACGGCACGCT CGACTTCCTC GGCCGCGCCG ACCAGCAGGT GAAGATCCGG
5761  GGCTTCCGCA TCGAGCCGGG CGAGATCGAA TCCGTGCTGC TCAAGCACCC GTTGATCACG
5821  CAGGCCGCCG TGATCGCCCG CGAGGACGTG CCCGGCGAGA AGCGCCTGGT CGCCTACTTC
5881  GTCGCCGGTT CCGAGCCGCA GCCCACCGAG CTGCGCGCCC ACATGGCGCA GGCCTTGCCC
5941  GACTACATGG TGCCTTCGGC CTTCGTGCGC CTGCCGTCGC TGCCGCTCAC GCAAAGCGGC
6001  AAGCTCGACA AGAAGGCGCT GCCGGTGCCC GACCAGCAGC CCGCCGCGCT GTACGTGGAG
6061  CCCCGCACGC CGACCGAGAA ACTGCTCGCG GGCCTCTGGT CCGAGACGCT GCACCTGGAG
6121  CGTGTCGGCA TCCACGACAA CTTCTTCGAG ATCGGCGGGC ATTCGCTCAT GGCGATCCAG
6181  CTGGGCATGC GCATCCGCCA GCAGGTGCGC GCGGACTTCC CGCACGCCGA GGTCTACAAC
```

Fig. 7 (Cont. 1)

```
6241  CGCCCGACGA TTGCCGACCT GGCCGCCTGG CTCGACAACG AAGGCGGCAC GGTCGAGGCG
6301  CTGGACCTGT CGCGCGAGCT CGACCTGCCC GCGCACATCC GCCCGCAGGC CACTGCACCG
6361  AAGCTCGCAC CGCGCCGCGT GTTCCTCACC GGCGCGAGCG GCTTCGTCGG CAGTCACCTG
6421  CTGGCCGCGC TGTTGCGCGA CACCGCGGCC TGCGTGGTCT GCCACGTGCG CGCGCCCGAC
6481  GAGCAGGCCG GCGAGCAGCG CCTCAAGCGC ACGCTGGCCC AGCGCCAGCT CGGTGCGATC
6541  TGGGACAACG CGCGCATCAA GGTCGTGACC GGCGACCTCG GCAAGCCGCG CCTGGGCCTC
6601  GATGACGCTG CCGTGCAACT GGTGCGCGAC GGCTGCGACG CCATCTACCA CTGCGCCGCG
6661  CAGGTCGACT TCCTGCATCC CTACGCGAGC CTCAAGCCCG CGAACGTCGA CAGCGTGGTC
6721  ACGCTGCTCG AATGGACGGC GCAGGGGCGC GCGAAGAGCA TGCACTACGT CTCCACGCTG
6781  GCTGTGATCG ACCAGAACAA CAAGGAAGAC ACCATCACCG AGCAATCGGC GCTGGCCTCA
6841  TGGAGCGGGC TGGTCGACGG CTACAGCCAG AGCAAGTGGG TCGGCGATGC GCTGGCCCGC
6901  GAGGCGCAGG CGCGCGGCAT GCCGGTGGCG ATCTACCGGC TGGGGGCAGT CACCGGCGAC
6961  CACACGCACG CGATCTGCAA TGCCGACGAC CTGATCTGGC GCGTGGCGCA TCTCTATGCC
7021  GACCTGGAAG CGATTCCCGA TATGGACCTG CCGCTCAACC TCACACCGGT GGACGACGTG
7081  GCGCGCGCCA TCCTCGGCCT TGCGGCGCAG GAGGCCTCGT GGGGCCAGGT GTTCCACCTG
7141  ATGAGCCAGG CGGCGCTGCG GGTGCGCGAC ATTCCGCACG TCTTCGAGCG CATGGGCATG
7201  CGGCTGGAGC CGGTCGGGCT GGAGCCCTGG CTGCAGCGCG CGCATGCACG GCTGGCCGTC
7261  GCGCATGACC GCGACCTGGC CGCGGTGCTC GCCATCCTCG ACCGCTACGA CACCACGGCC
7321  ACGCCGCCGC AGGTGAGCGG CGCGGCCACG CATGCGCAGC TCGAGGCCAT CGGCGCGCCG
7381  ATCCGCCCGG TGGACCGCGA CCTGCTGCAG CGCTACTTCG TCGACCTGGG CATCGACACC
7441  AAGGCGCGCC GCGCCCTGGA AACCACCACT TCATAG
```

Fig. 7 (Cont. 2)

SEQ ID NO 7
LENGTH: 1320
TYPE: DNA
ORGANISM: *Variovorax paradoxus*

SEQUENCE: 7

```
   1  ATGGCACGCT ATCTCATCGC AGCAACCGCC TTGCCGGGAC ACGTCCTGCC GATGCTGGCC
  61  ATCGCGCAGC ATCTGGTGAA CCAGGGGCAC GAGGTGCGGG TGCACACCGC GAGCCAGTTC
 121  AGGGCGCAGG CCGAGGCGAC CGGTGCGGGC TTCACGCCCT TCGAGCGCAC GATCGACTTC
 181  GACTACCGCG ACCTGGACAA GCGCTTTCCC GAGCGCCAGC GCATCGCCTC GGCGCATGCG
 241  CAGCTGTGCT TCGGCCTGAA GCACTTCTTT GCCGATGCGA TGGCCGCGCA GCATGCGGGC
 301  CTGCAATCGA TCCTCGAAGA CTTCGAGGCC GATGCCATCG TGGTCGACAC GATGTTCTGC
 361  GGCACTTTCC CGCTGCTGCT AGGCAAGGAG CGCGAAGACC GCCCGGCCAT CGTCGGCATC
 421  GGCATCTCGG CGCTGCCGCT CTCGAGCTGC GACACCGCCT TCTTCGGCAC CGCGCTGCCG
 481  CCGTCGTCCA CGCCGGAAGG GCGGGTGCGC AACAAGGCGA TGAACGCCAA CCTCAAACAG
 541  GCGATGTTCG GCGAGGTGCA ACGCTACTTC GACACGCTGC TCGCGCGTTC GGGCCTGGCC
 601  GCGCTGCCCG ATTTCTTCGT CGATGCGATG GTGAAGCTGC CCGATCTTTA CCTGCAGCTC
 661  ACCGCGCCTT CGTTCGAATA CCCGCGCAGC GACCTGCCCG CGTCGGTGCA TTTCGTCGGC
 721  CCGCTGCTCT CGCCCGCGAG CCGCGACTTC ACGCCGCCCG AGTGGTGGCA CGAGCTGGAC
 781  GACGGCCGCT CGGTCGTGCT GGTCACGCAG GGCACGCTGG CCAACCAGAA TCCGTCGCAG
 841  CTGATCGGCC CGACGCTGCA GGCGCTGGCC GGCGACAAGA ACATCCTCGT CATCGCCACC
 901  ACCGGCGGCC CGGTGCCGCC CGCCCTGACG GTGAACCTGC CCGCCAACGC CCGCGTGGTG
 961  CCGTTCCTGC CCTACGACCG GCTGCTGCCC AAGCTGCACG CGATGGTCAC CAACGGCGGC
1021  TACGGCTCGG TCAACCATGC ATTGAGCCTC GGTGTGCCGC TGGTGGTGGC CGGCACCTCC
1081  GAAGAGAAGC CCGAGATCGC CGCGCGCGTG GCCTGGTCGG GCGCGGGCAT CAACCTCGCC
1141  ACCGGCCAGC CGACCGCGCG CCAGGTCGGC GACGCGGTGC GCAAGGTACT GGGCAACTCG
1201  ACCTATCGCC AGCGTGCGGC GGTGCTGCGT GAGGACTTCG CTTGCCATCG CGCGCTGACC
1261  GGCATCGCCG GCGCCCTCGA GGCACTTCTG CAAACCTTCG CATCCGCGGA AATGGCTTGA
```

Fig. 8

```
SEQ ID NO 9
LENGTH: 213
TYPE: DNA
ORGANISM: Variovorax paradoxus

SEQUENCE: 9
      1  ATGAGCAACC CGTTCGACGA CAAGAACGCC AGCTTCCAGG TGCTGGTGAA CGACGAGGGC
     61  CAGCACTCGC TGTGGCCCGC CTTCATCGCC GTGCCCGCCG GCTGGCAGGT GGCGCTGGCG
    121  CCGACCGACC GCGACGCCTG CACCGCCTAC ATCGCGGCGA ACTGGCAGGA CATGCGCCCG
    181  CGTTCGCTGG TGGTGGCCAC GGCGGCCGGC TGA
```

Fig. 9

```
SEQ ID NO 11
LENGTH: 969
TYPE: DNA
ORGANISM: Variovorax paradoxus

SEQUENCE: 11
      1  ATGTCCTTCC CGTTCGGTGC CGTCGTCGTC ACCTATTTCC CGACCGGCGA GCAAGTGGCG
     61  AACCTCCATT CGCTGGCGGC CTCGTGTCCG CACCTCTGCG TGGTCGACAA CACGCCGCAG
    121  GTGGGCGATT GGCATGCGGC GCTCGTCGAT GCGGGCGTTT CGGTGCTGCA CAACGGCAAC
    181  CGCGGCGGCA TCGCGGGCGC CTTCAACCGC GGCATCATCG ACCTCGAAGC GCGGGGCGCC
    241  GAACTCTTCT TCCTGCTCGA CCAGGATTCG AAGCTGCCAC CCGGCTACTT CGATGCCATG
    301  TGCGAGGCTG CGATGGTGGC CCGGGAGCGG AAGGGCGAGG GCAATGGTGA GGAAGACGCG
    361  GCCTTCCTGA TCGGCCCGCT CGTCCACGAC ACGAACCTGG ACGCGCTGAT CCCGCAATTC
    421  GGCCTCCAGG GCAAACGCGT CTACCAGTTC GACCTGCGGC AGCCCTTCAC CGAGCCGCTG
    481  ATGCGCTGCG CCTTCATGAT TTCCTCGGGC TCCCTGATTT CGCGCGGCGC CTGGGCCCGG
    541  ATCGGCCGGT TCGACGAGCG CTATGTGATC GACCACGTGG ACACCGACTA CTGCATGCGT
    601  GCCCTGGGTC GCGGCGTGCC GCTCTACCTG AATCCGCACG TCGTGCTGCG GCACCAGATT
    661  GGCGACATCC GTGCCCGGTC GCTGTTCGGC TGGAAGATCC ACTTCATCAA CTACCCGGCC
    721  GCGCGGCGCT ACTACATCGC GCGCAATGCC ATCGATCTCT CGCGGGCGCA TGTGCGCGCC
    781  TTTCCCGCGA TCCTGTTCAT CAACGTTTAC ACGCTCAAGC AGATCCTGCC GATGCTGATG
    841  TTCGAGCGCG ACCGCTTCAA GAAGACCATC GCGCTGATGC TCGGCTGCTT CGATGGCCTG
    901  TTCGGGCGGC TCGGGGGCCT CGGCGAGGTG CATCCGCGGA TGGGCAAATA CCTGGGCCGC
    961  AGCGATTGA
```

Fig. 10

```
SEQ ID NO 13
LENGTH: 1260
TYPE: DNA
ORGANISM: Variovorax paradoxus

SEQUENCE: 13
   1  TTGACCGCCA CCCTTCCAGC GCCGCGCGTA CGCCGCGCCG CGCTCGCCTT CATCTTCGTC
  61  ACGGTGCTGA TCGACTTCAT GGCGTTCGGC CTGATCCTGC CCGGCCTGCC GCACCTGGTG
 121  GAGCGGCTGG CCGGCGGCAG CACGGTAACG GCGGCGTACT GGATCGCTGT GTTCGGCACC
 181  GCGTTCGCGG CGATCCAGTT CGTGAGCTCG CCGATCCAGG GCGCGCTGTC CGACCGCTTC
 241  GGGCGGCGGC CGGTGATCCT GCTGTCGTGC TTCGGCCTCG GCGTGGATTT CGTGTTCATG
 301  GCCCTGGCCG ACAGCCTGCC GTGGCTGTTC GTCGGCCGGG TGGTCTCCGG CGTGTTCTCG
 361  GCCAGCTTCA CCATCGCCAA TGCCTACATC GCCGATGTGA CGCTGCCGGA GGAGCGCGCC
 421  CGCAGCTACG GCATCGTGGG GGCCGCGTTC GGCATGGGCC TGGTGTTCGG GCCGGTGCTC
 481  GGCGGGCAAC TGAGCCACAT CGATCCGCGC CTGCCGTTCT GGTTCGCGGC CGGCTTGACG
 541  CTGCTCAGCT TCTGCTACGG ATGGTTCGTG TTGCCCGAAT CGCTGCCGCC CGAGCGGCGT
 601  GCCCGCAAGT TCGACTGGTC GCATGCCAAT CCGGTTGGGA CGCTGGTGCT GCTCAAGCGC
 661  TATCCGCAGG TGTTCGGACT GGCGGCGGTG ATCTTCCTCG TGAACCTGGC TCAGTACGTC
 721  TATCCCAGCG TGTTCGTGCT GTTCGCCGAC TACCGGTATC ACTGGAAGGA AGACGCCGTG
 781  GGCTGGGTGC TCGGCGCGGT GGGCGTGCTC AGCGTGCTGG TCAATGCGCT GTTGATCGGG
 841  CCGGGCGTGA AGCGCTTCGG CGAGCGCCGC GCCCTGTTGC TCGGCATGGG CTTCGGCGTG
 901  CTCGGCTTCG TCATCATCGG GTTTGCCGAC GCTGGATGGA TCCTCCTGGC CGGGGTGCCG
 961  TTCGGCATTC TGCTGGCGTT CGCCGGACCG GCGGCGCAGG CGCTGGTCAC GCTGCAGGTC
1021  GGCACCGCCG AGCAGGGCCG CATCCAGGGG GCGCTCACCA GCCTGGTGTC GGTGGCGGGC
1081  ATCGTCGGGC CGGCGATGTT CGCCGGCAGC TTCGGTTACT TCATCGGCGC GGACGCGCCG
1141  GTGCACTTGC CGGGCGCGCC GTTTTTCCTC GCTGCGGCGT TCCTCTGCAT CGGCACGCTG
1201  ATCGCGTGGC GCTACGCACA GCCGAAGCCC GCGACGGCAG CGGTGCCCGA GCCGACCTGA
```

Fig. 11

SEQ ID NO 15
LENGTH: 1080
TYPE: DNA
ORGANISM: Variovorax paradoxus

SEQUENCE: 15

```
   1 ATGATCCTGG TAACCGGCGG CGCAGGCTTC ATTGGCGCCA ATTTCGTACT CGACTGGCTC
  61 GCACAGAGCG ATGAACCGGT CGTGAACCTA GACAAGCTGA CCTACGCGGG CAACCTCGAG
 121 ACGCTCGCAT CGCTCAAGGA CAACCCGAAG CACATCTTCG TGCAGGGCGA CATCGGCGAC
 181 AGCGCGCTGC TCGACCGCCT GCTGGCCGAG CACAAGCCGC GTGCCGTGGT CAACTTCGCG
 241 GCCGAATCGC ACGTCGACCG CTCGATCCAC GGCCCCGAAG ACTTCGTGCA GACCAACGTG
 301 CTGGGCACCT TCCGCCTGCT CGAATCCGTG CGCGGTTTCT GGAATGCCCT GCCGGCCGAC
 361 CAGAAGGCCG CCTTCCGCTT CCTGCATGTG TCGACCGACG AGGTCTACGG CTCGCTCTCC
 421 AAGACCGACC CGGCCTTCAC CGAAGAGAAC AAGTACGAGC CCAACAGCCC GTACTCGGCC
 481 AGCAAGGCCG CCAGCGACCA CCTCGTGCGC GCCTGGCACC ACACCTACGG CCTGCCGGTG
 541 GTCACCACCA ACTGCTCGAA CAACTACGGG CCGTTCCACT TCCCCGAGAA GCTCATTCCC
 601 CTGATGATCG TCAACGCGCT GGCGGGCAAG CCGCTGCCCG TGTACGGCGA CGGCATGCAG
 661 GTGCGCGACT GGCTCTACGT GAAGGACCAC TGCAGCGCCA TCCGCCGCGT GCTCGAAGCC
 721 GGCAAGCTCG GCGAGACCTA CAACGTGGGC GGCTGGAACG AGAAGCCCAA CATCGAGATC
 781 GTCAACACCG TCTGCGCGCT GCTCGACGAG CTGAGCCCCA AGGCCGGCGG CAAGCCGTAC
 841 AAGGAACAGA TCACCTATGT GACCGACCGC CCCGGCCACG ACCGCCGCTA CGCGATCGAC
 901 GCACGCAAGC TCGAGCGCGA ACTCGGCTGG AAACCTGCCG AGACCTTCGA CAGCGGCATC
 961 CGCAAGACGG TCGAGTGGTA CCTCGCGAAC GGCGAGTGGG TGCGCAACGT GCAAAGCGGC
1021 GCGTACCGCG AGTGGGTCGA GAAGCAATAC GACGCCGCAC CGGCGAAGGC CACCGCATGA
```

Fig. 12

SEQ ID NO 17
LENGTH: 891
TYPE: DNA
ORGANISM: Variovorax paradoxus

SEQUENCE: 17

```
   1 ATGAAGCTGC TGCTGCTGGG CAAGGGCGGA CAGGTCGGCT GGGAGCTGCA ACGCAGCCTC
  61 GCGCCCCTGG GCGAACTGGT GGCGCTCGAT TTCGACAGCA CCGACTTCAA CGCCGACTTC
 121 AGTCGCCCCG AGCAGCTGGC CGAGACAGTG CTGAAGGTGC GCCCCGACGT CATCGTCAAT
 181 GCCGCAGCGC ACACCGCGGT CGACAAGGCC GAGAGCGAGC CCGAGTTCGC GCGCAAGCTC
 241 AACGCCACCT CGCCCGGCGT GGTGGCCGAA GCCGCGCAGC AGATCGGCGC GCTGATGGTT
 301 CACTACTCGA CCGACTACGT CTTCGACGGC AGCGGCAGCA AGCCGTGGAA AGAAGACGAT
 361 GCGACCGGCC CGCTCAGCGT CTACGGCAGC ACCAAGCTCG AAGGCGAGCA ACTGGTGGCA
 421 AAGCACTGTG CGAAGCACCT GATCTTTCGC ACCAGCTGGG TCTATGCCGC GCGCGGCGGC
 481 AACTTCGCCA AGACCATGCT GCGCATCGCC AAGGAGCGCG ACAAGCTGAC CGTCATCGAC
 541 GACCAGTTCG GCGCGCCCAC CGGCGCGGAA CTGCTGGCCG ACATCACCGC GCACGCGATT
 601 CGCGCGACGC TGCAGGACCC GTCCAAGGCC GGGCTCTATC ACGCGGTGGC CGGTGGCGTG
 661 ACCACGTGGC ACGGCTATGC GCGCTTCGTG ATCGAGCAGG CCAAGGCGGC GGGCGTGGAA
 721 CTGAAGGCCG GCCCCGAAGC GGTCGAGCCC GTGCCCACCA CGGCATTCCC GACGCCGGCC
 781 AGGCGGCCGC ACAACTCGCG CCTGGACACC ACCAAGCTGC AATCGACCTT CGGCCTCGTG
 841 CTGCCCGAGT GGCAGTCCGG CGTCGCCCGC ATGTTGCGCG AAACCTTCTG A
```

Fig. 13

SEQ ID NO 19
LENGTH: 897
TYPE: DNA
ORGANISM: Variovorax paradoxus

SEQUENCE: 19

```
  1 ATGACCAAGA CGACGCAACG CAAAGGCATC ATCCTCGCCG GTGGCTCGGG CACCCGCCTG
 61 CACCCCGCGA CGCTTGCCAT GAGCAAACAA CTGCTGCCGG TGTACGACAA GCCGATGATC
121 TATTACCCGC TGAGCACGCT GATGCTGGGC GGCATGCGCG ACATCCTGAT CATCAGCACG
181 CCGCAGGACA CGCCGCGTTT CCAGCAACTG CTGGGGGATG GCAGCCAATG GGGCATCAAC
241 CTGCAGTACG CGGTGCAGCC GAGCCCGGAT GGTCTGGCGC AGGCGTTCAT CATCGGTGAC
301 AAGTTCGTGG GCAACGACCC GAGTGCGCTG GTGCTGGGGG ACAACATCTT CTATGGCCAC
361 GACTTCGCCC ATCTGCTGGC CGATGCCGAC GCCAAGACCT CGGGTGCGAC GGTGTTCGCC
421 TACCACGTGC ACGACCCCGA GCGCTACGGC GTGGTGGCCT TCGATGCCAA GGGCAGGGCG
481 AGCAGCATCG AAGAAAAGCC GCTCAAGCCC AAGAGCAGCT ATGCGGTCAC GGGCCTCTAC
541 TTCTACGACA ACCAGGTCGT CGACATCGCC AAGGCCGTGA AGCCGAGCGC GCGCGGCGAA
601 CTCGAGATCA CCGCGGTCAA CCAGGCGTAT CTCGACCTCG ACCAGCTGAA CGTGCAGATC
661 ATGCAGCGCG GCTATGCGTG GCTCGATACC GGTACGCACG ACAGCCTGCT GGAAGCCGGG
721 CAGTTCATTG CCACGCTCGA GCACCGCCAG GGGCTGAAGA TCGCATGCCC CGAAGAGATC
781 GCATGGCGCA ATGGCTTCAT CTCAACCGAG CAACTCGAAA AGCTCGCGGC GCCGCTGGAA
841 AAGAGCGGCT ACGGCAAGTA CCTCAAGCAC CTGCTGAACG ACGAGGTGCG CTCGTGA
```

Fig. 14

SEQ ID NO 21
LENGTH: 546
TYPE: DNA
ORGANISM: Variovorax paradoxus

SEQUENCE: 21

```
  1 GTGAAGGCCA CGCCCACCTC GATTCCTGAC GTGCTCGTGA TCGAGCCGAA GGTGTTTGGC
 61 GATGCACGGG GCTTCTTCTT CGAAAGCTTC AACCAGAAGG CCTTCGACGA AGCGATCGGC
121 AAGCATGTCG ACTTCGTGCA GGACAACCAT TCGCGATCGG CCAAGGGTGT GCTGCGGGGG
181 CTGCATTACC AGGTCCAGCA GCCGCAAGGC AAGCTCGTGC GGGTGGTGCG TGGTGCGGTG
241 TTCGACGTGG CCGTCGACAT CCGCAAGTCG TCGCCGACTT TTGGCAAATG GGTGGGTGTC
301 GAGTTGAACG AAGACAACCA CAAGCAGCTC TGGGTGCCGG CAGGATTCGC GCACGGTTTC
361 CTGGTGTTGA GCGAGACCGC GGAATTCCTC TACAAGACCA CCGACTACTA CGCGCCCGCC
421 CACGAGCGCG CGATTGTCTG GAACGACCCC GCTGTCGGTA TTCGATGGCC GGATGTGGGA
481 GGGGCACCGG TCCTGTCGAA GAAGGACGAA GACGGGTGTC TTCTGCAAGC GGCAGAGGTT
541 TTCTAG
```

Fig. 15

SEQ ID NO 4
LENGTH: 304
TYPE: PEPTIDE
ORGANISM: *Variovorax paradoxus*

SEQUENCE: 4
MNGMHIDSVDLNLLRLFDAVYRERSVSRAAESLGLTQPAASHGLGRLRLLLKDALFTRAPGGVAPTPRADRLAVAVQ
AALGTIEAALHEPDRFEPQVSRKSFRIHMSDIGEGRFLPALMARLGELAPGVRLETLPLLPAEVAPALDSGRIDFAF
GFLSTVRDTQRTHLLKDRYIVLLRKGHPFVKRRRKGQALLEALQELDYVAVRTHADTLRILQLLNLEDRLRLTTEHF
MVLPAIVRATDLAVVMPRNIARGFAEEGGYAIVEPPFPLRDFSVSLHWSKRFEGDPANRWLRQVITALFSERG

Fig. 16

SEQ ID NO 6
LENGTH: 2491
TYPE: PEPTIDE
ORGANISM: *Variovorax paradoxus*

SEQUENCE: 6
MSTVDQLGRTAPLTSGQMAMWLGAKFASPDTNFNLAEAIDIAGEIDPAIFLAAMRQVADEVEATRLSFIDTPQGPRQ
VVAPVFTGEIPYLDLSGESDPQAEAERWMHADYTRSIDLAHGQLWLSALIRLAPDRHIWYHRSHHIALDGFSGGLIA
RRFADIYTAMVDNNAAVPEDSRLAPISQLADEEHAYRESGRFPRDRQYWTERFADAPDPLSLASHRSVNVGGLLRQT
VHLPAASVQALQTIAQELGTTLPQILIATTAAYLYRATGIEDMAIGIPVTARHNDRMRRVPAMVANALPLRLAMRAD
LPIPELIREVGRQMRQILRHQSYRYEHLRSDLNMLVNNRQLFTTVVNVEPFDYDFRFAGHAAKPRNLSNGTAEDLGI
FLYERGNGQDLQIDFDANPAVHTAEELADHQRRLLAFIDAVIRLPLQAVGQIDLLGAEERQQLLVEWNDTAHAVPDT
HLTALIEAQLAADPQAIALRFDGEAMNNEELNRRANRLAHLLRARGAGPERTVALAIPRSMDLMIALLATLKTGAAY
LPVDPDFPADRIAFMLGDAQPVCLVTTEALAESLPAAAPTLLLDVAQTIADLESCNDTNPGIAIDPSHPAYVIYTSG
STGMPKGAVVSHRAIVNRLRWMQDRYGLQADDRVLQKTPSSFDVSVWEFFWPLIDGATLVLAKPGGHKDAAYLAGLI
AEEGITTIHFVPSMLEVFLLEPTAGACTTLRRVICSGEALSPALQSQFQQHLSCELHNLYGPTEAAVDVTSWECERT
DDAEASSVPIGRPIWNTQMHVLDSGLQPVPAGVTGELYIAGVGLARGYLKRPLLSAERFIANPYGTPGSRMYRTGDL
ARWRKDGSLDFLGRADQQVKIRGLRIEPGEIESVLLQHPQVAQAAVVAREDVPGEKRLVAYVVATDAADPQAAELRT
RLAQSLPEYMVPSAFVSLPSLPLGPSGKLDRKALPPPEVQAATPYAAPRIPTEKILAGLWAEILHLPRVGVNDNFFE
LGGHSLMIVQLMSMIRQQFMIDLPVDTLFQVSTIAGLAELLDQESVARPSLTPMPRPARIPLSFAQRRLWLMNQLEG
ANPAYNMPLALRLSGVLDRTALHAALGDLVQRHESLRTVYPNEDGLPYQHILDGADARPAVIEADSSEEEIAAQLHA
AAGHAFDLGSAAPLRVYLFKLAGDEHVLLLLTHHIAGDGASLLPLARDISVAYAARCEGKAPGWEPLPLQYADYALW
QQELLGSEDDAESMAGRQREFWRSSLSDLPEQLALPVDHARPLVPTYRGDVVPLQIPSHVHERILQLARDGQASVFM
VLQAALAGLLSRLGAGDDIVIGSPVAGRSDHALDELIGCFVNTLVLRTDTSGQPSLRELVSRVRATNLAAYANQEFP
YDRLVELLRPGRSRANLPLFQVMLGFQGTSRLSFSLPGLSIAPQPVAIDTAKFDLSFILGEQRGADGLPGGISGGIQ
YSTDLFERSTVEAMGARLVRLLEEACEAPDDAVSGLAILSAEETDRLLSDWSGRTRDLAPLSFADMVASHAAERPLA
DAVVLDDATVSYAELDARANRLSHLLRAQGIGVGAIVATVLPRSLDLIVAHLAIVKAGAAYLPIDPNHMAARSAFVF
EEAAPAAVLTHDALLPELVGVPRCIALDSDSMVAALAIQSDTPLVHAANPQDAAYLIYTSGSTGMPKGVVVPHAGLG
SLGTAMAERLVIGHGSRVLQFSSSGFDASVMDQLMAFGAGAALVVPGPEQLLGTELADLLEKQAVSHALIPPAALAT
LPHGEFPHLQTLVVGGDACTAALAAKWSQGRRMINAYGPTEITICASMSAPMTAEELPSIGQPIWNTRMYVLDSALQ
PVPPGVAGELYIAGSGVARGYLNRPALSAERFIADPHGAPGSRMYRSGDLARWRADGTLDFLGRADQQVKIRGFRIE
PGEIESVLLKHPLITQAAVIAREDVPGEKRLVAYFVAGSEPQPTELRAHMAQALPDYMVPSAFVRLPSLPLTQSGKL
DKKALPVPDQQPAALYVEPRTPTEKLLAGLWSEILHLERVGIHDNFFEIGGHSLMAIQLGMRIRQQVRADFPHAEVY
NRPTIADLAAWLDNEGGTVEALDLSRELDLPAHIRPQATAPKLAPRRVFLTGASGFVGSHLLAALLRDTAACVVCHV
RAPDEQAGEQRLKRTLAQRQLGAIWDNARIKVVIGDLGKPRLGLDDAAVQLVRDGCDAIYHCAAQVDFLHPYASLKP
ANVDSVVTLLEWTAQGRAKSMHYVSTLAVIDQNNKEDTITEQSALASWSGLVDGYSQSKWVGDALAREAQARGMPVA
IYRLGAVTGDHTHAICNADDLIWRVAHLYADLEAIPDMDLPLNLTPVDDVARAILGLAAQEASWGQVFHLMSQAALR
VRDIPHVFERMGMRLEPVGLEPWLQRAHARLAVAHDRDLAAVLAILDRYDTTATPPQVSGAATHAQLEAIGAPIRPV
DRDLLQRYFVDLGIDTKARRALETTTS

Fig. 17

SEQ ID NO 8
LENGTH: 439
TYPE: PEPTIDE
ORGANISM: Variovorax paradoxus

SEQUENCE: 8
MARYLIAATALPGHVLPMLAIAQHLVNQGHEVRVHTASQFRAQAEATGAGFTPFERTIDFDYRDLDKRFPERQRIAS
AHAQLCFGLKHFFADAMAAQHAGLQSILEDFEADAIVVDTMFCGTFPLLLGKEREDRPAIVGIGISALPLSSCDTAF
FGTALPPSSTPEGRVRNKAMNANLKQAMFGEVQRYFDTLLARSGLAALPDFFVDAMVKLPDLYLQLTAPSFEYPRSD
LPASVHFVGPLLSPASRDFTPPEWWHELDDGRSVVLVTQGTLANQNPSQLIGPTLQALAGDKNILVIATTGGPVPPA
LTVNLPANARVVPFLPYDRLLPKLHAMVTNGGYGSVNHALSLGVPLVVAGTSEEKPEIAARVAWSGAGINLATGQPT
ARQVGDAVRKVLGNSTYRQRAAVLREDFACHRALTGIAGALEALLQTFASAEMA

Fig. 18

SEQ ID NO 10
LENGTH: 70
TYPE: PEPTIDE
ORGANISM: Variovorax paradoxus

SEQUENCE: 10
MSNPFDDKNASFQVLVNDEGQHSLWPAFIAVPAGWQVALAPTDRDACSAYIAANWQDMRPRSLVVATAAG

Fig. 19

SEQ ID NO 12
LENGTH: 322
TYPE: PEPTIDE
ORGANISM: Variovorax paradoxus

SEQUENCE: 12
MSFPFGAVVVTYFPTGEQVANLHSLAASCPHLCVVDNTPQVGDWHAALVDAGVSVLHNGNRGGIAGAFNRGIIDLEA
RGAELFFLLDQDSKLPPGYFDAMCEAAMVARERKGEGNGEEDAAFLIGPLVHDTNLDALIPQFGLQGKRVYQFDLRQ
PFTEPLMRCAFMISSGSLISRGAWARIGRFDERYVIDHVDTDYCMRALGRGVPLYLNPHVVLRHQIGDIRARSLFGW
KIHFINYPAARRYYIARNAIDLSRAHVRAFPAILFINVYTLKQILPMLMFERDRFKKTIALMLGCFDGLFGRLGGLG
EVHPRMGKYLGRSD

Fig. 20

SEQ ID NO 14
LENGTH: 419
TYPE: PEPTIDE
ORGANISM: Variovorax paradoxus

SEQUENCE: 14
MTATLPAPRVRRAALAFIFVTVLIDFMAFGLILPGLPHLVERLAGGSTVTAAYWIAVFGTAFAAIQFVSSPIQGALS
DRFGRRPVILLSCFGLGVDFVFMALADSLPWLFVGRVVSGVFSASFTIANAYIADVTLPEERARSYGIVGAAFGMGL
VFGPVLGGQLSHIDPRLPFWFAAGLTLLSFCYGWFVLPESLPPERRARKFDWSHANPVGTLVLLKRYPQVFGLAAVI
FLVNLAQYVYPSVFVLFADYRYHWKEDAVGWVLGAVGVLSVLVNALLIGPGVKRFGERRALLLGMGFGVLGFVIIGF
ADAGWILLAGVPFGILLAFAGPAAQALVTLQVGTAEQGRIQGALTSLVSVAGIVGPAMFAGSFGYFIGADAPVHLPG
APFFLAAAFLCIGTLIAWRYAQPKPATAAVPEPT

Fig. 21

SEQ ID NO 16
LENGTH: 359
TYPE: PEPTIDE
ORGANISM: Variovorax paradoxus

SEQUENCE: 16
MILVTGGAGFIGANFVLDWLAQSDEPVVNLDKLTYAGNLETLASLKDNPKHIFVQGDIGDSALLDRLLAEHKPRAVV
NFAAESHVDRSIHGPEDFVQTNVLGTFRLLESVRGFWNALPADQKAAFRFLHVSTDEVYGSLSKTDPAFTEENKYEP
NSPYSASKAASDHLVRAWHHTYGLPVVTTNCSNNYGPFHFPEKLIPLMIVNALAGKPLPVYGDGMQVRDWLYVKDHC
SAIRRVLEAGKLGETYNVGGWNEKPNIEIVNTVCALLDELSPKAGGKPYKEQITYVTDRPGHDRRYAIDARKLEREL
GWKPAETFDSGIRKTVEWYLANGEWVRNVQSGAYREWVEKQYDAAPAKATA

Fig. 22

SEQ ID NO 18
LENGTH: 296
TYPE: PEPTIDE
ORGANISM: Variovorax paradoxus

SEQUENCE: 18
MKLLLLGKGGQVGWELQRSLAPLGELVALDFDSTDFNADFSRPEQLAETVLKVRPDVIVNAAAHTAVDKAESEPEFA
RKLNATSPGVVAEAAQQIGALMVHYSTDYVFDGSGSKPWKEDDATGPLSVYGSTKLEGEQLVAKHCAKHLIFRTSWV
YAARGGNFAKTMLRIAKERDKLTVIDDQFGAPTGAELLADITAHAIRATLQDPSKAGLYHAVAGGVTTWHGYARFVI
EQAKAAGVELKAGPEAVEPVPTTAFPTPARRPHNSRLDTTKLQSTFGLVLPEWQSGVARMLRETF

Fig. 23

SEQ ID NO 20
LENGTH: 298
TYPE: PEPTIDE
ORGANISM: Variovorax paradoxus

SEQUENCE: 20
MTKTTQRKGIILAGGSGTRLHPATLAMSKQLLPVYDKPMIYYPLSTLMLGGMRDILIISTPQDTPRFQQLLGDGSQW
GINLQYAVQPSPDGLAQAFIIGDKFVGNDPSALVLGDNIFYGHDFAHLLADADAKTSGATVFAYHVHDPERYGVVAF
DAKGRASSIEEKPLKPKSSYAVTGLYFYDNQVVDIAKAVKPSARGELEITAVNQAYLDLDQLNVQIMQRGYAWLDTG
THDSLLEAGQFIATLEHRQGLKIACPEEIAWRNGFISTEQLEKLAAPLEKSGYGKYLKHLLNDEVRS

Fig. 24

SEQ ID NO 22
LENGTH: 181
TYPE: PEPTIDE
ORGANISM: Variovorax paradoxus

SEQUENCE: 22
MKATPTSIPDVLVIEPKVFGDARGFFFESFNQKAFDEAIGKHVDFVQDNHSRSAKGVLRGLHYQVQQPQGKLVRVVR
GAVFDVAVDIRKSSPTFGKWVGVELNEDNHKQLWVPAGFAHGFLVLSETAEFLYKTTDYYAPAHERAIVWNDPAVGI
RWPDVGGAPVLSKKDEDGCLLQAAEVF

Fig. 25

SEQ ID NO 23
LENGTH: 1029
TYPE: DNA
ORGNAISM: *Variovorax paradoxus*

SEQUENCE: 23
1 ATGGGCAGCA GCCATCATCA TCATCATCAC AGCAGCGGCC TGGTGCCGCG CGGCAGCCAT
61 ATGTCCTTCC CGTTCGGTGC CGTCGTCGTC ACCTATTTCC CGACCGGCGA GCAAGTGGCG
121 AACCTCCATT CGCTGGCGGC CTCGTGTCCG CACCTCTGCG TGGTCGACAA CACGCCGCAG
181 GTGGGCGATT GGCATGCGGC GCTCGTCGAT GCGGGCGTTT CGGTGCTGCA CAACGGCAAC
241 CGCGGCGGCA TCGCGGGCGC CTTCAACCGC GGCATCATCG ACCTCGAAGC GCGGGGCGCC
301 GAACTCTTCT TCCTGCTCGA CCAGGATTCG AAGCTGCCAC CCGGCTACTT CGATGCCATG
361 TGCGAGGCTG CGATGGTGGC CCGGGAGCGG AAGGGCGAGG GCAATGGTGA GGAAGACGCG
421 GCCTTCCTGA TCGGCCCGCT CGTCCACGAC ACGAACCTGG ACGCGCTGAT CCCGCAATTC
481 GGCCTCCAGG GCAAACGCGT CTACCAGTTC GACCTGCGGC AGCCCTTCAC CGAGCCGCTG
541 ATGCGCTGCG CCTTCATGAT TTCCTCGGGC TCCCTGATTT CGCGCGGCGC CTGGGCCCGG
601 ATCGGCCGGT TCGACGAGCG CTATGTGATC GACCACGTGG ACACCGACTA CTGCATGCGT
661 GCCCTGGGTC GCGGCGTGCC GCTCTACCTG AATCCGCACG TCGTGCTGCG GCACCAGATT
721 GGCGACATCC GTGCCCGGTC GCTGTTCGGC TGGAAGATCC ACTTCATCAA CTACCCGGCC
781 GCGCGGCGCT ACTACATCGC GCGCAATGCC ATCGATCTCT CGCGGGCGCA TGTGCGCGCC
841 TTTCCCGCGA TCCTGTTCAT CAACGTTTAC ACGCTCAAGC AGATCCTGCC GATGCTGATG
901 TTCGAGCGCG ACCGCTTCAA GAAGACCATC GCGCTGATGC TCGGCTGCTT CGATGGCCTG
961 TTCGGGCGGC TCGGGGGCCT CGGCGAGGTG CATCCGCGGA TGGGCAAATA CCTGGGCCGC
1021 AGCGATTGA

Fig. 26

SEQ ID NO 24
LENGTH: 342
TYPE: PEPTIDE
ORGANISM: *Variovorax paradoxus*

SEQUENCE: 24
MGSSHHHHHHSSGLVPRGSHMSFPFGAVVVTYFPTGEQVANLHSLAASCPHLCVVDNTPQVGDWHAALVDAGVSVLH
NGNRGGIAGAFNRGIIDLEARGAELFFLLDQDSKLPPGYFDAMCEAAMVARERKGEGNGEEDAAFLIGPLVHDTNLD
ALIPQFGLQGKRVYQFDLRQPFTEPLMRCAFMISSGSLISRGAWARIGRFDERYVIDHVDTDYCMRALGRGVPLYL
NPHVVLRHQIGDIRARSLFGWKIHFINYPAARRYYIARNAIDLSRAHVRAFPAILFINVYTLKQILPMLMFERDRFK
KTIALMLGCFDGLFGRLGGLGEVHPRMGKYLGRSD

Fig. 27

GLYCOLIPOPEPTIDE BIOSURFACTANTS

CROSS REFERENCE TO RELATED APPLICATIONS

This application is a divisional of Ser. No. 16/090,888, filed Oct. 3, 2018, which is the National Stage filing of International Appln. No. PCT/EP2017/058296, filed Apr. 6, 2017, and claims priority of GB Application No. 1605875.2, filed Apr. 6, 2016, the entirety of which applications is incorporated herein by reference for all purposes.

FIELD OF THE INVENTION

This invention relates generally to the fields of surfactant chemistry, biochemistry, and microbiology. More specifically the invention relates to biosurfactants having a hydrophobic lipid oligomer covalently linked to a peptide or peptide-like (e.g. non-proteinogenic amino acid or single amino acid) chain and a carbohydrate moiety, various amino acid and nucleic acid sequences which encode components of biosynthetic pathways for these biosurfactants, and methods of making and using these biosurfactants.

BACKGROUND

Surfactants are amphiphilic chemicals that possess both hydrophobic and hydrophilic moieties which allow them to interact with polar and non-polar systems. Surfactants exert their activity at interfaces between different phases (gas, liquid, solid) and as a result exhibit a range of functions including, but not limited to the ability to act as detergents, emulsifiers, wetting agents and foaming agents. Most chemical surfactants are alkyl sulfates or sulfonates derived from petro- or oleo-chemical sources. The use of these products has been steadily growing with an estimated worldwide consumption of 13 million tonnes in 2008 and an estimated market value of $27 billion (USD) in 2012. In response to environmental and sustainability concerns, many companies utilizing chemical surfactants in their products have been exploring environmentally responsible alternatives as partial or full replacements for chemical surfactants. An alternative to chemical surfactants are biosurfactants, which are surface active molecules originating from microorganisms. These surfactants offer advantages over chemical surfactants such as production from sustainably produced feed stocks, biodegradability and lower toxicity.

SUMMARY

It was discovered that the bacterium *Variovorax paradoxus* RKNM-096, deposited on Apr. 10, 2015 as accession number NRRL B-67038 under the terms of the Budapest Treaty with the Agricultural Research Service Culture Collection (NRRL, 1818 North University Street, Peoria, Ill., 61064) produces a previously unknown class of biosurfactants termed "glycolipopeptides". Unlike known biosurfactants, glycolipopeptides typically contain a hydrophobic lipid oligomer covalently linked to a peptide chain and a carbohydrate moiety.

The deposit of NRRL B-67038 in support of this application was made by Nautilus Bioscience Canada Inc., 550 Unv. Ave., Charlottetown, PE, Canada, C1A4P3. Nautilus Bioscience Canada Inc. authorise the applicant to refer to the deposited biological material in this application and give their unreserved and irrevocable consent to the materials being made available to the public in accordance with appropriate national laws governing the deposit of these materials, such as Rule 31 and 33 EPC. The expert solution under Rule 32 EPC is also hereby requested.

Described herein are purified biosurfactants that include a hydrophobic lipid component including a carboxyl end and a hydroxyl end, wherein the lipid component is covalently linked to (i) a peptide or peptide-like chain at the carboxyl end of the lipid component and (ii) a carbohydrate moiety at the hydroxyl end of the lipid component via a glycosidic linkage. The peptide or peptide-like chain can include a serine-leucinol dipeptide, the lipid component can include three β-hydroxyalkanoic acid moieties (e.g., wherein the length of each acyl chain of the lipid component is $C_6$, $C_8$, $C_{10}$, or $C_{12}$), and the carbohydrate moiety can include a rhamnose moiety attached to the lipid component via a glycosidic linkage. In certain embodiments, the carbohydrate moiety can include two rhamnose moieties and/or an acetyl group. Analogues and derivatives of these glycolipopeptides can be made by conventional methods.

Glycolipopeptides can have the structure:

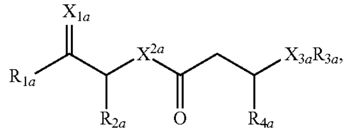

wherein $R_{1a}$ is H, OH, $OCH_3$, SH, $S(CH_3)$, $NH_2$, $NH(CH_3)$, $N(CH_3)_2$, or a peptide or peptide-like structure having the structure:

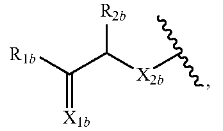

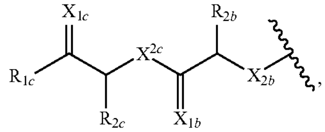

or

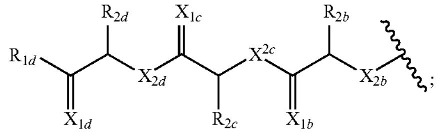

wherein $R_{1b}$, $R_{1c}$, and $R_{1d}$, are H, OH, $OCH_3$, SH, $S(CH_3)$, $NH_2$, $NH(CH_3)$, or $N(CH_3)_2$; $R_{2a}$, $R_{2b}$, $R_{2c}$, and $R_{2d}$ are each independently an amino acid side chain; $X_{1a}$, $X_{1b}$, $X_{1c}$, and $X_{1d}$ are each independently one oxygen atom or two hydrogen atoms; $X_{2a}$, $X_{2b}$, $X_{2c}$, and $X_{2d}$ are each independently NH, $N(CH_3)$, or O; $R_{3a}$ is a carbohydrate portion or a lipid monomer having the structure:

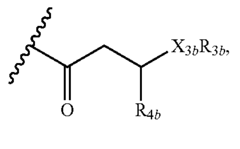

or a lipid oligomer having the structure of:

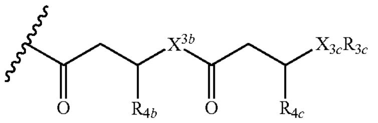

or

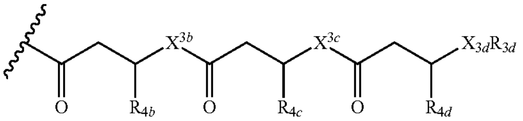

wherein $X_{3a}$, $X_{3b}$, $X_{3c}$, and $X_{3d}$ are each independently NH, $N(CH_3)$, or O; $R_{3a}$, $R_{3b}$, $R_{3c}$, and $R_{3d}$ includes a carbohydrate portion including a monomer having the structure:

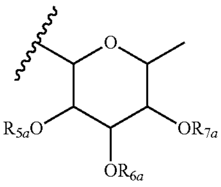

or

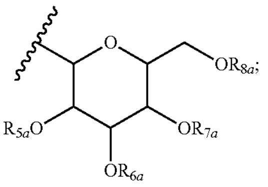

wherein $R_{5a}$, $R_{6a}$, $R_{7a}$, and $R_{8a}$ are each independently a hydrogen atom, methyl, acetyl, or a carbohydrate; and $R_{4a}$, $R_{4b}$, $R_{4c}$, and $R_{4d}$ are each independently a hydrogen atom, methyl, or a $C_2$ to $C_{19}$ saturated or unsaturated linear, branched-chain, cyclic, or aromatic hydrocarbon groups. Naturally occurring glycolipopeptides include those having the following structures:

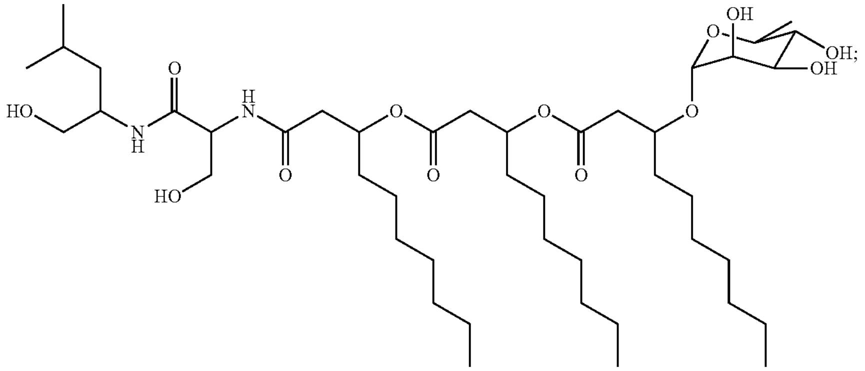

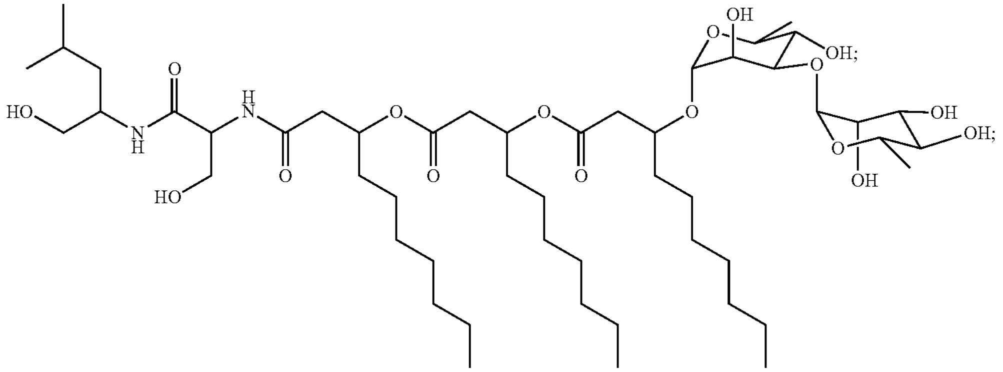

or

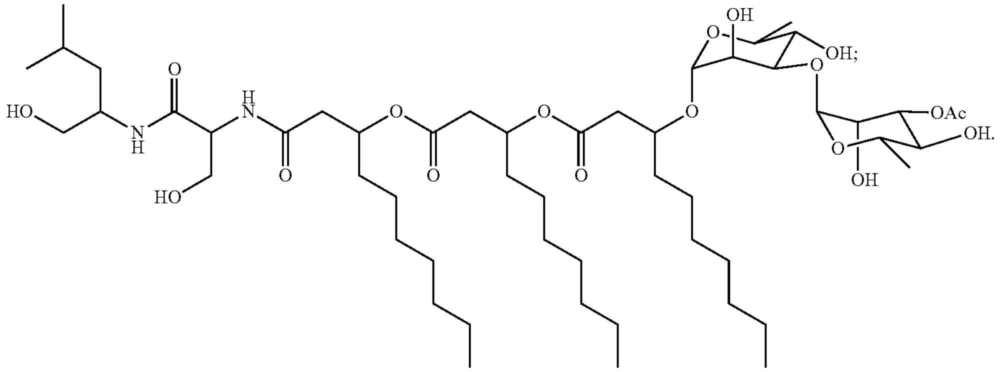

Also described herein are emulsified compositions (e.g., oil-in-water or water-in-oil emulsions) including: a polar component, a non-polar component, and one or more of the above described biosurfactants; and a method of making an water-in-oil or oil-in-water emulsion by mixing together a polar component, a non-polar component, and one or more of the above described biosurfactants. Further described herein are a method of making one of the above described biosurfactants by (a) isolating a microorganism which includes the biosurfactant,
(b) placing the microorganism in a culture under conditions that promote the synthesis of the biosurfactant, and
(c) isolating the biosurfactant from the culture; and an isolated microorganism engineered to produce one of the above described biosurfactants, wherein a set of heterologous genes involved in the biosynthesis of the biosurfactant has been introduced into the microorganism.

Unless otherwise defined, all technical terms used herein have the same meaning as commonly understood by one of ordinary skill in the art to which this invention belongs. Commonly understood definitions of chemical and biological terms can be found in Rieger et al., Glossary of Genetics: Classical and Molecular, 5th edition, Springer-Verlag: New York, 1991; and A Dictionary of Chemistry, Ed. J. Daintith, $7^{th}$ Ed., Oxford University Press, 2016.

As used herein, when referring to a chemical or molecule, the term "purified" means separated from components that occur with it in nature or in an artificially produced mixture. Typically, a molecule is purified when it is at least about 10% (e.g., at least 9%, 10%, 20%, 30% 40%, 50%, 60%, 70%, 80%, 90%, 95%, 98%, 99%, 99.9%, and 100%), by weight (excluding solvent), free from components that occur with it in nature or in an artificially produced mixture. Purity can be measured by any appropriate method, e.g., column chromatography, polyacrylamide gel electrophoresis, or HPLC analysis.

By "sequence identity" is meant the relatedness between two amino acid sequences or between two nucleotide sequences. Herein, the degree of identity between two amino acid sequences or two deoxyribonucleotide sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends in Genetics 16: 276-277; http://emboss.org), preferably version 3.0.0 or later. The optional parameters used are gap open penalty of 10, gap extension penalty of 0.5, and the EBLOSUM62 (EMBOSS version of BLOSUM62) substitution matrix for amino acid sequences or the EDNAFULL (EMBOSS version of NCBI NUC4.4) substitution matrix for nucleotide sequence. The output of Needle labeled "longest identity" (obtained using the -nobrief option) is used as the percent identity and is calculated as follows:

$$(\text{Identical Amino Acid of Nucleotide Residues} \times 100)/(\text{Length of Alignment} - \text{Total Number of Gaps in Alignment}).$$

Although methods and materials similar or equivalent to those described herein can be used in the practice or testing of the present invention, suitable methods and materials are described below. All patents, patent applications, and publications mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

FIG. 4 is the nucleic acid sequence SEQ ID NO:1.
FIG. 5 is the nucleic acid sequence SEQ ID NO:2.
FIG. 6 is the nucleic acid sequence SEQ ID NO:3.
FIG. 7 is the nucleic acid sequence SEQ ID NO:5.
FIG. 8 is the nucleic acid sequence SEQ ID NO:7.
FIG. 9 is the nucleic acid sequence SEQ ID NO:9.
FIG. 10 is the nucleic acid sequence SEQ ID NO:11.
FIG. 11 is the nucleic acid sequence SEQ ID NO:13.
FIG. 12 is the nucleic acid sequence SEQ ID NO:15.
FIG. 13 is the nucleic acid sequence SEQ ID NO:17.
FIG. 14 is the nucleic acid sequence SEQ ID NO:19.
FIG. 15 is the nucleic acid sequence SEQ ID NO:21.
FIG. 16 is the amino acid sequence SEQ ID NO:4.
FIG. 17 is the amino acid sequence SEQ ID NO:6.
FIG. 18 is the amino acid sequence SEQ ID NO:8.
FIG. 19 is the amino acid sequence SEQ ID NO:10.
FIG. 20 is the amino acid sequence SEQ ID NO:12.
FIG. 21 is the amino acid sequence SEQ ID NO:14.
FIG. 22 is the amino acid sequence SEQ ID NO:16.
FIG. 23 is the amino acid sequence SEQ ID NO:18.
FIG. 24 is the amino acid sequence SEQ ID NO:20.
FIG. 25 is the amino acid sequence SEQ ID NO:22.
FIG. 26 is the amino acid sequence SEQ ID NO:23.
FIG. 27 is the amino acid sequence SEQ ID NO:24.

DETAILED DESCRIPTION

Figure 1:
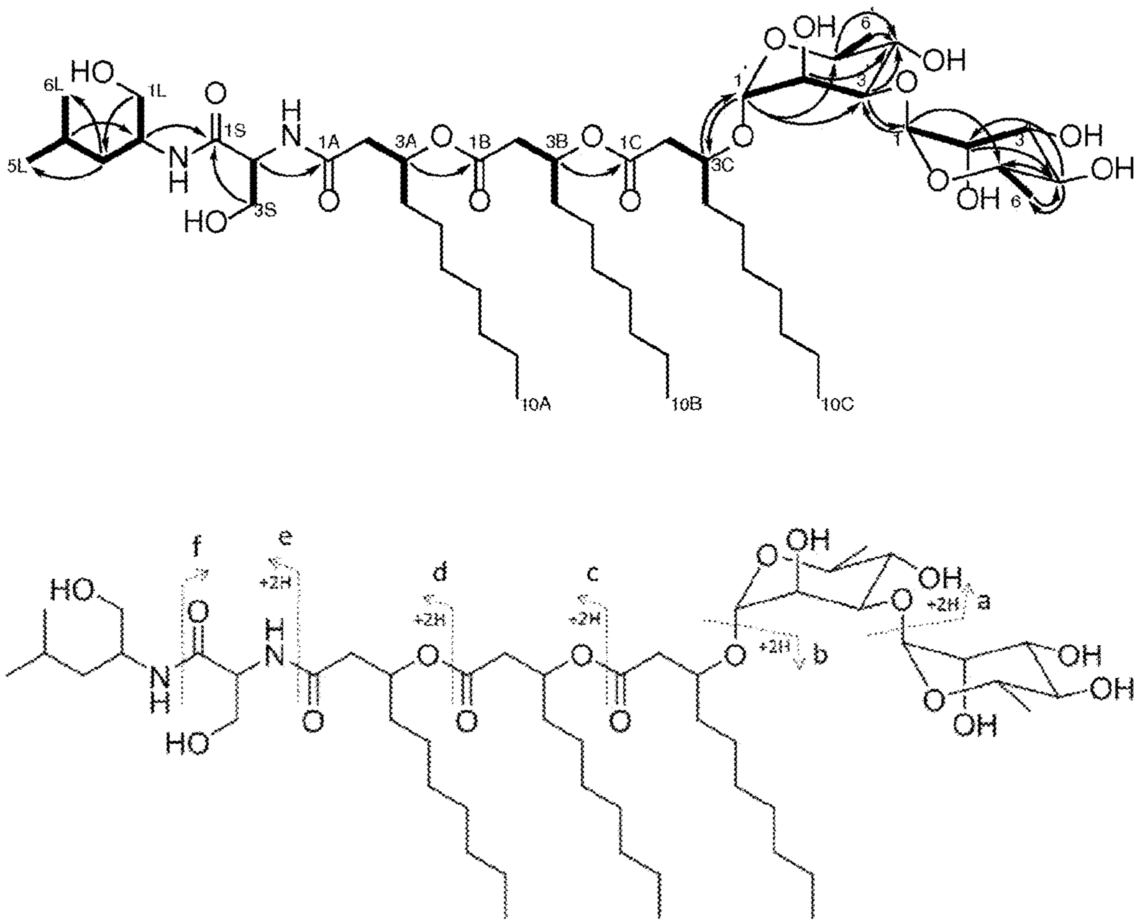
FIG. 1 is an illustration of selected HMBC ($^{1}H \rightarrow ^{13}C$) and COSY correlations (bold bonds) of NB-RLP1006 and assigned fragment ions from MS/MS collision-induced dissociation of the glycolipopeptides.

The invention encompasses glycolipopeptide surfactant compositions, methods of making and using such biosurfactants, and bacteria and bacterial culture that produce glycolipopeptides. The below described preferred embodiments illustrate adaptation of these compositions and methods. Nonetheless, from the description of these embodiments, other aspects of the invention can be made and/or practiced based on the description provided below.

General Methodology

Methods involving conventional organic chemistry, biochemistry, microbiology, and molecular biology are described herein. Such methods are described in, e.g., Clayden et al., Organic Chemistry, Oxford University Press, 1st edition (2000); Molecular Cloning: A Laboratory Manual, 2nd ed., vol. 1-3, Sambrook et al., ed., Cold Spring Harbor Laboratory Press, Cold Spring Harbor, N.Y., 2001; Current Protocols in Molecular Biology, Ausubel et al., ed., Greene Publishing and Wiley-Interscience, New York; and in the various volumes of Methods in Microbiology and Methods in Biochemistry and Molecular Biology both published by Elsevier.

Glycolipopeptides

Naturally occurring glycolipopeptides and synthetic analogues and derivatives thereof typically include a hydrophobic lipid component including a carboxyl end and a hydroxyl end, wherein the lipid component is covalently linked to (i) a peptide or peptide-like chain at the carboxyl end of the lipid component and (ii) a carbohydrate moiety at the hydroxyl end of the lipid component via a glycosidic linkage.

The peptide chain may comprise in the range of between 2 and 10 amino acids, preferably 2 to 8, more preferably 2 to 4 amino acids. The peptide chain may most preferably comprise 2 amino acids. The peptide or peptide-like chain can comprise and/or consist of a serine-leucinol dipeptide.

The lipid component may comprise in the range of between 1 and 6 alkanoic acid moieties, preferably 2 to 4, and more preferably 3. Most preferably the lipid component can include three β-hydroxyalkanoic acid moieties. The length of each acyl chain of the lipid component may be in the range of between $C_4$ to $C_{20}$, preferably $C_6$ to $C_{16}$, more preferably $C_8$ to $C_{14}$. Most preferably the length of each acyl chain may be selected from $C_8$, $C_{10}$, or $C_{12}$.

The carbohydrate moiety may be selected from saccharides including glucose, fructose, galactose, mannose, ribose, or deoxy saccharide variants including deoxyribose, fucose, or rhamnose. Preferably the carbohydrate moiety is rhamnose. In particular, a rhamnose moiety attached to the lipid component via a glycosidic linkage. In certain embodiments, the carbohydrate moiety can include one, two, or three rhamnose moieties and/or an acetyl groups. Preferably the carbohydrate moiety includes two.

Glycolipopeptides can include the structure:

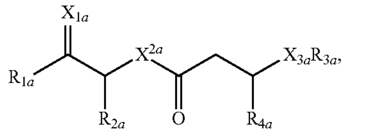

wherein $R_{1a}$ is H, OH, $OCH_3$, SH, $S(CH_3)$, $NH_2$, $NH(CH_3)$, $N(CH_3)_2$, or a peptide or peptide-like structure having the structure:

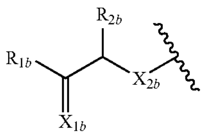

or

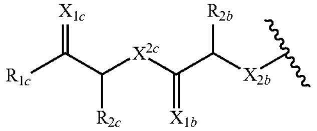

or

-continued

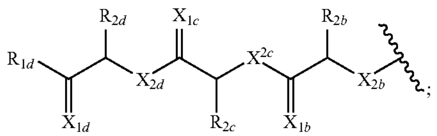

wherein $R_{1b}$, $R_{1c}$, and $R_{1d}$, are H, OH, $OCH_3$, SH, $S(CH_3)$, $NH_2$, $NH(CH_3)$, or $N(CH_3)_2$; $R_{2a}$, $R_{2b}$, $R_{2c}$, and $R_{2d}$ are each independently an amino acid side chain; $X_{1a}$, $X_{1b}$, $X_{1c}$, and $X_{1d}$ are each independently one oxygen atom or two hydrogen atoms; $X_{2a}$, $X_{2b}$, $X_{2c}$, and $X_{2d}$ are each independently NH, $N(CH_3)$, or O; $R_{3a}$ is a carbohydrate portion or a lipid monomer having the structure:

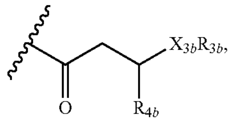

or a lipid oligomer having the structure of:

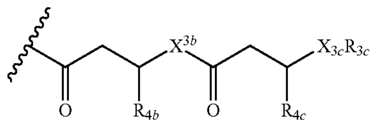

or

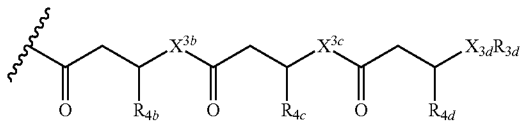

wherein $X_{3a}$, $X_{3b}$, $X_{3c}$, and $X_{3d}$ are each independently NH, $N(CH_3)$, or O; $R_{3a}$, $R_{3b}$, $R_{3c}$, and $R_{3d}$ includes a carbohydrate portion including a monomer having the structure:

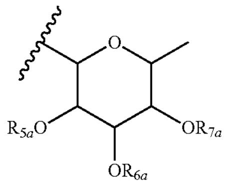

or

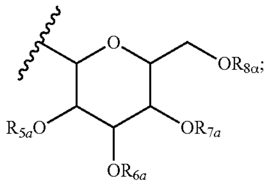

wherein $R_{5a}$, $R_{6a}$, $R_{7a}$, and $R_{8a}$ are each independently a hydrogen atom, methyl, acetyl, or a carbohydrate; and $R_{4a}$, $R_{4b}$, $R_{4c}$, and $R_{4d}$ are each independently a hydrogen atom, methyl, or a $C_2$ to $C_{19}$ saturated or unsaturated linear, branched-chain, cyclic, or aromatic hydrocarbon groups.

In the foregoing, at least one of $R_{6a}$, $R_{7a}$, and $R_{8a}$ can include a carbohydrate monomer having the structure:

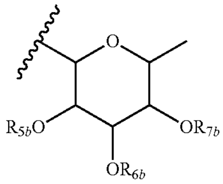

or

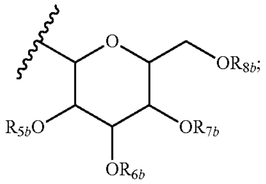

wherein $R_{5b}$, $R_{6b}$, $R_{7b}$, and $R_{8b}$ are each independently a hydrogen atom, methyl, acetyl, or a carbohydrate.

In certain embodiments the peptide or peptide-like portion includes at least one proline or proline-like monomer having the structure:

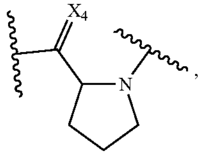

wherein $X_4$ is one oxygen atom or two hydrogen atoms, or a single proline or proline-like monomer or a terminal proline or proline-like monomer having the structure:

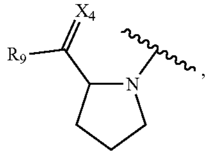

wherein $R_9$ is of H, OH, $OCH_3$, SH, $S(CH_3)$, $NH_2$, $NH(CH_3)$, or $N(CH_3)_2$; and $X_4$ is one oxygen atom or two hydrogen atoms.

Glycolipopeptides can have the following structures:

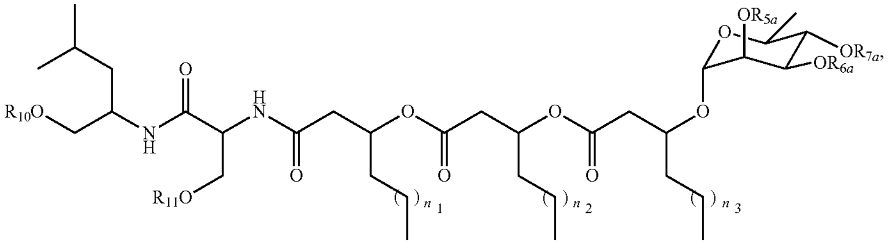

wherein $R_{5a}$, $R_{6a}$, $R_{7a}$, $R_{10}$, and $R_{11}$ are each independently a hydrogen atom or acetyl; and $n_1$, $n_2$, and $n_3$ are integers each independently ranging from 1 to 7;

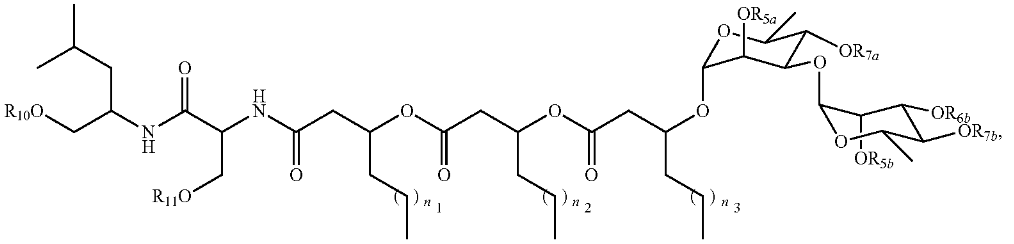

wherein $R_{5a}$, $R_{5b}$, $R_{6b}$, $R_{7a}$, $R_{7b}$, $R_{10}$, and $R_{11}$ are each independently a hydrogen atom or acetyl; and $n_1$, $n_2$, and $n_3$ are integers each independently ranging from 1 to 7;

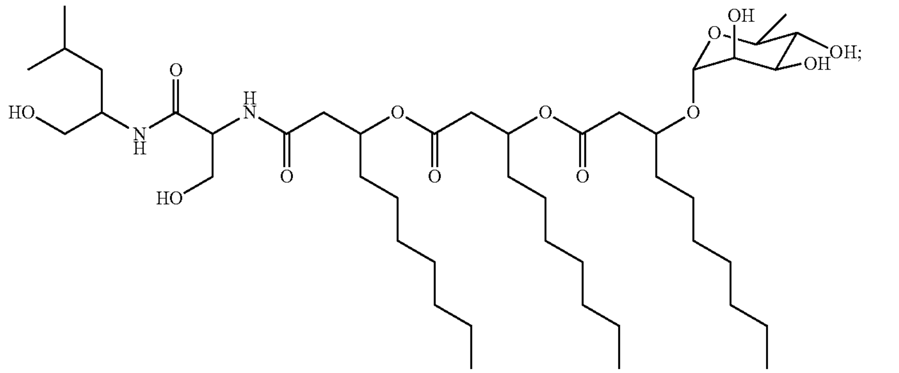

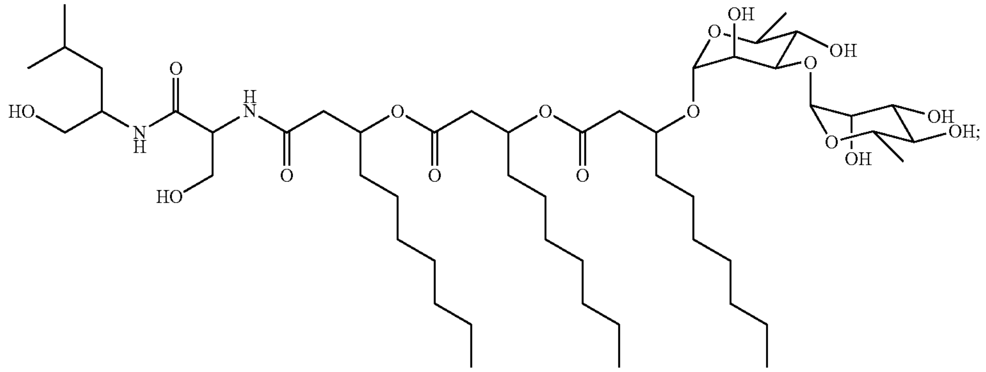

or

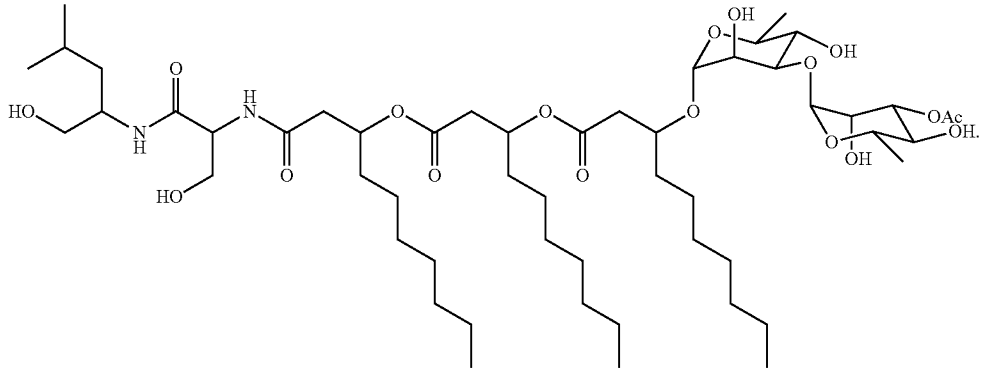

Derivatives, analogues, and other variants of the foregoing glycolipopeptides can be made by one of skill in the art. For instance, the amino acid composition and length of the peptide chain could be modified in a combinatorial fashion, introducing either proteinogenic or unnatural amino acids to modulate the solubility, hydrophilic-lipophilic balance (HLB), and other surfactant characteristics of the glycolipopeptides. The peptide portion may also contain amino acids with charged functional groups, which may result in cationic, anionic, or zwitterionic surfactants with unique surfactant applications. The carboxylic acid functionality at the C-terminus position of the peptide may also be reduced to a primary hydroxyl group. Similarly, the lipid portion may contain various numbers (e.g., 1, 2, 3, 4 or more) of β-hydroxyalkanoate units, which themselves may be comprised of $C_2$ to $C_{19}$ saturated or unsaturated linear, branched-chain, cyclic, or aromatic hydrocarbon groups. The rhamnose moieties could be linked together via 1,2-, 1,3-, or 1,4-glycosidic linkages, which may possess either the α- or β-configuration. In addition to rhamnose, the carbohydrate portion may also be composed of glucose or other monosaccharide units.

Variants of the *Variovorax paradoxus* RKNM-096 glycolipopeptide biosurfactants that have altered properties could be made. Altered properties of such variants may include, but are not limited to, alterations in emulsification, foaming and surface tension reducing properties exhibited under differing physiochemical conditions such as, but not limited to, temperature, pH, and salinity.

The variovaricins describe herein may be at least 5, 10, 20, 30, 40, 50, 60, 70, 80, 90, 95, 99, 99.5, 99.9, or 99.99 percent purified (by weight). They may be in crystalline or non-crystalline (amorphous) form, and in some cases also be obtained as salts derived from such organic and inorganic acids as: acetic, trifluoroacetic, lactic, citric, tartaric, formate, succinic maleic, malonic, gluconic, hydrochloric, hydrobromic, phosphoric, nitric, sulfuric, methane sulfonic and similarly known acids. The salts can be prepared by adapting commonly known procedures.

In some embodiments, the composition includes additional compounds such as carriers, other surfactants (e.g., non-glycolipopeptide surfactants), or biologically active compounds (non-glycolipopeptide surfactants, such as pharmaceutical agents or other non-glycolipopeptide antimicrobial agents). The addition of the aforementioned agents to glycolipopeptide surfactants can be selected by one skilled in the art based on the chosen application.

The composition can include a carrier, such as conventional pharmaceutically acceptable carriers as described in *Remington: The Science and Practice of Pharmacy*, The University of the Sciences in Philadelphia, Editors, Lippincott, Williams, & Wilkins, Philadelphia, Pa., $21^{st}$ Edition (2005).

Pharmaceutically acceptable carriers vary depending on the mode of administration. Fluid formulations used for parenteral injection may include fluids such as water, physiological saline, aqueous dextrose or glycerol. Solid formulations may include highly purified solid carriers such as magnesium stearate, starch, or lactose. Pharmaceutical compositions may also contain minor quantities of non-toxic auxiliary substances, such as buffers and preservatives.

In some embodiments, the compositions include a non-glycolipopeptide surfactant. Examples include non-ionic, cationic, anionic and amphoteric surfactants. Representative examples of anionic surfactants include carboxylates, sulfonates, petroleum sulfonates, alkylbenzene sulfonates, naphthalene sulfonates, olefin sulfonates, alkyl sulfates, sulfates, sulfated natural oils and fats, sulfated esters, sulfated alkanolamides, alkylphenols, ethoxylated and sulfated aklylphenols and rhamnolipids. Examples of cationic surfactants include quaternary ammonium salts, N, N, N', N' tetrakis substituted ethylenediamines and 2-alkyl-1-hydroxethyl-2-imidazolines. Examples of non-ionic surfactants include ethyoxylated aliphatic alcohols, polyoxyethylene surfactants, carboxylic esters, polyethylene glycol esters, anhydrosorbitol ester and ethoxylated derivatives, glycol esters of fatty acids, carboxylic amides, monoalkanolamine condensates and polyoxyethylene fatty acid amides. Examples of amphoteric surfactants include sodium salts of N-coco-3-aminopropionic acid, N-tallow-3-iminodipropionate and N-cocoamidethyl-N-hydroxyethylglycine, as well as N-carboxymethyl-N-dimethyl-N-(9-octadecenyl) ammonium hydroxide. In further embodiments, the composition includes one or more food or food additive, cosmetic or pharmaceutical agents or antimicrobial agents (such as an antibacterial or antifungal agents).

Methods of Making Glycolipopeptides

The glycolipopeptides described herein may be made by isolation or purification from bacteria strains which produce them, such as *Variovorax paradoxus* RKNM-096. As described in the Examples section below, bacteria which produce one or more glycolipopeptides can be isolated from natural habitats or obtained from publicly accessible sources. Bacteria can be determined to produce glycolipopeptides by the methods described in the Examples. The glycolipopeptide-producing bacterium can be placed in a bioreactor (vessel) containing suitable culture medium, and then incubated under conditions that promote bacterial replication and production of one or more glycolipopeptides. The produced glycolipopeptide(s) can be purified or isolated from the culture mixture by conventional techniques such as extraction followed by chromatographic separation (e.g., using ultra high performance liquid chromatography). Chemical analyses (determination of molecular weight, melting point, NMR, IS spectroscopy, etc.) can be performed to confirm the structure and purity of the isolated glycolipopeptide(s). Alternatively, the glycolipopeptides described herein may be made by total synthesis or semi-synthesis, e.g. as described herein.

Glycolipopeptides Gene Clusters and Methods of Use

As described in Example 7 below, the glycolipopeptide and rhamnose biosynthetic gene clusters of *V. paradoxus* RKNM-096 were characterized. The polypeptides encoded in the gene cluster function in a coordinated fashion to synthesize the NB-RLP series of biosurfactants. The nucleotide sequence encoding these genes and the amino acid sequences of the corresponding polypeptides are shown in the sequence listing. Other amino acid sequences and the nucleic acid sequences that share at least 70% (e.g., at least 70, 80, 90, 95, 97, 98, or 99%) sequence identity with those shown in the sequence listing might also be used in the methods and compositions described herein particularly when such other sequences exhibit (or encode a molecule exhibiting) at least 50% (e.g., at least 50, 60, 70, 80, 90, or 100%) of the corresponding native polypeptide enzymatic activity. Nucleic acid sequences which encode the same polypeptides described herein but are not included in the sequence listing might also be used.

The foregoing polynucleotides might be used in a method for producing recombinant biosynthetic enzymes. As one example, such a method might include culturing a host cell (e.g., *E. coli* or another suitable prokaryotic or eukaryotic host cell) which contains an expression vector having a nucleic acid sequence of one or more of SEQ ID NO:1, SEQ ID NO:2, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19 and SEQ ID NO:21 in a culture medium under conditions suitable for expression of the recombinant protein in the host cell, and b) isolating the recombinant protein(s) from the host cell or the culture medium.

Also contemplated is method of producing a glycolipopeptide in a heterologous host cell by expressing the complete or partial biosynthetic gene cluster. This method might include the steps of a) culturing a host cell which contains an expression vector having nucleic acid sequences comprising SEQ ID NO:1, SEQ ID NO:2, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19 and SEQ ID NO:21 in a culture medium under conditions suitable for expression of the recombinant proteins in the host cell, and b) isolating produced glycolipopeptides from the culture medium.

Further contemplated are methods for using a nucleic acid molecule that hybridizes to or includes a portion of SEQ ID NO:1, SEQ ID NO:2, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19 or SEQ ID NO:21 as a probe or PCR primer to identify other organisms capable of producing glycolipopeptides or structurally similar biosurfactants.

Synthesis

The compounds of the present invention may be achieved using chemical methods as noted herein.

The total synthesis of the glycolipopeptides can be achieved using established synthetic methodology to assemble commercially available building blocks. A retrosynthetic analysis of NB-RLP1006 (1) demonstrates the feasibility of the total synthesis. As an example, one skilled in the art of organic synthesis may couple the dipeptide substituent (4) to the tridecanoic acid (5) and perform a chemical glycosylation of the lipopeptide intermediate (2) using glycosyl donor 3 as shown below. The dipeptide moiety can be prepared using standard amide coupling methods, while the tridecanoic acid can be generated from commercially available ethyl trans-2-decenoate. Meanwhile, the α-1,3-linked dirhamnose substituent (3) can be assembled using glycosyl donor 6 and glycosyl acceptor 7. It is understood that this general approach, or other similar sequence of protecting group manipulations can provide p-methoxyphenyl 2,4-di-O-benzyloxyrhamnopyranoside (10) (Cai, X.; et al. Carbohydr. Res. 2010, 345, 1230), which can be glycosylated at the 3-OH position to achieve the α-1,3 glycosidic linkage between the two rhamnose substituents. The anomeric effect is expected to direct the formation of an α-glycosidic linkage with high stereoselectivity in this chemical glycosylation (Takahashi, O.; et al. Carbohydr. Res. 2007, 342, 1202).

Scheme 2. Synthesis of rhamnosyl donor 9 and glycosyl aceptor 10 as building blocks for the assembly of the dirhamnose substituent.

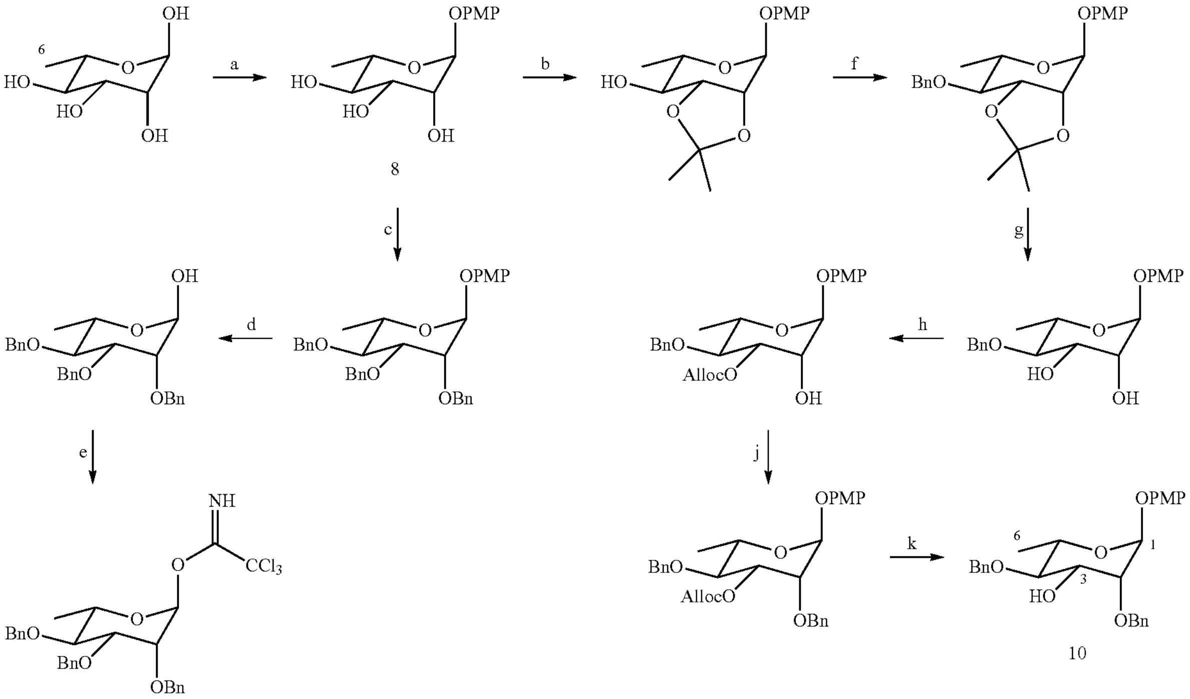

8

9

10

Reagents and conditions: (a) (i) $Ac_2O$, pyridine, 70° C., 16 h. (ii) p-methoxyphenol, $BF_3$•$Et_2O$, $CH_2Cl_2$, 0° C. → 25° C., 3 h. (iii) $NaOCH_3$, $CH_3OH$. (b) $CH_3C(OCH_3)_2CH_3$, DMF, TsOH•$H_2O$. (c) BnBr, $Bu_4NI$, NaH, DMF, 0° C. → 25° C., 3 h. (d) 80% $CH_3CN$, CAN, 35° C., 30 min. (e) $CCl_3CN$, DBU, $CH_2Cl_2$, 25° C., 30 min. (f) BnBr, $Bu_4NI$, NaH, DMF, 0° C. → 25° C., 3 h. (g) 70% AcOH, 70° C., 3 h. (h) AllocCl, pyridine, DMF, $CH_2Cl_2$, -15° C. → 0° C., 3 h. (j) BnBr, $Bu_4NI$, NaH, DMF, 0° C. → 25° C., 3 h. (k) $NaBH_4$, $Pd[P(C_6H_5)_3]_4$, $CH_3COONH_4$, $CH_3OH$:THF (1:1), -5° C., < 30 min.

approaches in which one assembles commercially available starting materials, could enable the synthesis of glycolipopeptide analogues. For instance, different amino acids can be incorporated into the peptide or peptide-like portion while the length of the peptide chain can be increased or decreased. Similarly, structural modifications could be made to the lipid and carbohydrate portions of the glycolipopeptides to produce analogues with potentially useful biosurfactant characteristics.

To generate the carbohydrate substituent, α-1,3 linked dirhamnose, a number of protecting group manipulations must be performed to enable regioselective glycosylation of the rhamnose sugar at the 3-OH position (Scheme 2). The p-methoxyphenyl α-L-rhamnopyranoside (8), which serves as a synthetic precursor to both rhamnose moieties, can be synthesized from commercially available L-rhamnose in three steps. The terminal rhamnose sugar can then be prepared by perbenzylation of 8 and removal of the p-methoxyphenyl substituent to allow synthesis of the rhamnosyl trichloroacetimidate (9). Meanwhile, a six-step To assemble the dirhamnose substituent, glycosyl donor 9 can be linked to glycosyl acceptor 10 through activation of the anomeric trichloroacetimidate using either $BF_3$·$Et_2O$ or TMSOTf (Scheme 3). The anomeric p-methoxyphenyl protecting group must then be replaced with a good leaving group, such as a trichloroacetimidate, to enable glycosylation of the decanoic acid moiety. Alternatively, a thiophenyl group could be installed instead of the p-methoxyphenyl group during reaction A of Scheme 2. This approach would allow an orthogonal glycosylation to be pursued given the dual role of the anomeric thiophenyl group as a protecting and leaving group (Gampe, C. M.; et al. Tetrahedron 2011, 67, 9771; Wu, C.-Y.; Wong, C.-H. Top. Curr. Chem. 2011, 301, 223). It is known that the total synthesis of NB-RLP860 could be achieved using rhamnosyl donor 9 or other suitable rhamnosyl donors. Furthermore, it is recognized that a skilled chemist could modify the carbohydrate moiety of the glycolipopeptides by using glycosyl donors other than 9, 11, or 12.

Scheme 3. Synthesis of 11 and 12 as glycosyl donors for the glycosylation of the tridecanoic acid moiety.

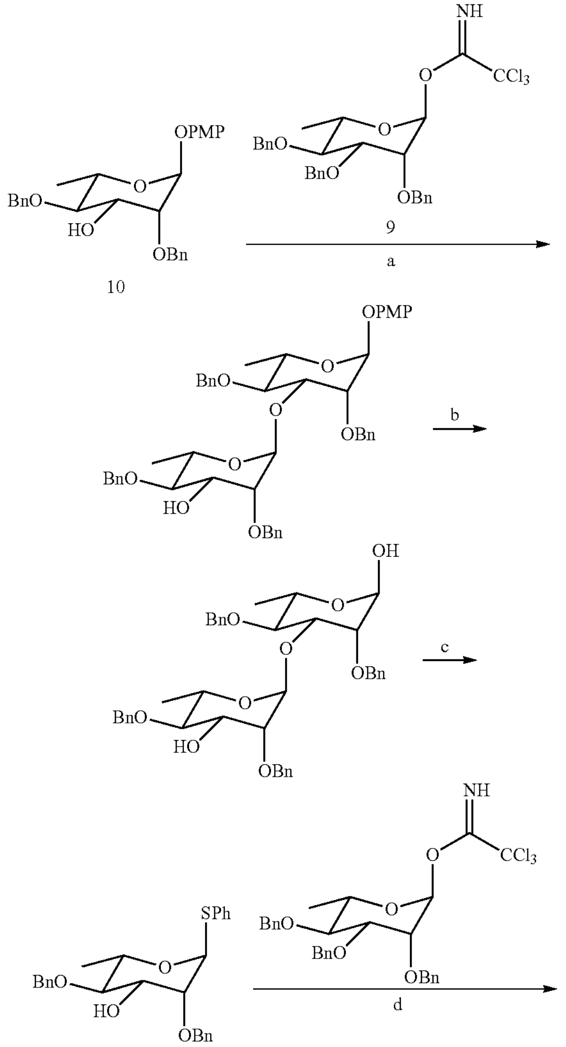

9

10

-continued

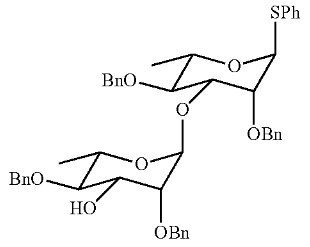

12

Reagents and conditions: (a) $BF_3 \cdot Et_2O$ (cat.), 9, anhydrous $CH_2Cl_3$, 3Å molecular sieves, -78° C., 2 h. (b) 80% $CH_3CN$, CAN, 35° C., 30 min. (c) $CCl_3CN$, DBU, $CH_2Cl_2$, 25° C., 30 min. (d) $BF_3 \cdot Et_2O$ (cat.), 9, anhydrous $CH_2Cl_2$, 3Å molecular sieves, -78° C., 2 h.

To assemble the tridecanoic acid moiety, commercially available ethyl trans-2-decenoate (13) can serve as a precursor to the synthesis of 3-hydroxydecanoic acid (14) through an established five-step β-oxidation (Schneekloth, J. S.; et al. Bioorg. Med. Chem. Lett. 2006, 16, 3855; Pandey, S. K.; Kumar, P. Eur. J. Org. Chem. 2007, 369). Overall yields reported in the literature for this synthesis vary between 50-85% (Scheme 4). Although (±)-3-hydroxydecanoic acid is also commercially available, this racemic precursor is cost-prohibitive and does not likely represent an economically viable route. Upon generating the 3-(tert-butyldimethylsilyl) decanoic acid (15), this building block can be linked twice to 14 via Steglich esterification to generate the silylated di- and tri-decanoic acid (16 and 17, respectively) of NB-RLP1006 and other glycolipopeptides. In this approach, carboxylic acid 15 is activated as a N-hydroxysuccinimide ester prior to the addition of 14, obviating an additional protecting group for the carboxylic acid functionality of 14.

Scheme 4. Synthesis of tridecanoic acid moiety (17) of NB-RLP1006.

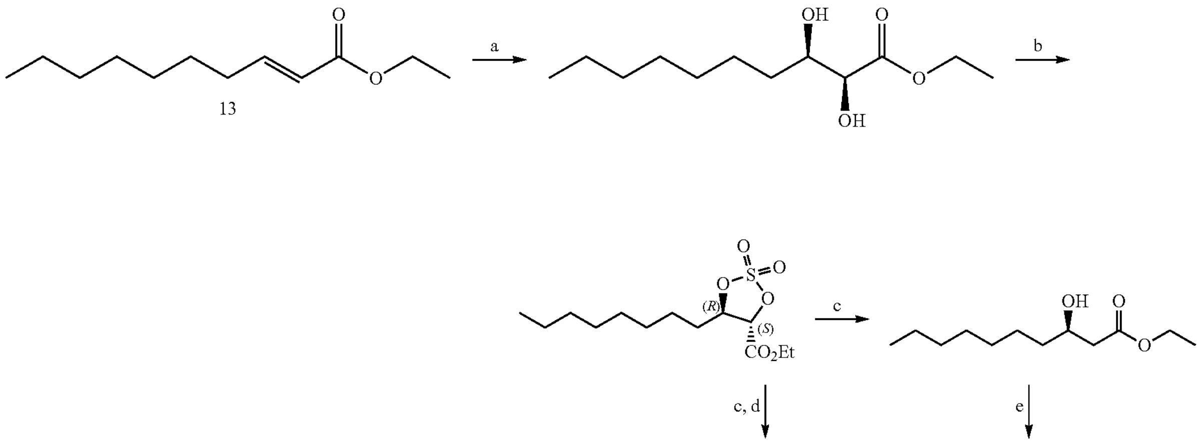

13

-continued

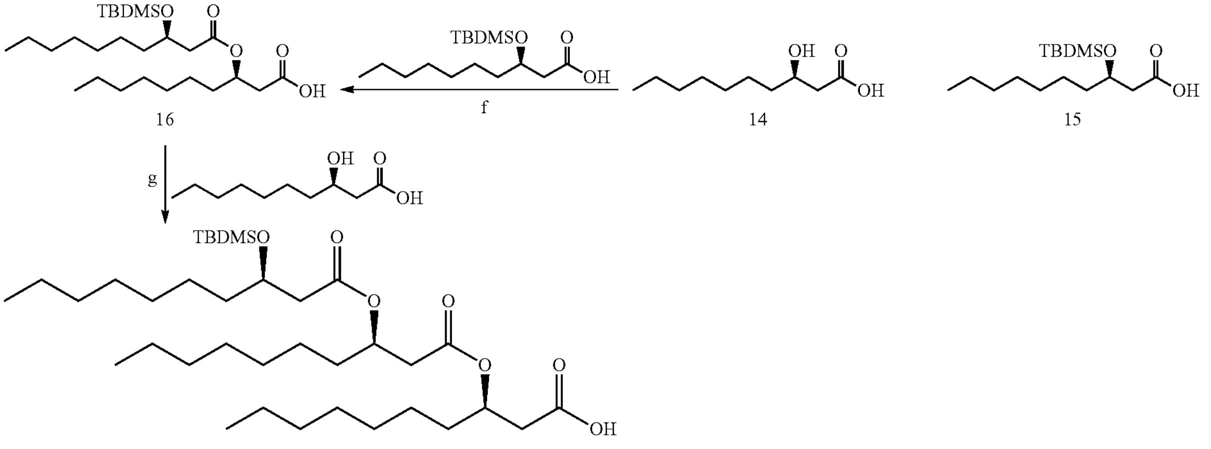

17

Reagents and conditions: (a) $(DHQD)_2PHAL$ (1 mol%), 0.1M $OsO_4$ (0.5 mol%), $K_2CO_3$, $K_3Fe(CN)_6$, $CH_3SO_2NH_2$, t-BuOH:$H_2O$ (1:1), 0° C., 24 h. (b) (i) $SOCl_2$, $Et_3N$, $CH_2Cl_2$, 0° C., 30 min. (ii) $RuCl_3$, $NaIO_4$, $CCl_4$:$CH_3CN$:$H_2O$ (2:2:3), 0° C., 1 h. (c) $NaBH_4$, DMAC, 25° C., 30 min. (d) NaOH, Acetone:$H_2O$ (1:1), 25° C., 16-24 h. (e) (i) TBDMSCl, imidazole, DMF, 25° C. (ii) NaOH, Acetone:$H_2O$ (1:1), 25° C., 16-24 h. (f) (i) 3-benzyloxydecanoic acid, DIC, NHS, 0° C. → 25° C., 3 h. (ii) 3-hydroxydecanoic acid, $Et_3N$, DMAP, 25° C., 3 h. (g) (i) 3-(3-(benzyloxy)decanoyloxy) decanoic acid, DIC, NHS, 0° C. → 25° C., 3 h. (ii) 3-hydroxydecanoic acid, $Et_3N$, DMAP, 25° C., 3 h.

An alternative approach is also available in which the carboxylic acid group of 14 is protected as a benzyl ester before esterification (Scheme 5). In this approach, building blocks 15 and 18 are linked together in a synthesis that requires additional steps for installing and removing silyl ether and benzyl ester protecting groups. It is known that a chemist skilled in the art of organic synthesis could utilize either approach to introduce $C_2$ to $C_{19}$ saturated or unsaturated linear, branched-chain, cyclic, or aromatic hydrocarbon moieties in order to modify the lipid portion of the glycolipopeptides. It is anticipated that analogues generated through this approach may also exhibit surfactant properties.

Scheme 5. Alternative route to the tridecanoic acid moiety (17) of NB-RLP1006.

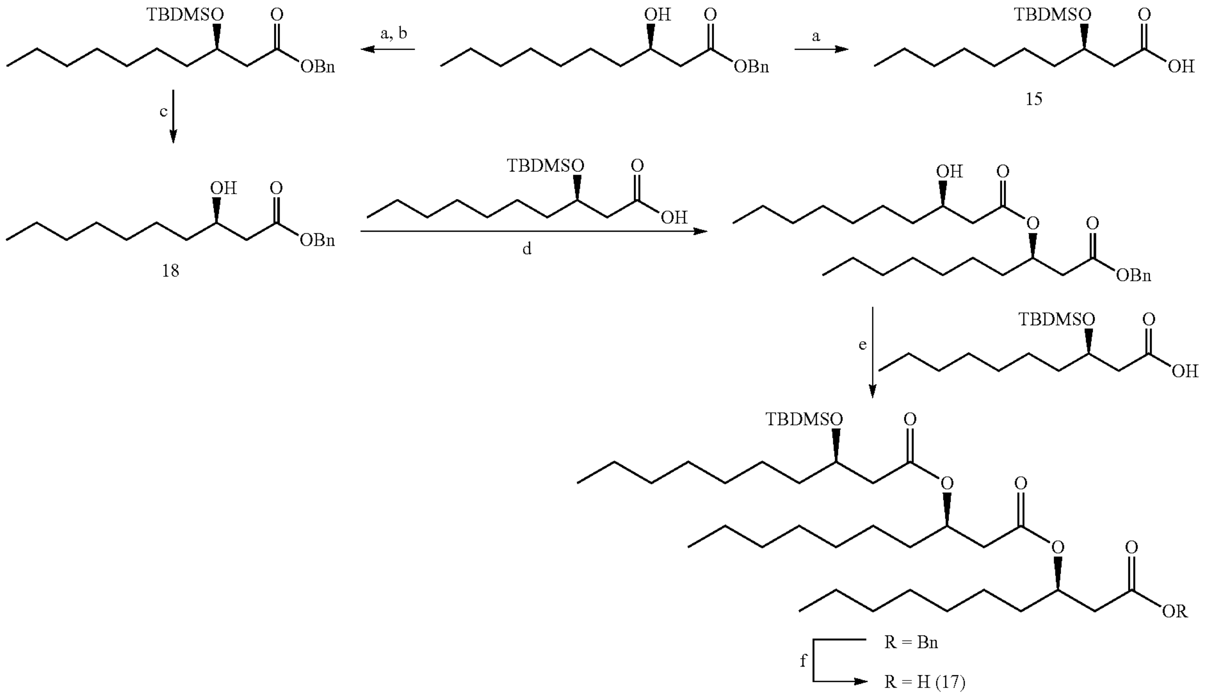

Reagents and conditions: (a) (i) TBDMSCl, imidazole, DMF, 25° C. (ii) NaOH, Acetone:$H_2O$ (1:1), 25° C., 16-24 h. (b) (i) DIC, NHS, 0° C. → 25° C., 3 h. (ii) BnOH, $Et_3N$, DMAP, 25° C., 3 h. (c) $Bu_4NF$, THF, 25° C., 3 h. (d) (i) 3-(tert-butyldimethylsilyloxy)decanoic acid (15), DIC, NHS, 0° C. → 25° C., 3 h. (ii) benzyl 3-hydroxydecanoate (18), $Et_3N$, DMAP, 25° C., 3 h. (e) (i) $Bu_4NF$, THF, 25° C., 3 h. (ii) 3-(tert-butyldimethylsiloxy)decanoic acid (15), DIC, NHS, 0° C. → 25° C., 3 h. (iii) benzyl 3-(3-hydroxydecanoyloxy)decanoate, $Et_3N$, DMAP, 25° C., 3 h. (f) 10% Pd/C (20 wt%), $H_2$, $CH_2Cl_2$, 25° C., 16 h.

The leucinol-serine dipeptide can be assembled from commercially available Boc-leucinol (19) and Fmoc-Ser (Bzl)-OH (20) using well-established amide coupling chemistry (Scheme 6) (Valeur, E.; Bradley, M. Chem. Soc. Rev. 2009, 38, 606). The five-step reaction sequence involves protecting the primary hydroxyl group of 19 as a benzyl ether and coupling the two amino acids before removing the 9-fluorenylmethyloxycarbonyl (Fmoc) protecting group to generate the leucinol-serine dipeptide (21) that is poised for amide coupling to the decanoic acid. It is conceivable that other commercially available amino acids, including but not limited to D-amino acids and β-amino acids, could be assembled in a similar fashion to introduce structural modifications at the peptide portion of the glycolipopeptide. The C-terminus of the peptide or peptide-like portion could exist as a carboxylic acid functionality or be reduced to a primary hydroxyl group. Other modifications of the C-terminus position include, but are not limited to, alkylation, acylation, glycosylation, phosphorylation, and sulfation. The chain length of the peptide or peptide-like portion could be increased by coupling additional amino acid monomers to the dipeptide intermediate. Alternatively, a single amino acid monomer could be coupled to the tridecanoic acid intermediate (17) to decrease the chain length.

Scheme 6. Preparation of the leucinal-serine dipeptide residue of NB-RLP1006.

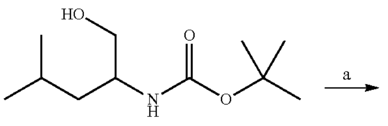

19

-continued

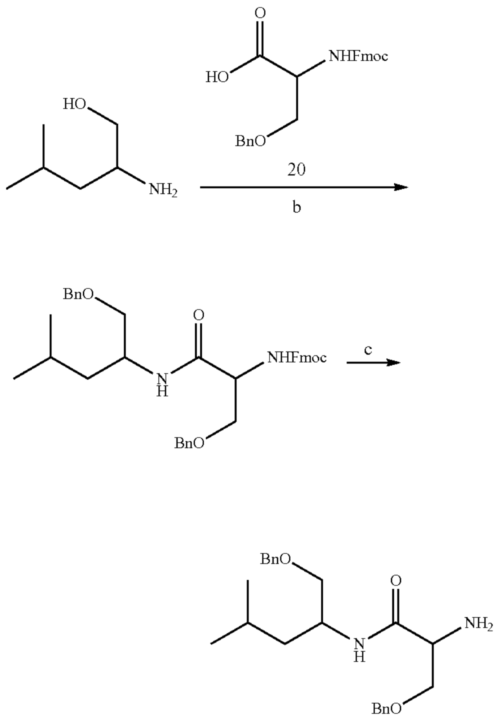

21

Reagents and conditions: (a) (i) BnBr, $Bu_4NI$, NaH, DMF, 0° C. → 25° C., 3 h. (ii) HCl, $CH_3OH$, 25° C., 1 h. (b) (i) Fmoc-Serine(Bzl)—OH, DIC, NHS, 0° C. → 25° C., 3 h. (ii) Leucinol(Bzl), $Et_3N$, DMAP, 25° C., 3 h. (c) Piperidine (20 vol%), DMF, 25° C., 3 h.

The tridecanoic acid (17) can readily undergo amide coupling to the benzylated dipeptide (21), upon which the tert-butyldimethyl silyl ether protecting group can be removed using tetrabutylammonium fluoride to provide glycosyl acceptor 22 (Scheme 7). Glycosylation of 22 with either 11 or 12, followed by global deprotection via hydrogenolysis of the benzyl ethers, furnishes the deprotected glycolipopeptide NB-RLP1006.

Scheme 7.

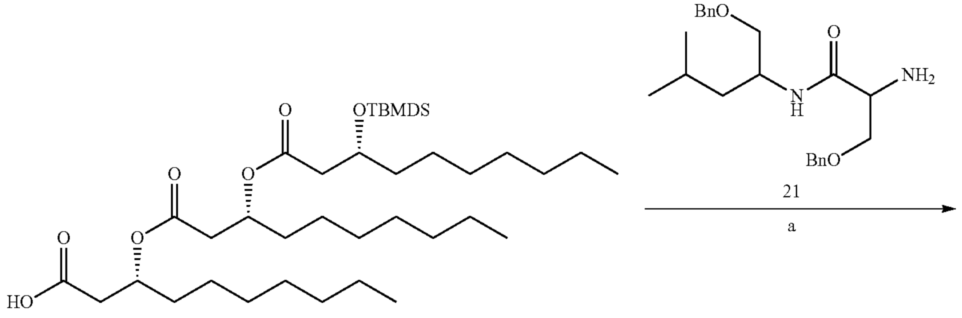

17

-continued

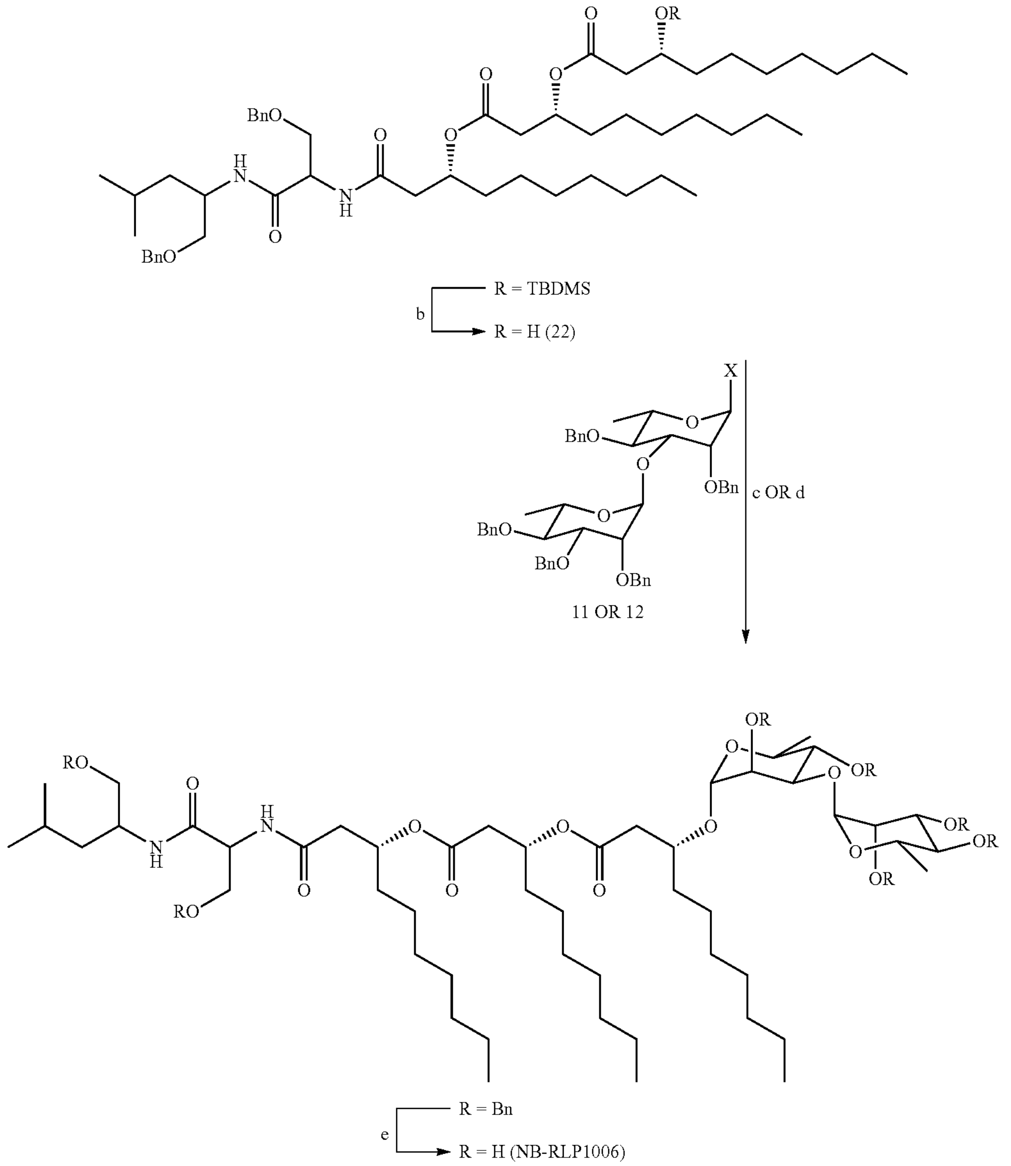

Final steps in the assembly of the glycolipopeptide NB-RPL1006. Reagents and conditions:
(a) (i) DIC, NHS, 0° C. → 25° C., 3 h. (ii) Leucinol(Bzl)-Ser(Bzl)$NH_2$ (21), $Et_3N$, DMAP, 25° C., 3 h.
(b) $Bu_4NF$, THF, 25° C., 3 h.
(c) If glycosyl donor 11 (X = $CNHCl_3$), $BF_3$•$Et_2O$ (cat.), 3 Å molecular sieves, anhydrous $CH_2Cl_2$, -78° C., 2 h.
(d) If glycosyl donor 12 (X = SPh), NIS, TfOH (10 mol %), 1,2-DCE, 4 Å molecular sieves.
(e) 10% Pd/C (20 wt %), $H_2$, $CH_2Cl_2$, 25° C., 16 h.

Although the total synthesis of NB-RLP1006 may require between 14-18 steps (longest linear sequence, 34-40 steps total), the synthesis could be expedited by utilizing solid-phase synthetic techniques in which the terminal leucinol residue is immobilized onto a solid support. For example, the Leucinol(Bzl) (19) can be tethered to a polystyrene-bound p-alkoxybenzyl hydroxyl group (Wang resin) through a silyl ether linkage (Scheme 8) (Scott, P. J. H. Linker Strategies in Solid-Phase Synthesis, John Wiley & Sons Ltd: Chichester, U.K., 2009; pp 50-51). Following previously described amide coupling and Steglich esterification methodologies (Coin, I.; et al. Nat. Protoc. 2007, 2, 3247.), the remaining serine and decanoic acid residues can then be attached in a step-wise approach using Fmoc-Ser(Bzl)-OH (20) and 3-(tert-butyldimethylsilyl)decanoic acid (23). After releasing the lipopeptide intermediate, the primary hydroxyl group can be selectively protected as a tert-butyldiphenylsilyl ether to provide glycosyl acceptor 24. The glycolipopeptide NB-RLP1006 can then be synthesized by chemical glycosylation and removal of the silyl and benzyl ether protecting groups. Analogues of the glycolipopeptides can also be produced using solid-phase synthetic techniques as described in the foregoing solution-phase synthesis of NB-RLP1006.

Scheme 8. Solid-phase total synthesis of NB-RLP1006.

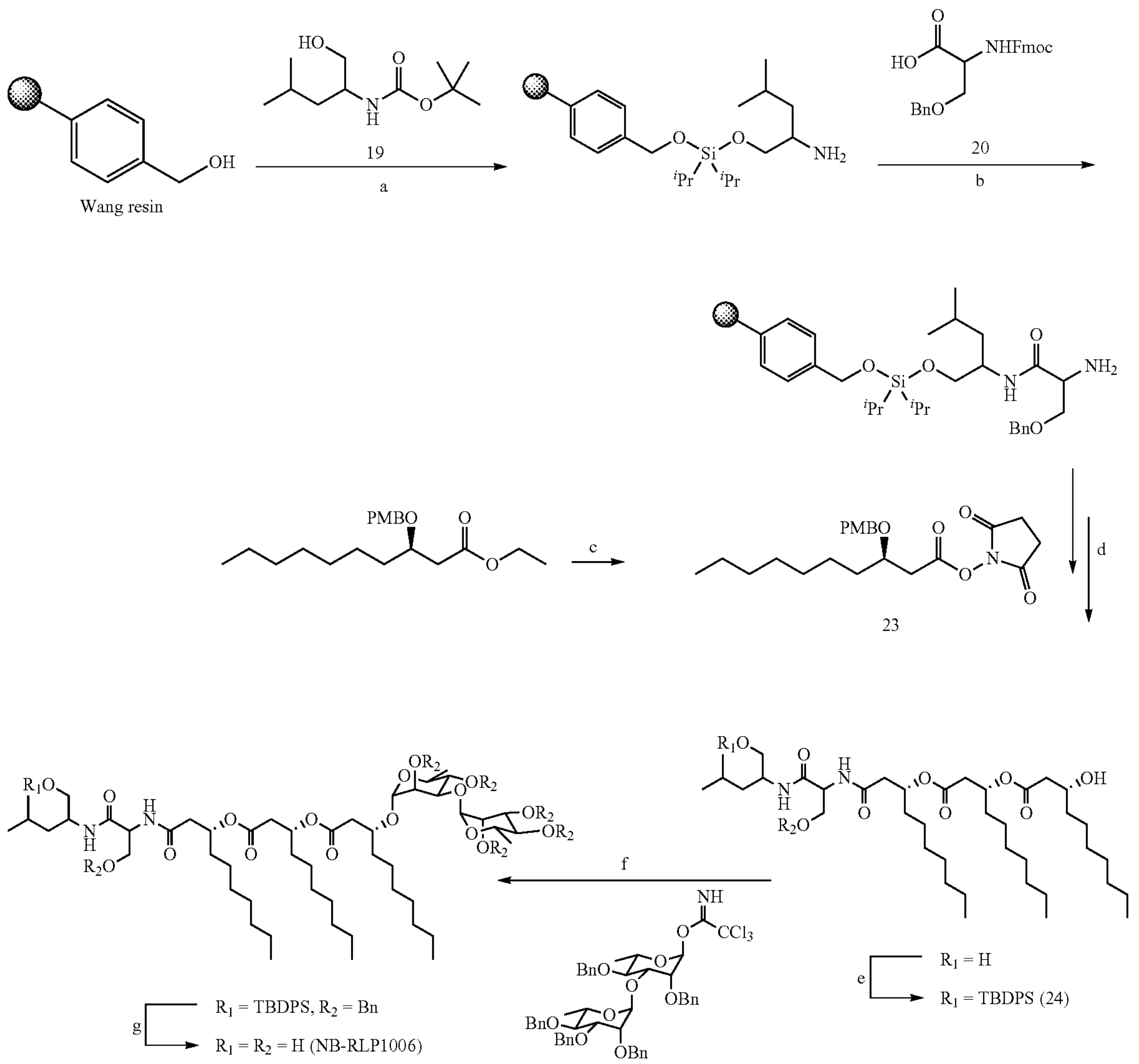

11

Reagents and conditions:

(a) (i) Leucinol(Bzl) (19), $^{i}Pr_2SiCl_2$, imidazole, DMF, 25° C., 1 h. (ii) HCl, $CH_3OH$, 25° C., 1 h.25° C., 3 h. (ii) $Et_3N$, DMAP 25° C., 3 h. (c) (i) PMBCl, NaH, DMF, 0° C. →
(b) (i) Fmoc-Serine(Bzl)—OH (20), DIC, NHS, 0° C. → 25° C., 3 h. (ii) NaOH, Acetone:$H_2O$ (3:1), 25° C., 16-24 h.
(iii) DIC, NHS, 0° C. → 25° C., 3 h. (d) (i) 23, $Et_3N$, DMAP, 25° C., 3 h. (ii) 80% $CH_3CN$, CAN, 35° C., 30 min. (iii) 23, $Et_3N$, DMAP, 25° C., 3 h.
(iv) 80% $CH_3CN$, CAN, 35° C., 30 min, (v) 23, $Et_3N$, DMAP, 25° C., 3 h.
(vi) 80% $CH_3CN$, CAN, 35° C., 30 min. (vii) $Bu_4NF$, THF, 25° C., 3 h.
(e) TBDPSCl, imidazole, DMAP, DMF, 25° C., 2 h. (f) $BF_3$•$Et_2O$ (cat.), anhydrous $CH_2Cl_2$, -78° C., 2 h.
(g) (i) $Bu_4NF$, THF, 25° C., 3 h. (ii) 10% Pd/C (20 wt%), $H_2$, $CH_2Cl_2$, 25° C., 16 h.

Semisynthesis of the Glycolipopeptides

Synthetic analogues of NB-RLP1006 and other glycolipopeptides may also be of interest for assessing the structure-activity relationships of this class of biosurfactants. Unlike the total synthesis, a semisynthesis could represent a rapid approach for developing a number of glycolipopeptide analogues. For instance, strategies may involve a semisynthesis of the tridecanoic acid (23) by acid hydrolysis of the glycolipopeptide mixture (Scheme 9). See Miao, S.; et al. J. Agric. Food Chem. 2015, 63, 3367. Tridecanoic acid (23) could then be coupled to the peptide portion and glycosylated with commercially available disaccharides, such as lactose or maltose, to generate novel glycolipopeptide analogues (e.g. 24). The aglycone of glycolipopeptides may also be produced by *V. paradoxus* RKNM-096 and undergo chemical glycosylation to produce similar analogues. It is also known that the rhamnolipids could be utilized as an advanced precursor and linked to various dipeptides (e.g. 21) through the carboxylic acid functional group to produce glycolipopeptides similar to NB-RLP1006 (Scheme 10). Given the commercial availability of the rhamnolipids, conceivably one skilled in the art of organic synthesis would also recognize that peptide chains other than leucinol-serine could be introduced to expand on the structural diversity of glycolipopeptide analogues accessible through this semisynthetic approach.

Scheme 9.
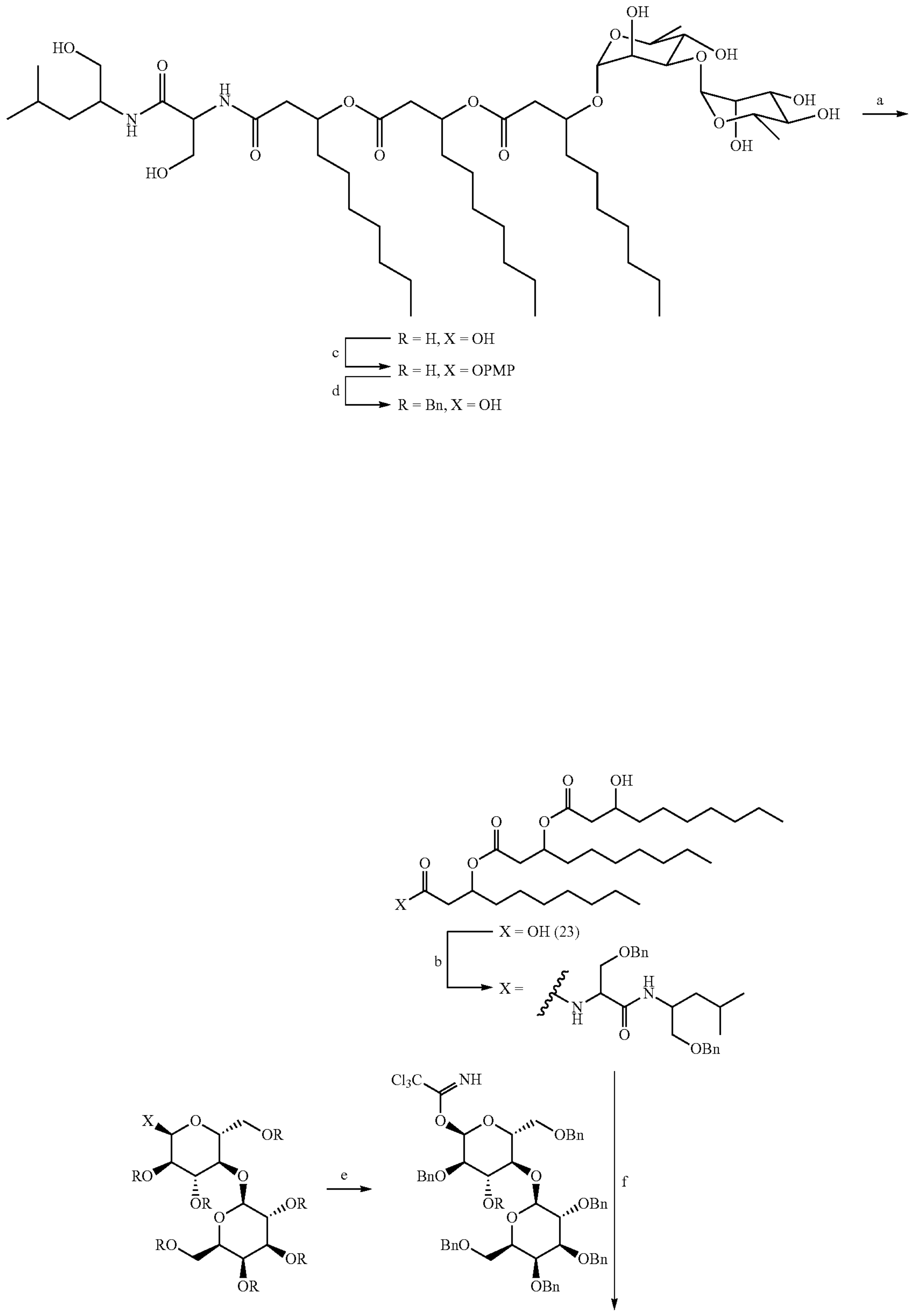

-continued

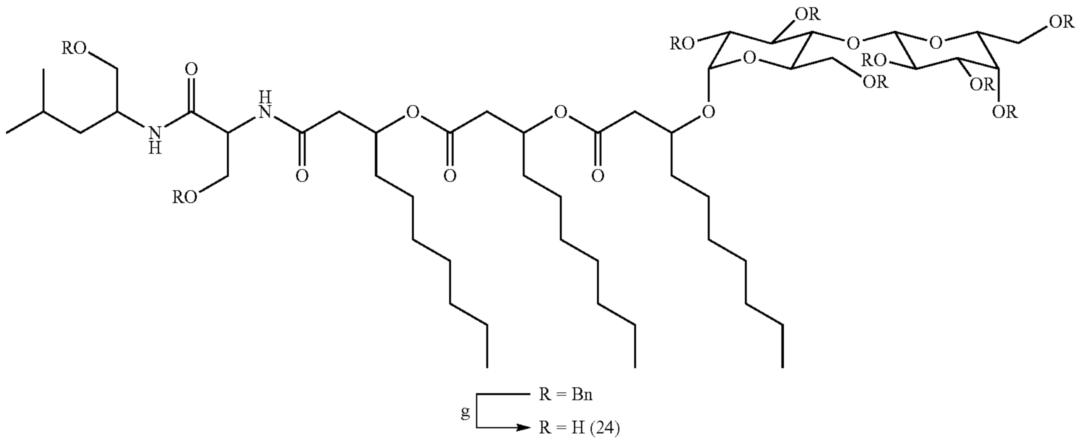

Alternative semisynthetic route to glycolipopeptide analogues from tridecanoic acid (23) and commercially available disaccharides.
Reagents and conditions:
(a) 1M HCl, $CH_3CN$:$H_2O$ (1:1), 95° C., 16 h.
(b) (i) DIC, NHS, 0° C. → 25° C., 3 h. (ii) Leucinol(Bzl)-Ser(Bzl)$NH_2$ (21), $Et_3N$, DMAP, 25° C., 3 h.
(c) (i) $Ac_2O$, pyridine, 70° C., 16 h. (ii) p-methoxyphenol, $BF_3$•$Et_2O$, $CH_2Cl_2$, 0° C. → 25° C., 3 h. (iii) $NaOCH_3$, $CH_3OH$.
(d) (i) BnBr, $Bu_4NI$, NaH, DMF, 0° C. → 25° C., 3 h. (ii) 80% $CH_3CN$, CAN, 35° C., 30 min.
(e) $CCl_3CN$, DBU, $CH_2Cl_2$, 25° C., 30 min.
(f) $BF_3$•$Et_2O$ (cat.), anhydrous $CH_2Cl_2$, -78° C., 2 h.
(g) 10% Pd/C (20 wt %), $H_2$, $CH_2Cl_2$, 25° C., 16 h.

Scheme 10. Semisynthesis of a glycolipopeptide analouge (25) from commercially available rhamnolipids.

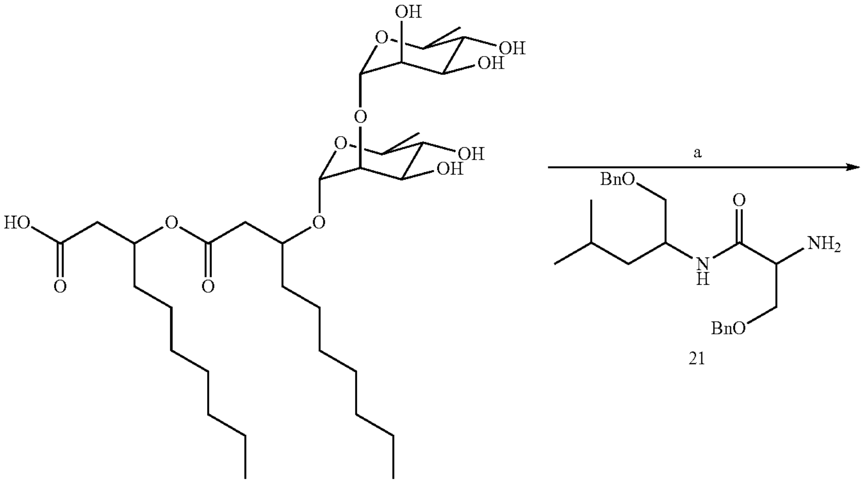

21

-continued

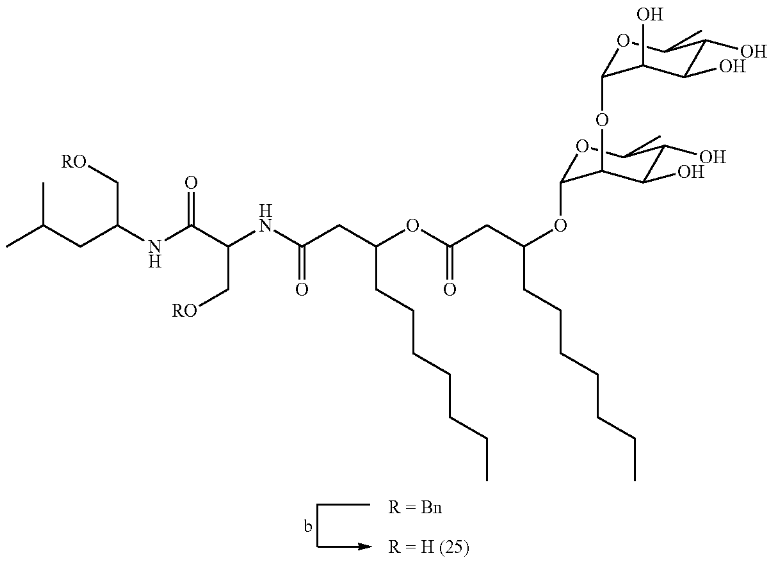

Reagents and conditions: (a) (i) PyBOP, DMF, 0° C. → 25° C., 2 h. (ii) Leucinol(Bzl)—Ser(Bzl)$NH_2$ (21), $Et_3N$, 0° C. → 25° C., 2 h. (b) 10% Pd/C (20 wt%), $H_2$, $CH_2Cl_2$, 25° C., 16 h Conceivably one skilled in the art of organic synthesis could isolate naturally occurring glycolipopeptides from a microbial fermentation and synthesize derivatives, analogues, and other structural variants. For instance, modifications that could occur at $R_{5a}$, $R_{5b}$, $R_{6a}$, $R_{6b}$, $R_{7a}$, $R_{7b}$, $R_{10}$, and $R_{11}$ include, but are not limited to, alkylation, acylation, glycosylation, phosphorylation, and sulfation. The glycolipopeptides could also undergo a base hydrolysis to produce rhamnolipid-like compounds with potentially useful surfactant properties. It is also known that a base hydrolysis reaction would provide NB-RLP374.

Methods of Use

The glycolipopeptides described herein might be used similarly to other surfactants. They may, for example, be used as detergents, emulsifiers, dispersants, wetting agents, foaming agents, or biofilm inhibitors/disruptors. A typical use would be for the preparation of emulsions for cosmetic or pharmaceutical formulations (e.g., water-in-oil or oil-in-water emulsions), where one or more glycolipopeptides or derivatives or analogues thereof is mixed with a polar component and a non-polar component.

The properties of the surfactants of this invention also make them suitable as emulsifiers particularly in oil in water or water-in-oil emulsions e.g. in personal care applications. Personal care emulsion products can take the form of creams and milks desirably and typically include emulsifier to aid formation and stability of the emulsion. Typically, personal care emulsion products use emulsifiers (including emulsion stabilisers) in amounts of about 3 to about 5% by weight of the emulsion.

The oil phase of such emulsions are typically emollient oils of the type used in personal care or cosmetic products, which are oily materials which is liquid at ambient temperature or solid at ambient temperature, in bulk usually being a waxy solid, provided it is liquid at an elevated temperature, typically up to 100° C. more usually about 80° C., so such solid emollients desirably have melting temperatures less than 100° C., and usually less than 70° C., at which it can be included in and emulsified in the composition.

The concentration of the oil phase may vary widely and the amount of oil is typically from 1 to 90%, usually 3 to 60%, more usually 5 to 40%, particularly 8 to 20%, and especially 10 to 15% by weight of the total emulsion. The amount of water (or polyol, e.g. glycerin) present in the emulsion is typically greater than 5%, usually from 30 to 90%, more usually 50 to 90%, particularly 70 to 85%, and especially 75 to 80% by weight of the total composition. The amount of surfactant used in such emulsions may be in the range from 0.001 to 10% by weight of the emulsion, preferably 0.01 to 6% by weight, more preferably 0.1 to 5% by weight, further preferably 1 to 3% by weight. The amount of surfactant used on such emulsions is typically from 2 to 5.5%, by weight of the emulsion.

The end uses formulations of such emulsions include moisturizers, sunscreens, after sun products, body butters, gel creams, high perfume containing products, perfume creams, baby care products, hair conditioners, skin toning and skin whitening products, water-free products, anti-perspirant and deodorant products, tanning products, cleansers, 2-in-1 foaming emulsions, multiple emulsions, preservative free products, emulsifier free products, mild formulations, scrub formulations e.g. containing solid beads, silicone in water formulations, pigment containing products, sprayable emulsions, colour cosmetics, conditioners, shower products, foaming emulsions, make-up remover, eye make-up remover, and wipes. A preferred formulation type is a sunscreen containing one or more organic sunscreens and/or inorganic sunscreens such as metal oxides, but desirably includes at least one particulate titanium dioxide and/or zinc oxide.

All of the features described herein may be combined with any of the above aspects, in any combination. It is to be understood that the invention is not to be limited to the details of the above embodiments, which are described by way of example only. Many variations are possible.

In order that the present invention may be more readily understood, reference will now be made, by way of example, to the following description.

EXAMPLES

Example 1: Isolation of *Variovorax paradoxus* RKNM-096

Bacterial strain RKNM-096 was isolated from soil collected from the Battle Bluffs area west of Kamloops, British Columbia. RKNM-096 was isolated as a mucoid, yellow pigmented colony, and purified by serial subculturing. The bacterium was identified by 16S rRNA gene analysis, which indicated that RKNM-096 was a strain of *V. paradoxus.*

Example 2: Identifying *Variovorax paradoxus* RKNM-096 as a Biosurfactant Producer

*V. paradoxus* RKNM-096 was identified as a biosurfactant producer in a screen aimed at identifying bacterial producers of biosurfactants with emulsifying properties. The assay utilized to identify bacterial producers of biosurfactants was the emulsification activity assay. In this assay cultures were grown in 10 mL of liquid medium in 25 mm×150 mm glass tubes at 30° C. with shaking at 200 rpm for 5 days. After 5 days, the cells were removed by centrifugation and 3.5 mL of cell free culture broth was mixed with 3.5 mL of kerosene in a 13 mm×100 mm test tube with a screw cap tube. The tubes were vortexed for two minutes and then allowed to stand overnight at room temperature after which the height of the emulsion ($h_{emuls}$) and the total height ($h_{total}$) of the liquid in the tube were measured. The emulsification index ($E_{24}$) was calculated using the equation $E_{24}=h_{emuls}/h_{total}\times100\%$. Fermentation broths of *V. paradoxus* RKNM-096 cultured in ISP2 broth (0.4% maltose, 0.4% yeast extract, 1.0% dextrose, pH 7.0) exhibited an $E_{24}$ value of 50.7%.

Example 3: Identification of Glycolipopeptide Biosurfactants Produced by *Variovorax paradoxus* RKNM-096

To determine if a small molecule was responsible for the observed emulsification activity, *V. paradoxus* RKNM-096 was fermented in ISP2 broth as described above and the broth was extracted twice with 10 mL of ethyl acetate (EtOAc). The EtOAc extract was then washed twice with 10 mL of water to remove any remaining polar media components from the EtOAc extract. For comparison purposes an ISP2 media blank was extracted in an identical manner. The EtOAc extracts were evaporated in vacuo and reconstituted in $CH_3OH$ at a concentration of 0.5 mg/mL. The extracts were separated by ultra high performance liquid chromatography (UPLC; Accela™ Thermo Fisher Scientific Mississauga, ON, Canada) and the eluates analyzed with a photodiode array detector (200-600 nm) (PDA; Accela™, Thermo Fisher Scientific Mississauga, ON, Canada), an evaporative light scattering detector (ELSD; Sedex, Sedere, Alfortville, France) and a high resolution mass spectrometer utilizing electrospray ionization (HRESIMS) (Orbitrap Exactive; Thermo Fisher Scientific, Mississauga, ON, Canada) (positive mode, monitoring m/z 200-2000). Chromatographic separation was achieved with a Kinetex 1.7 μm $C_{18}$ 100 Å 50×2.1 mm column (Phenomenex, Torrance, Calif., USA) and a linear gradient from 95% $H_2O$/0.1% formic acid (FA) (solvent A) and 5% acetonitrile ($CH_3CN$)/0.1% FA (solvent B) to 100% solvent B over 5 min followed by a hold of 100% solvent B for 3 min with a flow rate of 400 μL/min. Examination of the ELSD chromatogram of the *V. paradoxus* RKNM-096 extract revealed five prominent peaks. The first peak eluted at 0.50 min and was present in the media blank indicating this peak was composed of media components. The following four peaks (1-4) eluted at 3.0 min, 5.04 min, 5.29 min and 5.39 min in the ELSD chromatogram, respectively. These peaks were not observed in the media blank extracts, indicating that these peaks were metabolic products of *V. paradoxus* RKNM-096. Peak 1 eluted at 3.00 min and examination of the mass spectrum of the corresponding peak in the total ion chromatogram (3.04 min) revealed the presence of two ions with mass to charge ratios (m/z) of 375.2855 and 397.2673, which is consistent with the anticipated $[M+H]^+$ and $[M+Na]^+$ for a compound with a molecular formula of $C_{19}H_{38}N_2O_5$ and mass of 374.2781. The mass spectra of peaks 2-4 were examined in an identical manner and the $[M+H]^+$ ions were identified as m/z 1007.6628, 1049.6778, and 1049.6734, respectively. The difference in mass between the $[M+H]^+$ ions associated with peaks 3 and 4 was 4.2 ppm, suggesting that these two compounds likely had an identical molecular formula, however the slight difference in retention time indicated that they were probably closely related structural analogues.

The compounds were also elucidated using NMR. The NMR data indicated the presence of four carbonyl groups in addition to two sugar residues with characteristic anomeric carbon chemical shifts at $\delta_C$ 101.4 and $\delta_C$ 103.9. Key COSY and HMBC correlations allowed the chemical characterization of the amino acid-derived leucinol, a serine residue, and three 3-hydroxydecanoic acids (FIG. 1). The connectivity between the different moieties was further confirmed by tandem mass spectrometry. The two deoxyhexose residues were identified by interpretation of $^1H$—$^1H$ COSY correlations and coupling constant analysis. The small J-coupling exhibited by the anomeric proton H-1' ($\delta_H$ 4.79, d, J=1.4 Hz) and the methine proton H-2' ($\delta_H$ 3.86, dd, J=3.2, 1.4 Hz) placed protons H-1' and H-2' in the equatorial position, while the larger J-coupling for H-4' ($\delta_H$ 3.53-3.48, app. t) indicated the axial relationship with H-3' and H-5', and therefore suggested an α-rhamnopyranosyl residue. The HMBC cross peak between the anomeric proton H-1' and C-3C ($\delta_C$ 76.5) demonstrated the attachment of this sugar to the 3-hydroxydecanoic acid moiety. The second sugar residue was also identified as an α-rhamnopyranose on the basis of coupling constant values. The small J-coupling for H-1" ($\delta_H$ 5.01, d, J=1.5 Hz) and H-2" ($\delta_H$ 3.98, dd, J=3.3, 1.5 Hz) indicated the equatorial orientation of these protons, while the larger coupling constant for H-4" ($\delta_H$ 3.40, app. t, J=9.5 Hz) demonstrated its axial relationship with H-3" and H-5". A key HMBC correlation between H-3' and C-1" established a 1,3-α-glycosidic linkage between the two rhamnopyranose moieties.

The structure of NB-RLP1006 is:

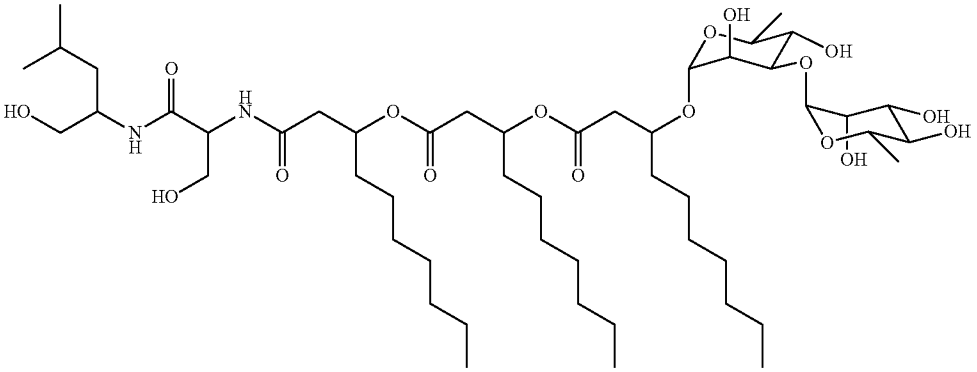 [SMILES: CCCCCCCC(CC(=O)NC(CO)C(=O)NC(CO)CC(C)C)OC(=O)CC(CCCCCCC)OC(=O)CC(CCCCCCC)OC1OC(C)C(O)C(OC2OC(C)C(O)C(O)C2O)C1O]

Organic extracts from *V. paradoxus* RKNM-096 were also fractionated by automated normal-phase chromatography followed by reversed-phase HPLC, which provided NB-RLP1048A and NB-RLP1048B. On the basis of HRESIMS analysis (NB-RLP1048A: HRESIMS m/z 1049.6778 $[M+H]^+$; NB-RLP1048B: HRESIMS 1049.6734 $[M+H]^+$, calcd for $C_{53}H_{97}N_2O_{18}$, 1049.6731), these compounds were determined to be mono-acetylated analogues of NB-RLP1006. The apparent molecular formula of these compounds is $C_{53}H_{96}N_2O_{18}$. Based on NMR analysis, NB-RLP1048A consisted of an inseparable mixture of acetylated glycolipopeptides with the structure:

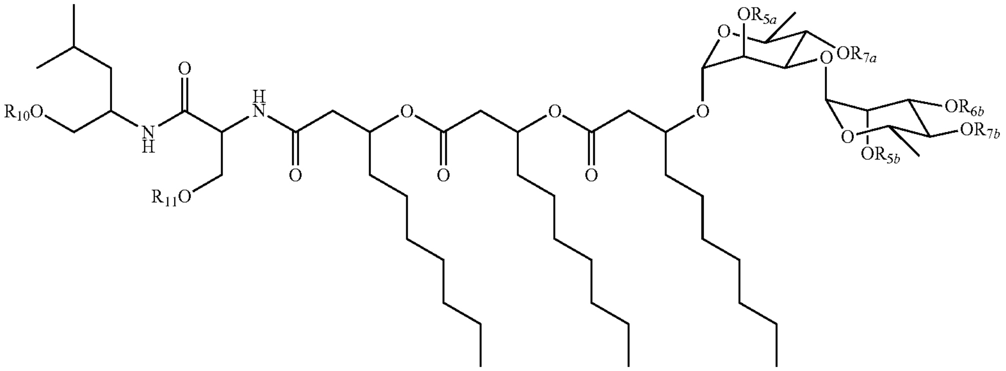

where any single R-group is an acetyl group, while all other R-groups are hydrogen atoms.

The chemical structure of NB-RLP1048B was determined by 1D and 2D NMR spectroscopic techniques, confirming the location of the acetyl group at the C-3" position.

The chemical structure of NB-RLP1048B is:

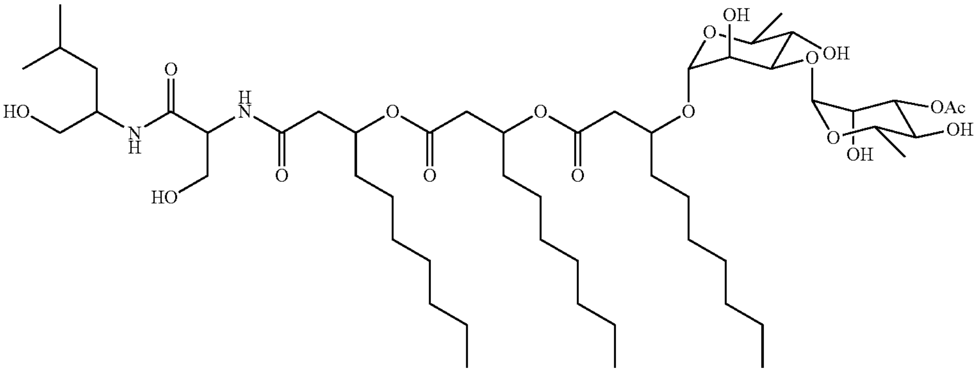 [SMILES: CCCCCCCC(CC(=O)NC(CO)C(=O)NC(CO)CC(C)C)OC(=O)CC(CCCCCCC)OC(=O)CC(CCCCCCC)OC1OC(C)C(O)C(OC2OC(C)C(O)C(OC(C)=O)C2O)C1O]

The described fractionation scheme also yielded several other glycolipopeptide analogues produced by *V. paradoxus* RKNM-096 in smaller quantities, including 10.9 mg of NB-RLP978. The $^1$H and $^{13}$C NMR data were nearly identical to that of NB-RLP1006. The apparent molecular formula of NB-RLP978 is $C_{49}H_{90}N_2O_{17}$ (HRESIMS m/z 979.6307 $[M+H]^+$, calcd for $C_{49}H_{91}N_2O_{17}$, 979.6312). On the basis of tandem mass spectrometry, NB-RLP978 was determined to be an inseparable mixture of three closely related analogues, NB-RLP978A, NB-RLP978B, and NB-RLP978C, containing a $C_8$ acyl chain at one of the 3-hydroxyalkanoic acid positions.

The chemical structure of NB-RLP978A-C is:

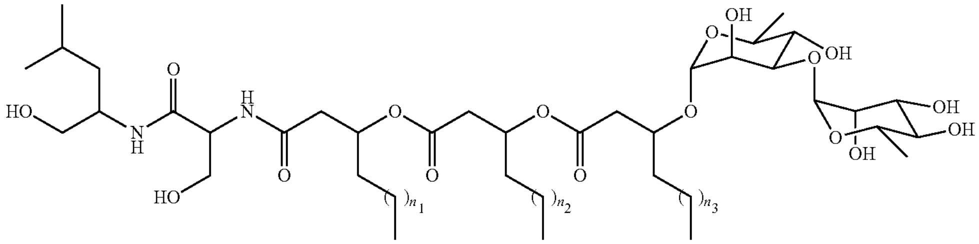

where any single acyl chain is $C_8$ (i.e. $n_1$, $n_2$, or $n_3$=3) while the remaining acyl chains are $C_{10}$ (i.e. n=5). NB-RLP978A: $n_1$=$n_2$=5, $n_3$=3; NB-RLP978B: $n_1$=$n_3$=5, $n_2$=3; NB-RLP978C: $n_1$=3, $n_2$=$n_3$=5.

The reversed-phase HPLC purification of NB-RLP1006 and NB-RLP978A-C also yielded NB-RLP950, an inseparable mixture of compounds with an apparent molecular formula of $C_{47}H_{86}N_2O_{18}$ (HRESIMS m/z 951.5982 $[M+H]^+$ calcd for $C_{47}H_{87}N_2O_{18}$, 951.5999), which is consistent with an analogue of NB-RLP1006 lacking four methylene groups. The $^1$H NMR spectrum of NB-RLP950 was nearly identical to that of NB-RLP1006 and NB-RLP978. A $^{13}$C spectrum was not obtained due to insufficient material. On the basis of tandem mass spectrometry, NB-RLP950 was determined to be a mixture of six closely related analogues: NB-RLP950A, NB-RLP950B, NB-RLP950C, NB-RLP950D, NB-RLP950E, and NB-RLP950F. These glycolipopeptide analogues either contain two $C_8$ acyl chains or one $C_6$ acyl chain at the 3-hydroxyalkanoic acid positions.

The chemical structure of NB-RLP950A-F is:

where any two acyl chains are $C_8$ (e.g. $n_1$=$n_2$=3 and $n_3$=5) while the remaining acyl chain is $C_6$ (i.e. n=1). NB-RLP950A: $n_1$=5, $n_2$=$n_3$=3; NB-RLP950B: $n_2$=5, $n_1$=$n_3$=3; NB-RLP950C: $n_3$=5, $n_1$=$n_2$=3; NB-RLP950D: $n_1$=$n_2$=5, $n_3$=1; NB-RLP950E: $n_1$=$n_3$=5, $n_2$=1; NB-RLP950F: $n_2$=$n_3$=5, $n_2$=1.

The reversed-phase HPLC purification of NB-RLP1048B also yielded NB-RLP1020. The $^1$H and $^{13}$C NMR data of NB-RLP1020 were nearly identical to that of NB-RLP1048B. The apparent molecular formula of NB-RLP1020 is $C_{51}H_{92}N_2O_{18}$ (HRESIMS m/z 1021.6415 $[M+H]^+$, calcd for $C_{51}H_{93}N_2O_{18}$, 1021.6418). On the basis of tandem mass spectrometry, NB-RLP1020 was determined to be an inseparable mixture of three closely related analogues, NB-RLP1020A, NB-RLP1020B, and NB-RLP1020C, comprising a $C_8$ acyl chain at one of the 3-hydroxyalkanoic acid positions.

The chemical structure of NB-RLP1020A-C is:

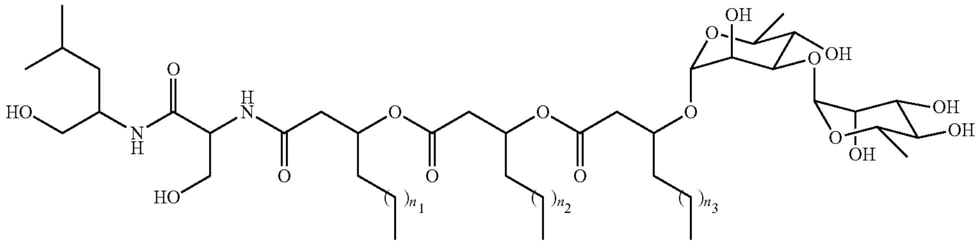

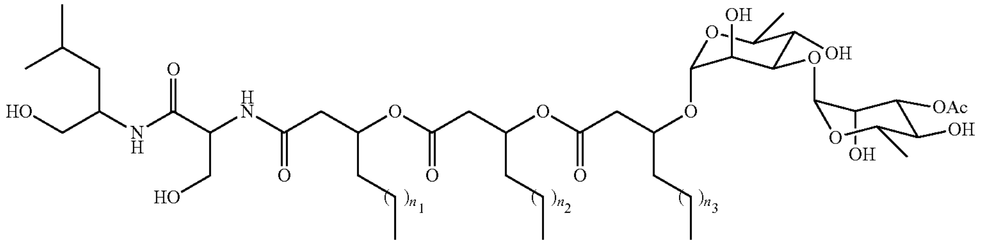

where any single acyl chain is $C_8$ (i.e. $n_1$, $n_2$, or $n_3$=3) while the remaining acyl chains are $C_{10}$ (i.e. n=5). NB-RLP1020A: $n_1$=$n_2$=5, $n_3$=3; NB-RLP1020B: $n_1$=$n_3$=5, $n_2$=3; NB-RLP1020C: $n_1$=3, $n_2$=$n_3$=5.

The reversed-phase HPLC fractionation also yielded an inseparable mixture of compounds with an apparent molecular formula of $C_{51}H_{92}N_2O_{18}$ (HRESIMS m/z 1021.6477 $[M+H]^+$, calcd for $C_{51}H_{93}N_2O_{18}$, 1021.6418). Similar to NB-RLP1020A-C, the structure of these compounds is:

where any single acyl chain is $C_{12}$ (i.e. $n_1$, $n_2$, or $n_3$=7) while the remaining acyl chains are $C_{10}$ (i.e. n=5). NB-RLP1076A: $n_1$=$n_2$=5, $n_3$=7; NB-RLP1076B: $n_1$=$n_3$=5, $n_2$=7; NB-RLP1076C: $n_1$=7, $n_2$=$n_3$=5.

The reversed-phase HPLC fractionation also yielded an inseparable mixture of compounds with an apparent molecular formula of $C_{55}H_{100}N_2O_{18}$ (HRESIMS m/z 1077.7098 $[M+H]^+$ calcd for $C_{55}H_{101}N_2O_{18}$, 1077.7044). Similar to NB-RLP1076A-C, the structure of these compounds is:

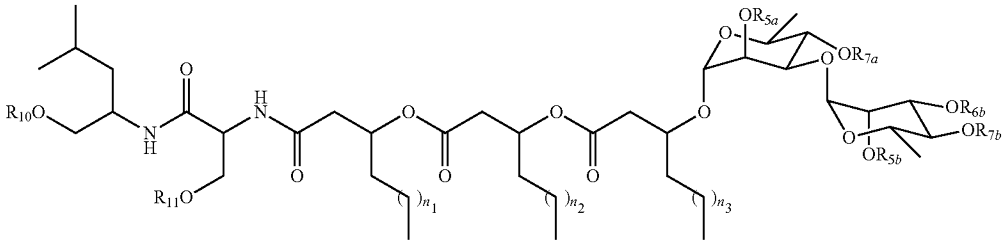

where any single R-group is an acetyl group, while all other R-groups are hydrogen atoms and where any single acyl chain is $C_8$ (i.e. $n_1$, $n_2$, or $n_3$=3) while the remaining acyl chains are $C_{10}$ (i.e. n=5).

The reversed-phase HPLC fractionation also yielded NB-RLP1076. The $^1H$ and $^{13}C$ NMR data were nearly identical to that of NB-RLP1020A-C and NB-RLP1048B. The apparent molecular formula of NB-RLP1076 is $C_{55}H_{100}N_2O_{18}$ (HRESIMS m/z 1077.7046 $[M+H]^+$ calcd for $C_{55}H_{101}N_2O_{18}$, 1077.7044). On the basis of tandem mass spectrometry, NB-RLP1076 was determined to be an inseparable mixture of three closely related analogues, NB-RLP1076A, NB-RLP1076B, and NB-RLP1076C, comprising a $C_{12}$ acyl chain at one of the 3-hydroxyalkanoic acid positions.

The chemical structure of NB-RLP1076A-C is:

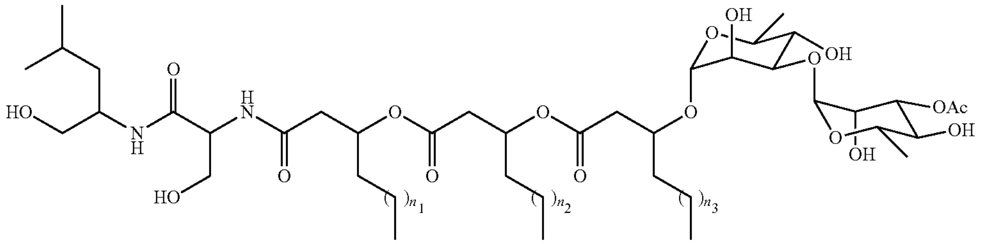

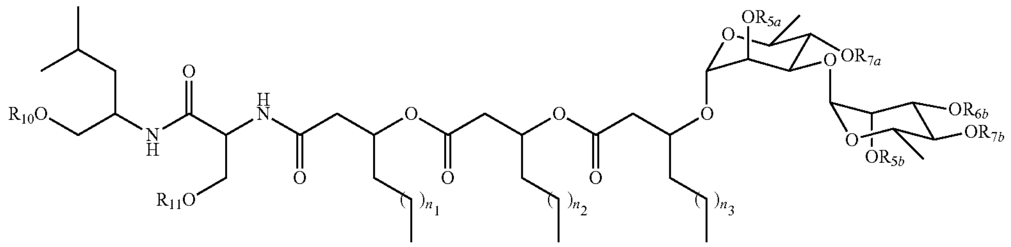

where any single R-group is an acetyl group, while all other R-groups are hydrogen atoms and where any single acyl chain is $C_{12}$ (i.e. $n_1$, $n_2$, or $n_3$=7) while the remaining acyl chains are $C_{10}$ (i.e. n=5).

Using portions of the *V. paradoxus* RKNM-096 glycolipopeptide biosurfactant biosynthetic gene cluster as in silico probes against published bacteria genomes (described below), we identified *Janthinobacterium agaricidamnosum* DSM 9628 as a potential producer of glycolipopeptide biosurfactants similar to those isolated from *V. paradoxus* RKNM-096. *J. agaricidamnosum* was cultured and extracted as described above for *V. paradoxus* RKNM-096 and the resulting organic extract (110.4 mg) of was subjected to automated reversed-phase chromatography with a RediSep Cis column using a $H_2O/CH_3OH$ gradient. Fractions containing the glycolipopeptide (77.6 mg) were combined and a portion of this material was subjected to further separation by reversed-phase HPLC, which yielded 17.1 mg of NB-RLP860 and 6.4 mg of NB-RLP832. Analysis of NB-RLP860 by HRESIMS (HRESIMS m/z 861.6033 $[M+H]^+$ calcd for $C_{45}H_{85}N_2O_{13}$, 861.6046) indicated an apparent molecular formula of $C_{45}H_{84}N_2O_{13}$ and five degrees of unsaturation. The $^1H$ and $^{13}C$ NMR data of NB-RLP860 were similar to NB-RLP1006, except the NMR spectra lacked resonances belonging to the second α-rhamnopyranose moiety.

The chemical structure of NB-RLP860 was determined by 1D and 2D NMR spectroscopy. The structure of NB-RLP860 is:

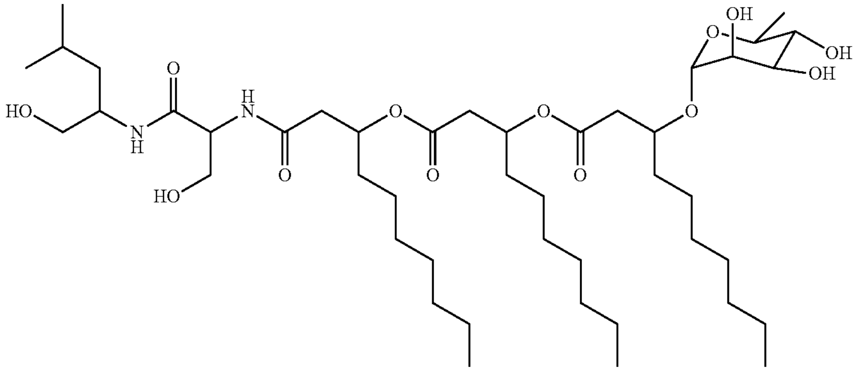 [SMILES: CCCCCCCC(CC(=O)NC(CO)C(=O)NC(CO)CC(C)C)OC(=O)CC(CCCCCCC)OC(=O)CC(CCCCCCC)OC1OC(C)C(O)C(O)C1O]

Analysis of NB-RLP832 by HRESIMS (HRESIMS m/z 833.5734 $[M+H]^+$, calcd for $C_{45}H_{81}N_2O_{13}$, 833.5733) indicated an apparent molecular formula of $C_{43}H_{80}N_2O_{13}$. The $^1H$ and $^{13}C$ NMR data were nearly identical to that of NB-RLP860. On the basis of tandem mass spectrometry, NB-RLP832 was determined to be an inseparable mixture of three closely related analogues, NB-RLP832A, NB-RLP832B, and NB-RLP832C, comprising a $C_8$ acyl chain at one of the 3-hydroxyalkanoic acid positions.

The chemical structure of NB-RLP832A-C is:

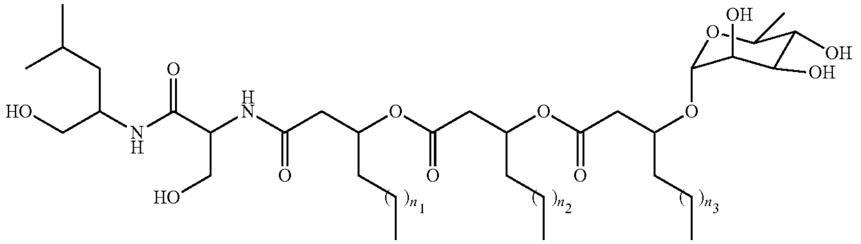

where any single acyl chain is $C_8$ (i.e. $n_1$, $n_2$, or $n_3$=3) while the remaining acyl chains are $C_{10}$ (i.e. n=5). NB-RLP832A: $n_1$=$n_2$=5, $n_3$=3; NB-RLP832B: $n_1$=$n_3$=5, $n_2$=3; NB-RLP832C: $n_1$=3, $n_2$=$n_3$=5.

Glycolipopeptides NB-RLP860 and NB-RLP832A-C were also detected in small quantities in organic extracts of

*V. paradoxus* RKNM-096 by LC-MS analysis. Analysis of HRESIMS chromatograms revealed $[M+H]^+$ ions of m/z 861.6073 and m/z 833.5749, which are consistent with the predicted m/z of $[M+H]^+$ ions for NB-RLP860 (calcd for $C_{45}H_{85}N_2O_{13}$, m/z 861.6046 $[M+H]^+$) and NB-RLP832A-C(calcd for $C_{45}H_{81}N_2O_{13}$, m/z 833.5733 $[M+H]^+$).

Analysis of organic extracts of *V. paradoxus* RKNM-096 also revealed three peaks in the HRESIMS chromatogram exhibiting $[M+H]^+$ ions of m/z 903.6213, which is consistent with the predicted $[M+H]^+$ ions for an acetylated analogue of NB-RLP860 (m/z 903.6152 $[M+H]^+$). As these compounds were produced in small quantities, attempts to determine their structures unambiguously by NMR spectroscopy were prohibited. These compounds were not detected in organic extracts from *J. agaricidamnosum* DSM 9628. Given the observed fragment ions of m/z 715.5480 (b) and 598.4310 (bf), these compounds were identified as acetylated glycolipopeptides NB-RLP902 with the structure:

where any single R-group is an acetyl group, while all other R-groups are hydrogen atoms and where any single acyl chain is $C_8$ (i.e. $n_1$, $n_2$, or $n_3$=3) while the remaining acyl chains are $C_{10}$ (i.e. n=5).

Example 4: Deacetylation of NB-RLP1048A and Other Acetylated Glycolipopeptide Biosurfactants Produced by *Variovorax paradoxus* RKNM-096

It is known that the relative amount of NB-RLP1006 and acetylated glycolipopeptides (e.g. NB-RLP1048A) produced by *V. paradoxus* RKNM-096 may vary between batches using different culture media and fermentation conditions. As a result, the surfactant properties of the extracted glycolipopeptide product may also vary. As product consistency is important to be competitive in the biosurfactant industry, a method to selectively remove the acetate from $R_{5a}$, $R_{5b}$, $R_{6a}$, $R_{6b}$, $R_{7a}$, $R_{7b}$, $R_{10}$, and $R_{11}$ was developed to

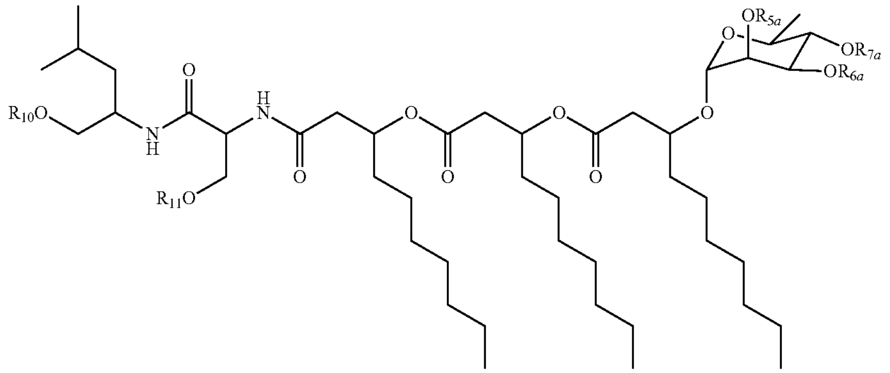

where any single R-group is an acetyl group, while all other R-groups are hydrogen atoms.

Fractions generated by automated reversed-phase chromatography of organic extracts from *V. paradoxus* RKNM-096 were enriched with NB-RLP902. Also detected in the HRESIMS chromatograms of these fractions was a small peak exhibiting a $[M+H]^+$ ion of m/z 875.5888, which is consistent with an analogue of NB-RLP902 lacking two methylene groups. This $[M+H]^+$ ion was not observed in organic extracts from *J. agaricidamnosum* DSM 9628. The observed fragment ion of 687.5164 (b) indicates that this compound is also a glycolipopeptide. Similar to NB-RLP978A-C, NB-RLP1020A-C, and NB-RLP832A-C, it is proposed that this peak is comprised of three compounds NB-RLP874A-C with the structure:

generate a consistent glycolipopeptide product comprised of NB-RLP1006 with >95% purity by weight (Scheme 1). The method utilizes NaOH within a narrow concentration range to selectively remove acetate moieties without inducing further hydrolysis of the amide, ester, or glycosidic linkages of the glycolipopeptide. The NaOH concentration and reaction solvent both have a demonstrated role in controlling the extent of hydrolysis and achieving selectively. Optimal NaOH concentrations are directly proportional to the concentration and composition of the glycolipopeptides in the reaction medium. Reaction solvents with higher water composition, such as $H_2O$:acetone (9:1), showed better selectivity and minimized the hydrolysis of the ester linkages between the β-hydroxyalkanoic acid moieties.

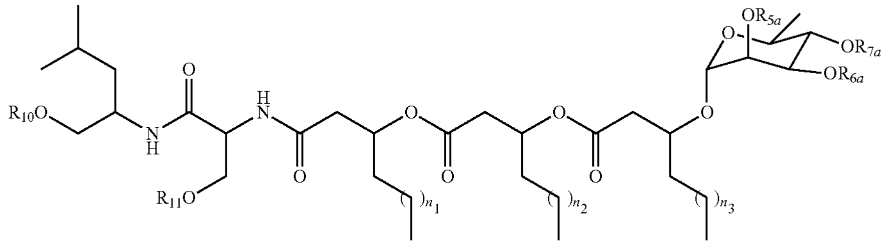

Scheme 1.

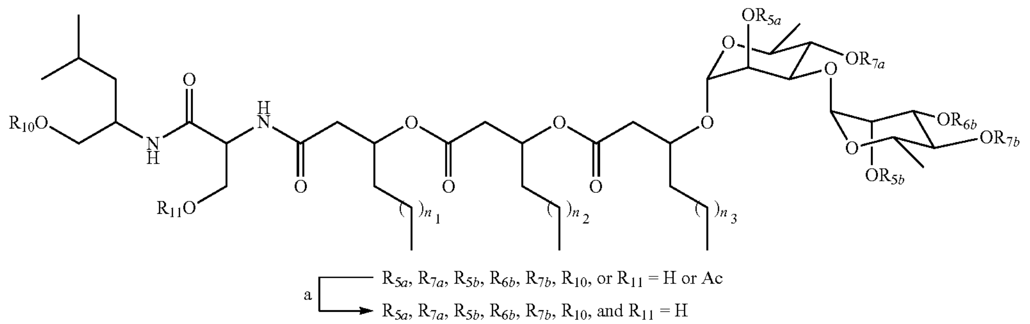

Selective hydrolysis of acetate moieties on a mixture of glycolipopeptide biosurfactants containing acetylated analogues of NB-RLP1006 (e.g. NB-RLP1048A).
Reagents and conditions:
(a) glycolipopeptide (1.0 mg/mL), NaOH (1.5 mM), $H_2O$; acetone (9:1), 25° C., 40 h.

It is known that deacetylation of the glycolipopeptide mixture may be achieved with variations to the method described herein. It is possible that inorganic bases other than NaOH, including but not limited to LiOH, KOH, $Na_2CO_3$, $NH_3$, and $NH_4OH$, or organic bases, including but not limited to tetrabutylammonium hydroxide or alkylamines, may be utilized. The selective deacetylation may also be achieved enzymatically using esterases, including but not limited to acetylesterases and lipases.

Hydrolysis of the glycolipopeptide mixture is known to produce several products, including but not limited to the lipopeptides NB-RLP356 (HRESIMS m/z 357.2745 $[M+H]^+$, calcd for $C_{19}H_{37}N_2O_4$, 357.2748; m/z 379.2567 $[M+Na]^+$, calcd for $C_{19}H_{36}N_2O_4Na$, 379.2565), NB-RLP374 (HRESIMS m/z 375.2851 $[M+H]^+$, calcd for $C_{19}H_{39}N_2O_5$, 375.2854), and NB-RLP526 (HRESIMS m/z 527.4054 $[M+H]^+$, calcd for $C_{29}H_{55}N_2O_6$, 527.4055), and the glycolipids NB-RLP480 (HRESIMS m/z 481.2599 $[M+H]^+$, calcd for $C_{22}H_{41}O_{11}$, 481.2643; m/z 503.2465 $[M+Na]^+$, calcd for $C_{22}H_{40}O_{11}Na$, 503.2463) and NB-RLP650 (HRESIMS m/z 651.3962 $[M+H]^+$, calcd for $C_{32}H_{59}O_{13}$, 651.3950). Given their amphiphilic structures, these compounds are also expected to behave as surface active agents and may exhibit surfactant properties that may be unique or complementary to the glycolipopeptides. These compounds are known to be formed during the deacetylation process described herein and are thus present in the glycolipopeptide final product. Although normally present in small quantities (<5% by weight), these compounds may contribute to the surfactant characteristics of the glycolipopeptide product. Hydrolysis of the glycolipopeptides may also occur spontaneously, for instance during the extraction and purification, to generate these compounds. For instance, the lipopeptide NB-RLP374 is detected in the organic extract of *V. paradoxus* RKNM-096 before the glycolipopeptide material is subjected to any downstream modification.

The chemical structure of NB-RLP356 is:

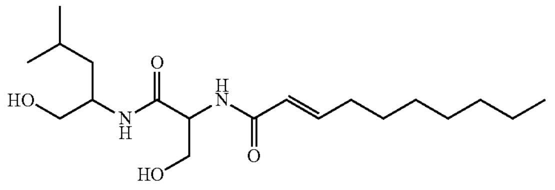 [SMILES: CCCCCCC/C=C/C(=O)NC(CO)C(=O)NC(CO)CC(C)C]

The chemical structure of NB-RLP374 is:

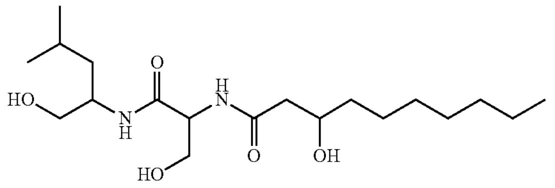 [SMILES: CCCCCCCC(O)CC(=O)NC(CO)C(=O)NC(CO)CC(C)C]

The chemical structure of NB-RLP526 is:

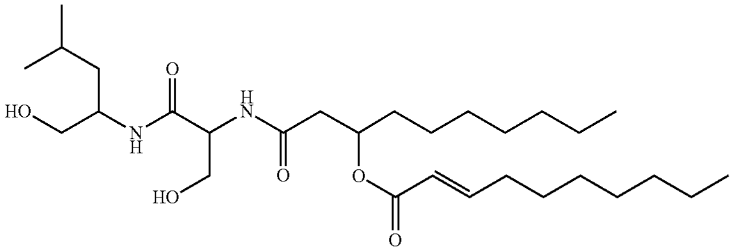 [SMILES: CCCCCCC/C=C/C(=O)OC(CCCCCCC)CC(=O)NC(CO)C(=O)NC(CO)CC(C)C]

The chemical structure of NB-RLP480 is:

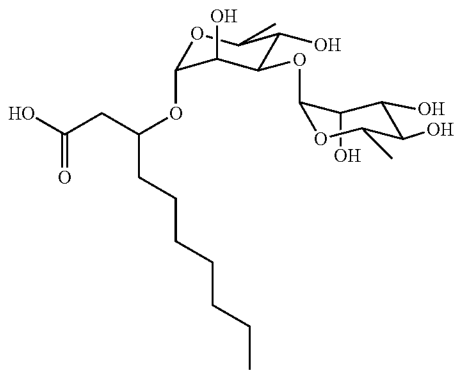 [SMILES: CCCCCCCC(CC(=O)O)OC1OC(C)C(O)C(OC2OC(C)C(O)C(O)C2O)C1O]

The chemical structure of NB-RLP650 is:

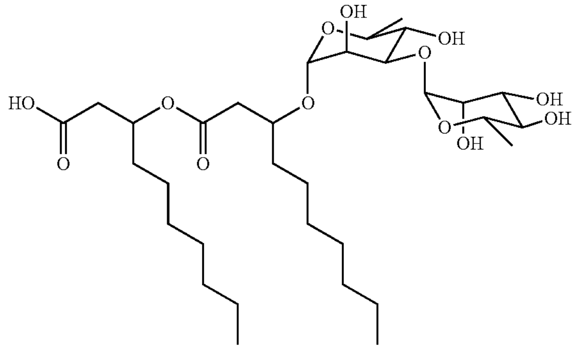 [SMILES: CCCCCCCC(CC(=O)O)OC(=O)CC(CCCCCCC)OC1OC(C)C(O)C(OC2OC(C)C(O)C(O)C2O)C1O]

Example 5: Surface Activity

As summarized in Table 1, the critical micelle concentrations (CMCs) of NB-RLP1006, NB-RLP978, NB-RLP860, and NB-RLP-1048B were determined by the Du Nouy method utilizing a Kibron Delta-8 multichannel microtensiometer (Kibron Inc., Helsinki, Finland). All samples were prepared in degassed deionized water (Millipore, Etobicoke, ON, CA) at concentrations ranging from 0 to 2.0 mM. All measurements were recorded between 24 and 25° C. and performed in duplicate. The critical micelle concentration of both NB-RLP1006 and NB-RLP978 was 0.20 mM (0.02 wt %). Surface tension measurements indicated that NB-RLP1006 and NB-RLP978 were capable of reducing the surface tension of water from 72 to 35.5 mN/m at their CMC. Meanwhile, NB-RLP860 and NB-RLP1048B exhibited CMC values of 0.85 mM (0.07 and 0.09 wt %, respectively), reducing the surface tension of water to 36.2 and 36.9 mN/m, respectively. The surface activity of NB-RLP1006 was compared to rhamnolipids A and B, which were purified from a commercially available rhamnolipid mixture (R90; AGAE Technologies, Corvallis, Oreg., USA) by reversed-phase HPLC. Rhamnolipids A and B both exhibited a CMC of 0.06 mM (0.003 and 0.004 wt %, respectively) in which the surface tension of water was reduced to 28.2 and 39.0 mN/m, respectively. The higher CMC values for NB-RLP860 and NB-RLP1048B may be due to their poor aqueous solubility.

TABLE 1

Surfactant properties of isolated glycolipopeptides compared to rhamnolipids. Critical micelle concentration (CMC) and surface tension reduction of water are shown.

| Compound | CMC (mM) | Minimum Surface Tension (mN/m) |
|---|---|---|
| NB-RLP1006 | 0.20 | 35.5 |
| NB-RLP1048B | 0.85 | 36.9 |
| NB-RLP860 | 0.85 | 36.2 |
| NB-RLP978 | 0.20 | 35.5 |
| Rhamnolipid A | 0.06 | 28.2 |
| Rhamnolipid B | 0.06 | 39.0 |

The characteristic curvature (Cc) of NB-RLP1006 was determined using the hydrophilic-lipophilic difference-net average curvature (HLD-NAC) model to calculate the shift in chemical potential when NB-RLP1006 is transferred from the oil to the aqueous phase as a function of salinity by the following general equation:

$$HLD=F(S)-k\times \mathrm{EACN}+F(A)-\alpha\times\Delta T+Cc$$

where F(S) is a function of salinity, k is a coefficient equal to 0.17, EACN (effective alkane carbon number) is the number of carbons in the alkane oil phase, a is a coefficient dependent on the type of surfactant (ionic, ethoxylates, etc), and ΔT is the effect of temperature. Four mixtures of NB-RLP1006 and sodium dihexyl sulfosuccinate (SDHS) were prepared with a total surfactant concentration of 1.8 mg/mL using the following NB-RLP1006/SDHS ratios: 0, 12, 24, and 40 wt % NB-RLP1006. An electrolyte scan was performed for each mixture by varying the NaCl concentration from 0 to 6.0% (w/v). Each mixture was added to an equal volume of toluene, which constituted the oil phase, and shaken vigorously. The optimal salinity (S*) was identified as the concentration of NaCl in which a Winsor Type III microemulsion was formed, wherein the separate middle phase was composed of an equal volume of oil and water. A plot of the NB-RLP1006/SDHS molar ratios versus S* was generated and Cc was calculated from the line of best fit. The Cc value for NB-RLP1006 was determined to be +5.2, a value that reflects the hydrophobic nature of this biosurfactant.

The emulsifying properties of NB-RLP1006 were determined using the emulsification index as described above. Pure NB-RLP1006 exhibited strong emulsification activity with an $E_{24}$ value of 53% at 1 mg/mL in deionized water. The emulsification of NB-RLP1006 is pH-dependent with $E_{24}$ values of 8, 38, and 31% at pH 3, 6, and 8, respectively. The type of emulsion formed by NB-RLP1006 (e.g. oil-in-water or water-in-oil) was determined using the drop dilution test. An emulsion was formed by vigorously mixing a 1 mg/mL solution of RLP1006 in deionized water with an equal volume of kerosene for 1 min. A portion (20 μL) of the emulsion was transferred to 0.5 mL of deionized water and 0.5 mL of kerosene and dilution of the emulsion in each liquid was monitored. The emulsion formed by NB-RLP1006 was readily dispersed in the aqueous phase, indicating that the continuous phase of the emulsion was water and that an oil-in-water (o/w) emulsion was formed by NB-RLP1006 under these conditions.

These results established that NB-RLP1006 is a potent biosurfactant capable of lowering the surface tension of water to 35.5 mN/m with a CMC comparable to that of two other well-characterized biosurfactants, rhamnolipids A and B. NB-RLP1006 also exhibits strong emulsification activity forming o/w emulsions under the conditions described herein.

Example 6: Cytotoxicity Testing of the Glycolipopeptides

To evaluate the safety profile of the glycolipopeptides, cytotoxicity testing was conducted against two normal human cell lines, BJ fibroblast cells ATCC CRL-2522 and adult epidermal keratinocytes (HEKa; Life Technologies, Carlsbad, Calif., USA). BJ fibroblasts were grown and maintained in 15 mL Eagle's minimal essential medium supplemented with fetal bovine serum (10% v/v), penicillin (100 μU) and streptomycin (100 μg/mL). HEKa cells were grown and maintained in 15 mL of EPI life medium (Life Technologies, Carlsbad, Calif., USA) supplemented with HKGS growth supplement (10% v/v; Life Technologies, Carlsbad, Calif., USA) and 50 μg/mL gentamicin (Sigma-Aldrich, St. Louis, Mo., USA). Cells were cultured in T75 $cm^2$ cell culture flasks and incubated at 37° C. in a humidified atmosphere of 5% $CO_2$. For BJ fibroblasts culture media was refreshed every two to three days and cells were not allowed to exceed 80% confluence. For HEKa cells growth medium was refreshed every 2 d until the cells reached 50% confluence and then the medium was refreshed every 24 h until 80% confluence was obtained. At 80% confluence, the cells were counted, diluted to 10,000 cells/well in growth medium lacking antibiotics and 90 μL of cell suspension was transferred into the wells of 96-well treated cell culture plates. The plates were incubated as before to allow cells to adhere to the plates for 24 h before treatment. DMSO was used as the vehicle at a final concentration of 1%. All compounds tested were re-solubilized in DMSO and a dilution series was prepared for each cell line using the respective cell culture growth medium, 10 μL of which were added to the assay wells yielding eight final concentrations ranging from 512 μg/mL to 8 μg/mL per well (final well volume of 100 μL). The fibroblasts and HEKa cells were incubated as previously described for 24 h. All samples were tested in triplicate. Each plate contained four un-inoculated media blanks (media+1% DMSO), four untreated growth controls (media+1% DMSO+ cells), and one column containing a serially diluted zinc pyrithione positive control. AlamarBlue (Life Technologies, Carlsbad, Calif., USA) was added to each well 24 h after treatment (10% v/v). Fluorescence (560/12 excitation, 590 nm emission) was monitored using a Varioskan Flash Multimode plate reader both at time zero and 4 h after the addition of alamarBlue. After subtraction of fluorescence at time zero from 4 h readings the percentage of cell viability relative to vehicle control wells was calculated. Low cytotoxic activity was displayed against the HEKa and BJ fibroblast cell lines. The observed $IC_{50}$ and $MIC_{90}$ values for the glycolipopeptides were significantly higher than the positive control zinc pyrithione, which served as an industry benchmark for topical antimicrobial agents (Table 2). These results indicate that the glycolipopeptides exhibit low cytotoxicity towards human skin cells and thus may be safe for use in applications which result in dermal contact such as cosmetic products.

TABLE 2

Cytotoxicity testing results for the glycolipopeptides. Values indicate the half maximal inhibitory concentrations ($IC_{50}$) and minimum inhibitory concentration that results in 90% of growth inhibition ($MIC_{90}$) in μg/mL. Error is reported as standard deviation.

| | Eukaryotic Cells | | | |
|---|---|---|---|---|
| Compound | HEKa ($IC_{50}$) | HEKa ($MIC_{90}$) | BJ ($IC_{50}$) | BJ ($MIC_{90}$) |
| NB-RLP1006 | 15.5 ± 1.7 | 64-128 | 19.5 ± 2.4 | 32 |
| NB-RLP1048B | 19.3 ± 4.0 | 64-128 | 18.7 ± 1.6 | 32 |
| NB-RLP860 | 15.5 ± 1.6 | 128 | 16.3 ± 0.3 | 32 |
| Zinc pyrithione | 0.20 ± 0.001 | 1 | 2.2 ± 0.3 | 4 |

Example 7: Sequencing of the *V. paradoxus* RKNM-096 Glycolipopeptide and Rhamnose Biosynthetic Gene Clusters To establish the genetic basis for the biosynthesis of the novel glycolipopeptide biosurfactants described here, the genome of *V. paradoxus* RKNM-096 was sequenced. *V. paradoxus* RKNM-096 was cultured in ISP2 broth and genomic DNA was isolated using the UltraClean® Microbial DNA Isolation Kit according to the manufacturer's recommendations (Mo Bio, Carlsbad, Calif., USA). The genome was sequenced at the McGill University and Genome Quebec Innovation Centre (Montreal, QC, CA) using 2 SMRT Cells in a PacBio RSII sequencer (Pacific Biosciences, Menlo Park, Calif., USA). A total of 140, 476 raw subreads with an average length of 11,269 bp were generated and genome assembly was achieved using a HGAP workflow (Chin et al. [2013] *Nature Methods* 10, 563). Briefly, raw subreads were generated from raw .bas.h5 PacBio data files. A subread length cutoff value (30×) was extracted from subreads and used in the preassembly (BLASR) step, which consists of aligning short subreads on long subreads (Chaisson and Tesler *BMC Bioinformatics* 13, 238). Since errors in PacBio reads are random, the alignment of multiple short reads on longer reads enables correction of sequencing errors on long reads. These long corrected reads were then used as seeds in a subsequent assembly prepared using the Celera assembler (Myers et al. [2000] *Science* 287, 2196), which generates contigs. These contigs were then 'polished' by aligning raw reads on contigs (BLASR) which were then processed through a variant calling algorithm (Quiver) that generates high quality consensus sequences using local realignments and PacBio quality scores (Chin et al. [2013] *Nature Methods* 10, 563). Over 161,717,463 bp of corrected long subreads were obtained and resulted in the assembly of two contigs. One contig contained 7,193,071 bp while the other contained 1,767 bp. The genome was annotated using the RAST server (Aziz et al. [2008] *BMC Genomics* 9, 75; Overbeek et al. [2014] *Nucleic Acid Res.* 42, D206; Brettin et al. [2015] *Sci Rep.* 5, 8265). The function of open reading frames (ORFS) identified by the RAST annotation were further explored by BLASTP (Altscul et al. [1997] *Nucleic Acids Res.* 25, 3389) and conserved domain (Marchler-Bauer and Bryant [2004] *Nucleic Acids Res.* 32, W327) analysis of deduced amino acid sequences.

Based on the structure of NB-RLP1006 it was hypothesized that its biosynthesis would require a NRPS to synthesize the dipeptide, one or more acyltransferases to acylate the peptide and generate the 3-(3-(3-hydroxydecanoyloxy) decanoyloxy) decanoyl moiety and one or more glycosyltransferases. Scanning the genome for genes encoding NRPSs identified two loci. One locus contained a single NRPS-encoding gene followed by two glycosyltransferases, thus this locus (12,721 bp) was analyzed further. Six ORFs were identified in this locus, which were predicted to play an integral role in glycolipopeptide biosynthesis (Table 3). The six genes, designated rlpA to rlpE, are oriented in the same direction and form a contiguous region in the *V. paradoxus* RKNM-096 genome.

TABLE 3

Deduced functions of Orfs identified in the *V. paradoxus* RKNM-096 glycolipopeptide (Seq. ID: 1) and dTDP-L-rhamnose biosynthetic gene clusters (Seq. ID: 2).

| Seq. ID. (DNA) | Source | Name | Start | Stop | Seq. ID. (protien) | Size (aa) | Proposed Function |
|---|---|---|---|---|---|---|---|
| 3 | Seq. ID: 1 | rlpA | 121 | 1035 | 4 | 304 | LysR transcriptional regulator |
| 5 | Seq. ID: 1 | rlpB | 1437 | 8912 | 6 | 2491 | Nonribosomal peptide synthetase |
| 7 | Seq. ID: 1 | rlpC | 8924 | 10243 | 8 | 439 | dTDP-rhamnosyl transferase |
| 9 | Seq. ID: 1 | rlpD | 10276 | 10488 | 10 | 70 | MbtH protein |
| 11 | Seq. ID: 1 | rlpE | 10497 | 11465 | 12 | 322 | dTDP-rhamnosyl transferase |
| 13 | Seq. ID: 1 | rlpF | 11462 | 12721 | 14 | 419 | MFS transporter |
| 15 | Seq ID: 2 | rmlB | 299 | 1378 | 16 | 359 | dTDP-glucose 4,6-dehydratase |
| 17 | Seq ID: 2 | rmlD | 1375 | 2265 | 18 | 296 | dTDP-4-dehydrorhamnose reductase |
| 19 | Seq ID: 2 | rmlA | 2298 | 3194 | 20 | 298 | Glucose-1-phosphate thymidylyltransferase |
| 21 | Seq ID: 2 | rmlC | 3191 | 3736 | 22 | 181 | dTDP-4-dehydrorhamnose 3,5-epimerase |

Genes involved in regulation. The first gene, rlpA, encodes a protein that exhibits similarity to transcriptional regulators belonging to the LysR family. Conserved domain analysis indicated that RlpA contained an amino-terminal helix-turn-helix domain and a carboxy-terminal LysR substrate binding domain, which is consistent with the domain architecture of LysR transcriptional regulators. This family of regulators can function as transcriptional activators or repressors (Maddocks and Oyston [2009] *Microbiology* 154, 3609), thus it is likely that RlpA plays a role in the regulation of glycolipopeptide biosynthesis.

Genes involved in peptide biosynthesis. Following rlpA is large gene, rlpB, (7,476 bp), which encodes a NRPS. Domain analysis (Bachmann and Ravel [2009] *Meth. Enzymol.* 458, 181) indicated that that the NRPS consists of two modules (M1 and M2) with the following domain organization $(C\text{-}A\text{-}PCP)_{M1}$-$(C\text{-}A\text{-}PCP\text{-}R)_{M2}$. The dimodular structure and domain organization suggests that RlpB generates a dipeptide, which is consistent with structure of the *V. paradoxus* RKNM-096 glycolipopeptides. The first domain of the first module of RlpB is a condensation domain. The presence of a C-domain at the beginning of a NRPS initiation module is characteristic of acylated peptides. Amino-terminal C-domains can catalyze amide bond formation between the first amino acid of a peptide and a fatty acid. The fatty acid can be presented to the C-domain as an acyl-ACP intermediate, as in the case of CDA biosynthesis (Kopp et al. [2008] *J. Am. Chem. Soc.* 130, 2656), or an acyl-CoA intermediate, as in the case of surfactin biosynthesis (Krass et al. *Chem. Biol.* 17, 872). A phylogenetic analysis of the RlpB initiation module C-domain (residues 12-437) was conducted using the NaPDoS program (Ziemert et al. [2012]*PLoS One* 7, e34064). The RlpB domain clustered closely with C-domains from initiation modules that catalyze the condensation of a fatty acid precursor with an amino acid. The most closely related C-domain in the NaPDoS reference database was the initiation module of the bacillibactin NRPS (38% identity), which catalyzes the condensation of 2,3-dihydroxybenzoyl-ACP with glycine (May et al. [2001] *J. Biol. Chem.* 278, 7209). This suggests that glycolipopeptide biosynthesis starts with the condensation of a fatty acid with the first amino acid of the peptide (serine). Similar analysis of the second C-domain indicated it was most closely related to the second C-domain of the bacillibactin dimodular NRPS, DhbF (54% identity). Phylogenetic analysis revealed that the M2 C-domain of RlpB clustered with C-domains catalyzing the condensation of two L-amino acids (Ziemert et al. [2012]*PLoS One* 7, e34064), which is consistent with the glycolipopeptide structure.

To predict the substrate specificity of the RlpB A-domains, the substrate specificity codes were extracted from the A-domain active sites (8 residues between motifs A3 and A6) and compared to known A-domain specificity codes using the NRPS Predictive Blast tool (Bachmann and Ravel [2009] *Meth. Enzymol.* 458, 181). The specificity code of the M1 A-domain was most similar to A-domains from the nostopeptolide, pyoverdin, CDA and enterobactin NRPSs that activate L-serine (75-87% identity, 87-100% similarity, E-value 0.023-0.039), suggesting that L-serine is incorporated by M1. This observation is consistent with the structure of the glycolipopeptides. The M2 A-domain specificity code showed low homology (50% identity, 100% similarity, E-value 0.98) to an A-domain of the tyrocidine NRPS (TycB), which activates L-phenylalanine or L-tryptophan (Mootz and Marahiel [1997] *J. Bacteriol.* 179, 6843). This low level of similarity precludes prediction of the substrate specificity of this A-domain. Based on the structure of the *V. paradoxus* RKNM-096 glycolipopeptides the second A-domain would be expected to activate L-leucine. Comparison of the A-domain specificity code of RlpB module 2 to leucine specificity codes (Stachelhaus et al. [1999] *Chem. Biol.* 6, 493) also revealed low similarity, thus the RlpB M2 A-domain specificity code may represent a novel variant for leucine, although biochemical evidence would be need to establish the substrate specificity of this domain. The PCP domains of RlpB were also analyzed and both were found to contain the core PCP domain motif with an invariant serine which represents the 4'-phosphopantetheine attachment site (Konz and Marahiel *Chem. Biol.* 6, R39).

The final domain of RlpB is an R-domain. R-domains utilize NAD(P)H as a co-factor to reductively release PCP-bound final products as an aldehyde or alcohol (Du and Lou [2010] *Nat. Prod. Rep.* 27, 255). The presence of a leucinol residue at the carboxy-terminus of the glycolipopeptide dipeptide moiety is consistent with release of an acylated dipeptide intermediate by an R-domain. Collectively, the domain structure and organization of RlpB, as well as the predicted substrate specificity of the individual domains are consistent with the structure of the glycolipopeptides produced by *V. paradoxus* RKNM-096.

A small gene (rlpD) encoding a 70 amino acid protein that shows similarity to MbtH-like proteins was found downstream of rlpB. These proteins are often found in association with NRPSs and have been demonstrated to be essential for non-ribosomal peptide the production. (Baltz [2014] *J. Ind. Microbiol. Biotechnol.* 41, 357). Recently these proteins have been shown to facilitate adenylation reactions via direct interaction with A-domains (Herbst et al. [2013] *J. Biol. Chem.* 288, 1991). Thus we predict that RlpD interacts with one or both A-domains of RlpB to facilitate dipeptide formation.

Genes involved in glycosylation. Glycosylation of the acylated dipeptide generated by RlpB is likely catalyzed by two ORFs (rlpC and E) downstream of rlpB. The deduced amino acid sequence of rlpC (439 aa) shows similarity to the GT1 family of glycosyltransferases, which utilize activated sugars as substrates to transfer sugar moieties to a diverse array of acceptor molecules (Breton et al. [2006] *Glycobiology* 16, 29R). The deduced amino acid sequence of rlpE (322 aa) shows similarity to dTDP-rhamnosyltransferases. In rhamnolipid biosynthesis two glycosyltransferases are utilized to sequentially transfer two rhamnosyl units to the lipid component of rhamnolipid (Deziel et al. [2003] *Microbiology* 149, 2005). RhlB transfers rhamnose from dTDP-L-rhamnose to the free β-hydroxyl group of 3-(3'-hydroxydecanoyloxy)decanoic acid (HDD) to generate mono-RL, while di-RL is formed by the transfer of an additional rhamnose from dTDP-L-rhamnose to mono-RL by RhlC (Abdel-Mawgoud et al. [2011] in *Biosurfactants*, Springer-Verlag, Berlin Heidelberg). The relationship between RlpC and RlpE and the RhlB and RhlC homologs from *P. aeruginosa* PAO1, *B. thialandensis* E264 and *B. psuedomallei* 1710B was investigated via the generation of a phylogenetic tree (unweighted pair group method with arithmetic mean method). In this analysis RlpC clustered with the RhlB orthologs while RlpE clustered with the RhlC orthologs. While RlpC clustered with the RhlB orthologs, it did not cluster tightly as it showed limited sequence identity with these enzymes (18.6-23.1%). In contrast, RlpE shared between 39.6-40.7% identity with the RhlC orthologs. This data suggests that RlpC and RlpE perform similar functions as RhlB and RhlC, respectively. We hypothesize that RlpC catalyzes the rhamnosylation of an acylated dipeptide intermediate utilizing dTDP-L-rhamnose as the carbohydrate donor. The limited sequence homology between RlpC and the RhlB orthologs may reflect the significant difference in glycosylation substrates utilized by the enzymes. RlpE is predicted to catalyze the second glycosylation reaction, transferring rhamnose from dTDP-L-rhamnose to the RlpC reaction product.

Genes encoding dTDP-L-rhamnose biosynthesis were not found in close proximity to the glycolipopeptide gene cluster. Scanning the genome for homologs of *P. aeruginosa* PAO1 rhamnose biosynthetic genes (rmlBDAC) identified four genes that exhibited strong sequence similarity to those from *P. aeruginosa* (identity/similarity: RmlB-79%/89%, RmlD-60%/71%, RmlA-78%/89%, RmlC-66%/80%). In the *V. paradoxus* RKNM-096 genome the four genes are clustered and are found in the same order as in *P. aeruginosa* (rmlBDAC) (Rahim et al. [2000] *Microbiology* 146, 2803). This locus likely provides the dTDP-L-rhamnose substrates utilized by RlpC and RlpE. Modulation of expression of one or more components of the dTDP-L-rhamnose biosynthetic pathway by one skilled in the art may be an effective approach to increase glycolipopeptide yields.

Genes involved in transport. Directly downstream of rlpE is an ORF (rlpF) encoding a protein, which is similar to major facilitator superfamily transporters from a variety of bacteria. RlpF exhibits 38% identity and 54% similarity to PA1131 from *P. aeruginosa* PAO1, which is immediately upstream of rhlC (Dubeau [2009] *BMC Microbiol* 9, 263). RlpF is likely involved in glycolipopeptide efflux.

Genes involved in the biosynthesis of the lipid moiety. In rhamnolipid biosynthesis the HDD moiety is produced by RhlA, which condenses two β-hydroxydecanoyl-ACP molecules from fatty acid biosynthesis to yield 3-(3'-hydroxydecanoyloxy)decanoic acid. Scanning of the *V. paradoxus* RKNM-096 genome for RhlA homologs did not identify any proteins with significant similarity to RhlA. Thus generation of the lipid moiety of the RKNM-096 glycolipopeptides is likely directed by a novel, yet to be identified mechanism.

Genes involved in glycolipopeptide acetylation. Acetylated analogues of NB-RLP1006 are abundant in *V. paradoxus* RKNM-096 fermentation broths. No genes encoding acetyltransferases were identified in the gene cluster. Thus it is likely that acetylation is catalyzed by an enzyme encoded elsewhere in the *V. paradoxus* RKNM-096 genome.

Proposed biosynthesis. Glycolipopeptide biosynthesis presumably starts with the formation of the 3-(3-(3-hydroxydecanoyloxy)decanoyloxy)decanoyl moiety via a yet to be identified mechanism. After formation of the lipid moiety it is likely presented to the C-domain of RlpB M1 which condenses the lipid moiety with L-serine. RlpB M2 then incorporates L-leucine to form a PCP-bound acylated dipeptide intermediate which is released from the enzyme by the C-terminal R-domain of RlpB, resulting in the formation of a terminal L-leucinol residue. dTDP-L-Rhamnose, produced by the rmlBDAC operon, is then utilized by the rhamnosyltransferases RlpC and RlpE to sequentially glycosylate the aglycone resulting in the production of the final glycosylated glycolipopeptide NB-RLP1006. NB-RLP1006 would serve as a substrate for acetylation to form NB-RLP1048A and NB-RLP1048B.

Figure 2:
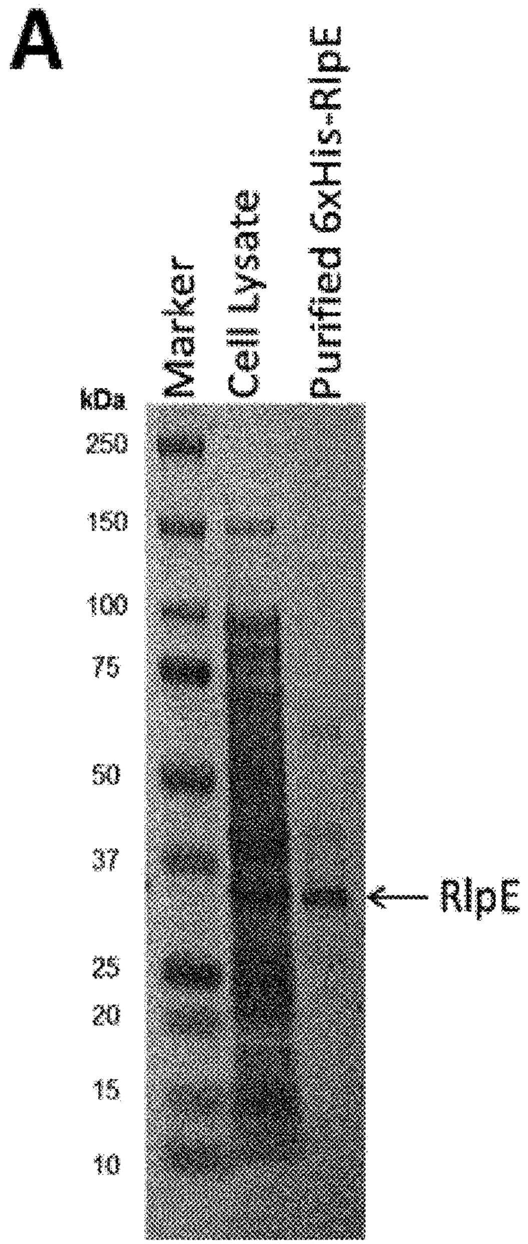
FIG. 2 is a denaturing polyacrylamide gel showing purified His-tagged RlpE (A) and the UPLC-HRMS analysis of enzyme reactions in which the enzyme was incubated with NB-RLP860 and dTDP-L-rhamnose.
Figure 2:
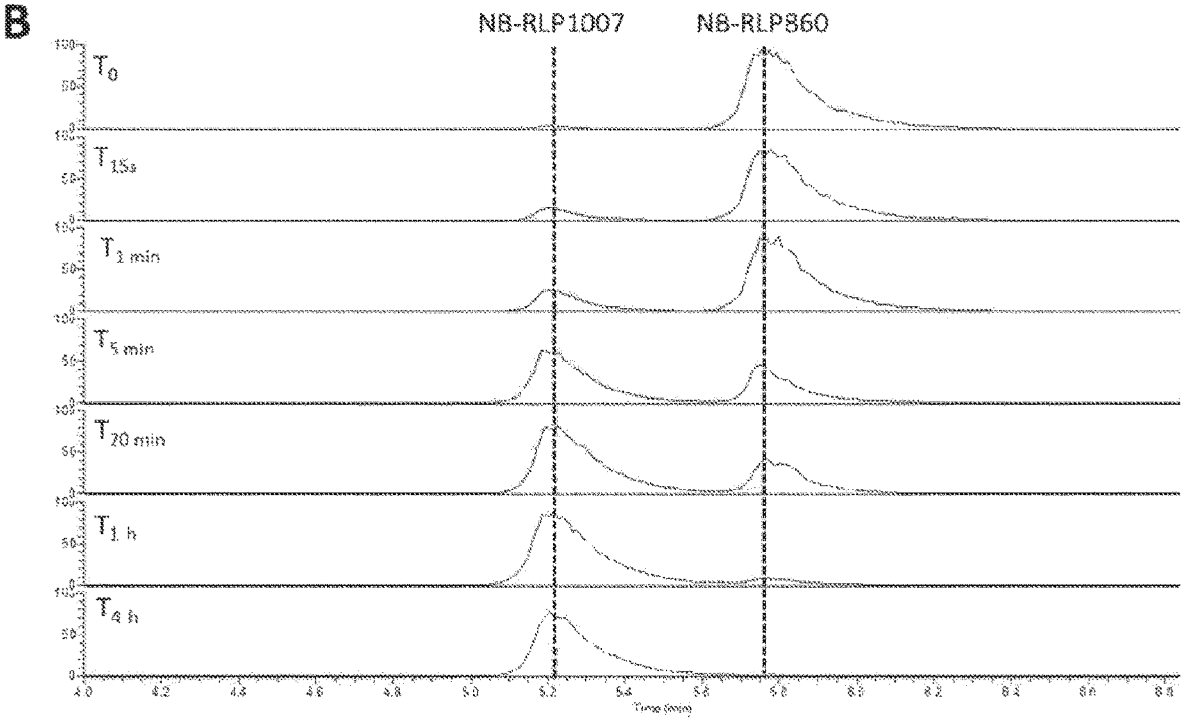

To prove the involvement of the rlpA-rplF gene cluster in the biosynthesis of glycolipopeptides in *V. paradoxus* RKNM-096 rlpE was expressed in *E. coli* and the activity of the enzyme demonstrated using NB-RPL860 as a substrate. Bioinformatics analysis indicated RlpE catalyzes the second rhamnosylation in glycolipopeptide biosynthesis, converting mono-rhamnosylated glyclipopeptides (e.g. NB-RLP832 and NB-RLP860) to di-rhamnosylated glycolipopeptides (e.g. NB-RLP978 and NB-RLP1006). The rlpE gene was cloned in pET28a (EMD Millipore, Darmstadt, DE) with an amino-terminal hexa-histidine tag using standard cloning techniques and mutation-free cloning was verified by sequencing. Due to the high GC content of rlpE, *E. coli* Rossetta DE3 pLysS (EMD Millipore) was chosen as the expression host as this strain expresses tRNAs for rare GC-rich codons (AGG, CCA, GGA). A single colony was used to inoculate 50 mL of LB Miller (EMD Millipore) supplemented with 50 μg/mL of kanamycin (Sigma-Aldrich) and 34 μg/mL of chloramphenicol (Sigma-Aldrich) and the flask was incubated at 37° C. with shaking at 250 rpm overnight. Expression cultures (50 mL) were performed in LB Miller supplemented with kanamycin and chloramphenicol. These cultures were inoculated with 0.5 mL of the overnight culture and cultured at 37° C. and 250 rpm until the optical density (600 nm) reached 0.5, following which IPTG was added to a final concentration of 1.0 mM to induce protein expression and the cultures were incubated at 15° C. for 24 h. Cells were harvested by centrifugation (6 000×g for 5 min) and washed once with 20 mM Tris-HCl (pH 8.0). The cell pellet was frozen at −80° C. until purification could be performed. To purify His-tagged RlpE, the cells were thawed, suspended in lysis buffer (500 mM NaCl, 5% glycerol, 1% Triton X-100, 25 mM Tris-HCl, pH 8.0) and then lysed via sonication. Cell debris and insoluble protein was removed by centrifugation at 15 000×g for 30 min. The supernatant was mixed with 0.5 mL of HisPur Ni-NTA resin (Thermo Fisher Scientific). The resin was washed six times with 1.0 mL of 75 mM imidazole. His-tagged RlpE was eluted with 1.0 mL of 250 mM imidazole. Four batch elutions were performed and pooled. The imidazole elution buffer was exchanged with enzyme buffer (25 mM Tris-HCl, 10% glycerol) and concentrated by centrifugal filtration using a Macrosep 3 kDa spin filter (Pall). Following concentration the enzyme was aliquoted and stored at −80° C. The purity of the enzyme was analyzed by denaturing polyacrylamide gel electrophoresis (4-15% Mini-PROTEAN precast gel, 160 V, 30 min; Bio-Rad). The calculated molecular weight of His-tagged RlpE was 38.2 KDa. The apparent molecular weight of the purified protein was 33.05 kDa, which was in good agreement with the expected molecular weight (FIG. 2A).

The activity of RlpE was established by incubating the enzyme (0.1 μM) in reaction buffer (25 mM Tris-HCl pH 8.0, 2.5 mM $MgCl_2$) with 1 mM of TDP-L-rhamnose and 0.5 mM NB-RLP860. Reactions (200 μL) were incubated at 30° C. for 4 h. A portion (25 μL) of the reaction was removed at 15 s, 1 min, 5 min, 20 min, 1 h and 4 h. The reaction was stopped by the addition of two volumes of methanol followed by flash freezing. Quenched reactions were separated by UPLC (Accela™, Thermo Fisher Scientific Mississauga, ON, Canada) and the eluates analyzed by HRESIMS (LTQ Orbitrap Velos; Thermo Fisher Scientific) (positive mode, monitoring m/z 200-2000). Chromatographic separation was achieved with a Hypersil Gold 1.9 μm $C_{18}$ 175 Å 50×2.1 mm column (thermo Fisher Scientific) and a linear gradient from 50% $H_2O$/0.1% FA (solvent A) and 50% acetonitrile ($CH_3CN$)/0.1% FA (solvent B) to 100% solvent B over 5 min followed by a hold of 100% solvent B for 3 min with a flow rate of 300 μL/min. Reactions conducted with boiled enzyme showed no conversion of NB-RLP860 to NB-RLP1006. In contrast, enzyme reactions containing intact 6×His-RlPE resulted in the complete conversion of NB-RLP860 to NB-RLP1006 after 4 h (FIG. 2B). This data indicates that RlpE catalyzes the second rhamnosylation step in glycolipopeptide biosynthesis in *V. paradoxus* RKN-096. As genes for the biosynthesis of natural products in bacteria are typically clustered, this finding also provides strong evidence confirming the proposed gene cluster as the locus responsible for glycolipopeptide biosynthesis.

We also explored the ability of purified 6His-RlpE to iteratively add rhamnose units to NB-RLP860 by scanning the HRMS data for masses consistent with glycolipopeptide surfactants containing three rhamnose residues (calc'd $[M+H]^+$ 1153.7204), four rhamnose residues (calc'd $[M+H]^+$ 1299.7783) and five rhamnose residues (calc'd $[M+H]^+$ 1153.7204). Masses consistent with trirhamnosylated and tetrarhamnosylated reaction products were obtained and differed from the expected molecular weights by <1.03 parts per million (ppm) and <0.6 ppm, respectively. Interestingly, two peaks were observed for each mass, suggesting additional rhamnose units are attached at two different positions of the NB-RLP1006 structure. Relative to the production of NB-RLP1006 the tri-rhamnosylated and tetra-rhamnosylated glycolipopeptides constituted 2.99% and 0.14% of the reaction products. No penta-rhamnosylated glycolipopeptides were detected. This data indicates that recombinantly expressed RlpE can be used to generate glycolipopeptide analogs with up to four rhamnose residues. Such modifications may alter the functional properties of the glycolipopeptide. The properties can include but are not limited to wetting, foaming, surfactancy and emulsification.

Elucidation of the biosynthetic pathway for the glycolipopeptide biosurfactants produced by *V. paradoxus* RKNM-096 sets the stage for rational modification of the biosynthetic pathway to generate novel analogues or to increase yields. Analogues may be generated by those skilled in the art via modification of the enzymes responsible for the biosynthesis and incorporation of the lipid, peptide and carbohydrate portions of the molecule. Yields can be increased by those skilled in the art by modification of regulatory genes and or promoters, by overexpressing enzymes that represent rate limiting steps in the biosynthetic pathway or by inactivating enzymes which perform undesirable reactions. Knowledge of the biosynthetic pathway also enables expression in a heterologous host, which may enable yield improvements or the generation of glycolipopeptide analogues.

Example 8: Identification of Related Biosurfactants in Other Bacteria

Sequencing of the *V. paradoxus* RKNM-096 glycolipopeptide and rhamnose biosynthetic gene clusters was performed. Prior to the discovery of the glycolipopeptide series of biosurfactants and the associated biosynthetic gene cluster described herein, it would not have been possible to accurately predict the production of related glycolipopeptide biosurfactants based solely on DNA sequence analysis. Identification of the glycolipopeptide biosynthetic gene cluster now allows for targeted interrogation of microbial genomes for related gene clusters, which may have the potential to produce novel glycolipopeptide biosurfactants. As rlpC encodes a novel rhamnosyltransferase, which glycosylates an acylated dipeptide intermediate characteristic of the glycolipopeptide class of biosurfactants, we used the deduced amino acid sequence of this gene to search available bacterial genomes for homologs. This search identified homologs exhibiting to RlpC from a wide variety of bacteria. We then investigated genomic regions flanking the genes encoding the RlpC homologs for the presence of homologs of the other glycolipopeptide biosynthetic genes. Two examples will be presented to demonstrate the utility of using sequences from the glycolipopeptide gene cluster as probes to discover producers of putatively novel biosurfactants.

Figure 3:
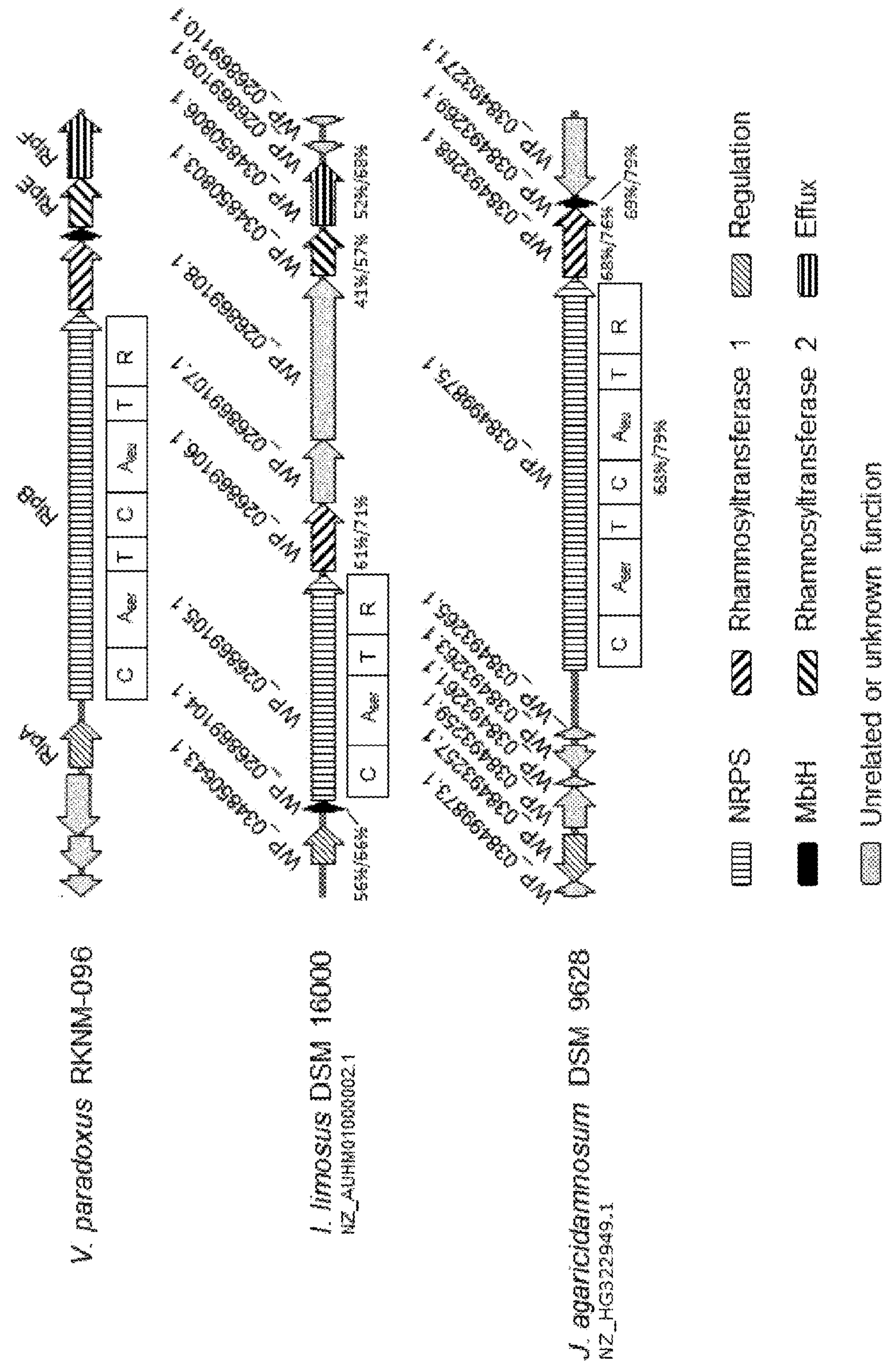
FIG. 3 is a schematic comparison of the *V. paradoxus* RKNM-096 glycolipopeptide gene cluster to homologous gene clusters identified in *I. limosus* DSM 16000 and *J. agaricidamnosum* DSM 9628. Genes encoding proteins homologous to proteins in the *V. paradoxus* gene cluster are indicated by arrow filling patterns. Identity and similarity to *V. paradoxus* proteins is indicated under arrows (identity %/similarity %). NRPS domain organization is indicated under arrows representing genes encoding non-ribosomal peptide synthetases (NRPSs). Domains: C—condensation, A—adenylation, T—thiolation/peptidyl-carrier protein, R—reductase. Subscript notation indicates putative A-domain substrate. Labels above arrows in the *I. limosus* and *J. agaricidamnosum* gene clusters indicate protein IDs.

A homologous gene cluster was identified in the *Janthinobacterium agaricidamnosum* DSM 9628 genome (GenBank accession no. NZ_HG322949.1) (FIG. 3). *J. agaricidamnosum* is a beta-proteobacterium like *V. paradoxus*, but belongs to a different family. The RlpC homolog in this strain (WP_038493268.1) exhibited 68% identity to RlpC. Scanning the genome around the RlpC homolog identified other homologs of genes present in the glycolipopeptide gene cluster. Directly downstream of the RlpC homolog was an MtbH-like protein (WP_038493269.1) which shared 69% identity with RlpD. Upstream a dimodular NRPS was identified (WP)038499875.1), which showed 68% identity to RlpB and contained an identical domain organization ($[C\text{-}A\text{-}PCP]_{M1}$-$[C\text{-}A\text{-}PCP\text{-}R]_{M2}$). Active site analysis (Bachmann and Ravel [2009] *Meth. Enzymol.* 458, 181) indicated that the predicted substrate specificity also matched that of RlpB, with the M1 A-domain specificity code matching that for L-serine and the M2 A-domain specificity code matching that of the M2 A-domain of RlpB, indicating L-leucine is incorporated by M2 (FIG. 3). A C-domain and R-domain were also found at the amino and carboxy-termini of the *J. agaricidamnosum* NRPS, respectively. This suggests that biosynthesis is initiated by condensation of an acyl intermediate with serine, and terminated by reductive release of an acylated dipeptide, similar to what is predicted for glycolipopeptide biosynthesis in *V. paradoxus* RKNM-096. No homolog to RlpE was found in the *J. agaricidamnosum* DSM 9628 gene cluster, indicating that the product of the cluster likely contains a single rhamnose residue. A gene cluster with a highly similar organization to that in *J. agaricidamnosum* DSM 9628 was also detected in the genome of *V. paradoxus* DSM 21786 (GenBank accession no. NC_022247.1). Collectively, this data suggests that *J. agaricidamnosum* DSM9628 and *V. paradoxus* DSM 21786 possess the ability to produce novel biosurfactants with structures related to those produced by *V. paradoxus* RKNM-096. Based on the bioinformatics analysis presented here, we predict the compound(s) produced by these bacteria would be a N-acylated L-serinyl-L-leucinol dipeptide bearing a single rhamnose residue.

Genome scanning using the RlpC sequence also identified a putative biosurfactant gene cluster in the more distantly related alpha-proteobacterium *Inquilinus limosus* DSM 16000 (Genbank accession no. NZ_AUHM01000002.1) (FIG. 3). The RlpC homolog (WP_026869107.1) in *I. limosus* shared 61% identity with the *V. paradoxus* RKNM-096 protein. Genes encoding a MtbH-like protein (WP_026869104.1) and a NRPS (WP026869105.1) were identified immediately upstream of the RlpC homolog. The MbtH-like protein shared 56% identity with RlpD. The NRPS was a monomodular enzyme with the following domain organization: C-A-T-R (FIG. 3). Active site analysis of the A-domain (Bachmann and Ravel [2009] *Meth. Enzymol.* 458, 181) indicated that L-serine is the likely substrate of this enzyme. The presence of a C-domain at the N-terminus and an R-domain at the C-terminus suggests that the product of the NRPS is an acylated serinol. An RlpE homolog (WP_034850803.1) was also detected in the *I. limosus* gene cluster (41% identity) suggesting that the acylated serinol intermediate may be sequentially glycosylated to yield a product bearing a dirhamnosyl moiety similar to NB-RLP1006. The final product may be exported out of the cell via the action of a MFS exporter (WP_034850806.1) which shares 52% identity with RlpF.

To validate our in silico approach to identifying producers of glycolipopeptide biosurfactants we obtained *J. agaricidamnosum* DSM 9628 and *V. paradoxus* DSM 21786 from the Deutsche Sammlung von Mikroorganismen und Zellkulturen (DSMZ) culture collection. Each strain was fermented in a variety of culture media to promote production of predicted biosurfactants. Fermentations were extracted twice with an equal volume of EtOAc. The organic layer was evaporated and the resulting concentrated extracts were analyzed by UPLC-PDA-ELSD-HRESIMS as described above for NB-RLP1006 (Example 3). Three prominent peaks eluting at 3.07, 5.05 and 5.51 min were observed in the ELSD and HRESIMS chromatograms of *J. agaricidamnosum* DSM 9628. The peak at 3.07 min (HRESIMS m/z 1182.6217 $[M+H]^+$, calcd for $C_{56}H_{85}N_{12}O_{16}$, 1181.6201) could be attributed to the known compound jagaracin previously reported from this strain (Graupner et al. [2012] Angew Chem. Int. Ed. Engl. 51:13173). Extraction of the mass spectra for peaks eluting at 5.05 and 5.51 min revealed $[M+H]^+$ ions of m/z 833.5741 and m/z 861.6033, respectively. The observed $[M+H]^+$ ions showed a −1.5 and 1.0 ppm mass difference from predicted m/z $[M+H]^+$ ions for the monorhamnosyl glycolipopeptides NB-RLP832 (m/z 833.5741 $[M+H]^+$) and NB-RLP860 (m/z 861.6033 $[M+H]^+$), respectively, indicating the expected compounds had been produced by *J. agaricidamnosum* DSM 9628. Similar to NB-RLP978A-C and NB-RLP1020A-C, the mass of NB-RLP832 closely matched that predicted for an analogue of NB-RLP860 lacking two methylene groups. These compounds were purified and their structures elucidated using a combination of 1D and 2D NMR experiments. This analysis unambiguously confirmed that the expected monorhamnosylated biosurfactant had been produced by *J. agaricidamnosum* DSM 9628 (see Example 3).

Identical analysis of *V. paradoxus* DSM 21786 fermentation extracts also revealed the presence of a peak eluting at 5.51 min in the HRESIMS chromatogram. Inspection of the mass spectrum associated with this peak revealed the presence of a $[M+H]^+$ ion with a m/z of 861.6104, which differed from the expected mass ($[M+H]^+$ m/z 861.6046) by 5.8 ppm. The identical retention time and monoisotopic mass indicated that both *J. agaricidamnosum* DSM 9628 and *V. paradoxus* DSM 21786 produce NB-RLP860.

What is claimed:

1. A method of preparing biosurfactants containing rhamnose moieties, comprising adding at least one rhamnose moiety to a biosurfactant with recombinantly expressed RIpE, wherein the RIpE is a rhamnosyltransferase enzyme which catalyses a rhamnosylation reaction between the rhamnose moiety and the biosurfactant, wherein the biosurfactant comprises a hydrophobic lipid component comprising a hydroxyl end, wherein the lipid component is covalently linked to a carbohydrate moiety comprising at least one rhamnose moiety at the hydroxyl end of the lipid component attached via a glycosidic linkage, and wherein the RIpE has an amino acid sequence identity of at least 95% with SEQ ID NO: 12 or an amino acid sequence identity of at least 95% with SEQ ID NO: 24.

2. The method of claim 1, wherein the hydrophobic lipid component further comprises a carboxyl end, wherein the lipid component is further covalently linked to a peptide chain at the carboxyl end of the lipid component.

3. The method of claim 2, wherein the peptide chain comprises in a range of between 2 and 10 amino acids.

4. The method of claim 1, wherein the lipid component comprises in a range of between 1 and 6 alkanoic acid moieties.

5. The method of claim 1 wherein the lipid component comprises an acyl chain, and wherein the length of each said acyl chain is in a range of between $C_4$ to $C_{20}$.

6. The method of claim 1, wherein the carbohydrate moiety may comprise at least one acetyl group.

7. The method of claim 2, wherein the peptide chain comprises a serine-leucinol dipeptide.

8. The method of claim 2, wherein the lipid component comprises three β-hydroxyalkanoic acid moieties.

9. The method of claim 5, wherein the length of each acyl chain of the lipid component is $C_{10}$.

10. The method of claim 1, wherein the carbohydrate moiety comprises one rhamnose moiety attached to the lipid component via a glycosidic linkage.

11. The method of claim 1, wherein the carbohydrate moiety comprises two rhamnose moieties attached to the lipid component via a glycosidic linkage.

12. The method of claim 1, wherein the lipid component comprises three β-hydroxyalkanoic acid moieties, the length of each acyl chain of the lipid component is $C_{10}$, and the carbohydrate moiety comprises a rhamnose moiety attached to the lipid component via a glycosidic linkage.

13. The method of claim 2, wherein the biosurfactant comprises the structure:

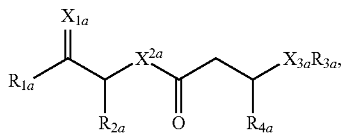

wherein $R_{1a}$ is selected from the group consisting of H, OH, $OCH_3$, SH, $S(CH_3)$, $NH_2$, $NH(CH_3)$, $N(CH_3)_2$, and a peptide chain having the structure:

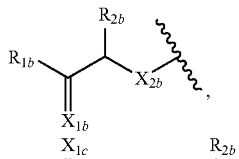

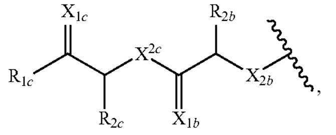

and

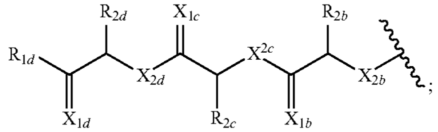

wherein $R_{1b}$, $R_{1c}$, and $R_{1d}$, are selected from the group consisting of H, OH, $OCH_3$, SH, $S(CH_3)$, $NH_2$, $NH(CH_3)$, and $N(CH_3)_2$;

$R_{2a}$, $R_{2b}$, $R_{2c}$, and $R_{2d}$ are each independently an amino acid side chain;

$X_{1a}$, $X_{1b}$, $X_{1c}$, and $X_{1d}$ are each independently selected from the group consisting of one oxygen atom and two hydrogen atoms;

$X_{2a}$, $X_{2b}$, $X_{2c}$, and $X_{2d}$ are each independently selected from the group consisting of NH, $N(CH_3)$, and O;

$R_{3a}$ is selected from the group consisting of a carbohydrate portion, and a lipid selected from the group consisting of a monomer having the structure:

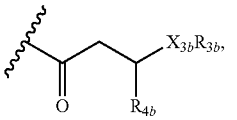

and an oligomer selected from the group consisting of:

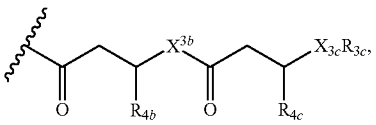

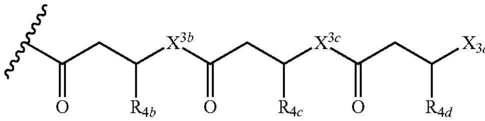

wherein $X_{3a}$, $X_{3b}$, $X_{3c}$, and $X_{3d}$ are each independently selected from the group consisting of NH, $N(CH_3)$, and O;

$R_{3a}$, $R_{3b}$, $R_{3c}$, and $R_{3d}$ comprises a carbohydrate portion comprising a monomer selected from the group consisting of:

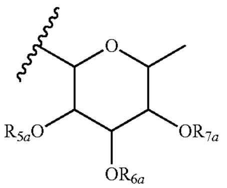

and

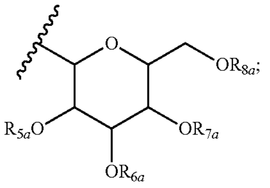

wherein $R_{5a}$, $R_{6a}$, $R_{7a}$, and $R_{8a}$ are each independently selected from the group consisting of a hydrogen atom, methyl, acetyl, and a carbohydrate; and $R_{4a}$, $R_{4b}$, $R_{4c}$, and $R_{4d}$ are each independently selected from the group consisting of a hydrogen atom, methyl, and a $C_2$ to $C_{19}$ saturated or unsaturated linear, branched-chain, cyclic, or aromatic hydrocarbon groups.

14. The method of claim 13, wherein at least one of $R_{6a}$, $R_{7a}$, and $R_{8a}$ comprises a carbohydrate comprising a monomer selected from the group consisting of:

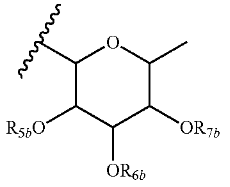

and

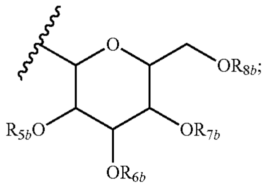

wherein $R_{5b}$, $R_{6b}$, $R_{7b}$, and $R_{8b}$ are each independently selected from the group consisting of a hydrogen atom, methyl, acetyl, and a carbohydrate.

15. The method of claim 13, wherein the peptide chain comprises at least one proline monomer having the structure:

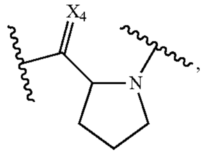

wherein $X_4$ is selected from the group consisting of one oxygen atom and two hydrogen atoms.

16. The method of claim 13, wherein the peptide chain comprises a single proline monomer or a terminal proline monomer having the structure:

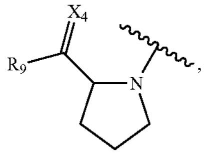

wherein $R_9$ is selected from the group consisting of H, OH, $OCH_3$, SH, $S(CH_3)$, $NH_2$, $NH(CH_3)$, and $N(CH_3)_2$; and $X_4$ is selected from the group consisting of one oxygen atom and two hydrogen atoms.

17. The method of claim 1, wherein the biosurfactant has the structure:

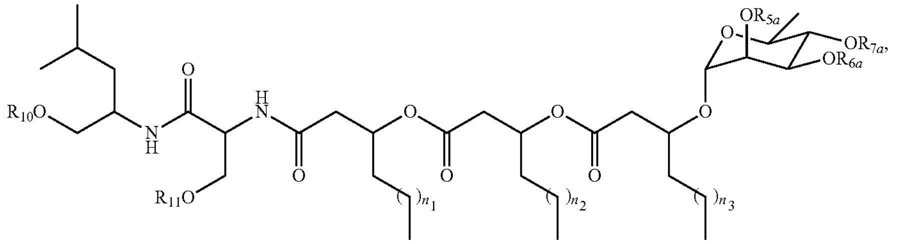

wherein $R_{5a}$, $R_{6a}$, $R_{7a}$, $R_{10}$, and $R_{11}$ are each independently selected from the group consisting of a hydrogen atom and acetyl; and $n_1$, $n_2$, and $n_3$ are integers each independently selected from 1 to 7.

18. The method of claim 1, wherein the biosurfactant has the structure:

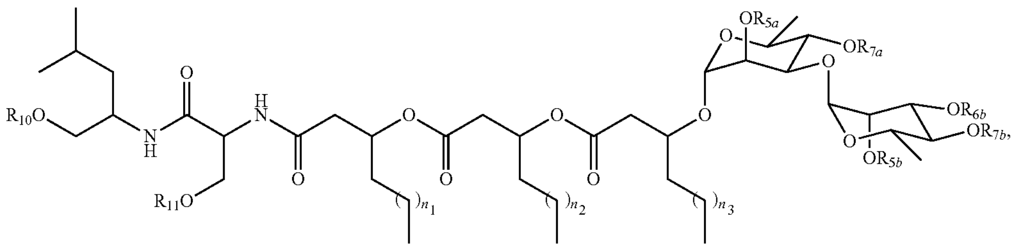

wherein $R_{5a}$, $R_{5b}$, $R_{6b}$, $R_{7a}$, $R_{7b}$, $R_{10}$, and $R_{11}$ are each independently selected from the group consisting of a hydrogen atom and acetyl; and $n_1$, $n_2$, and $n_3$ are integers each independently selected from 1 to 7.

19. The method of claim 1, wherein the biosurfactant has the structure:

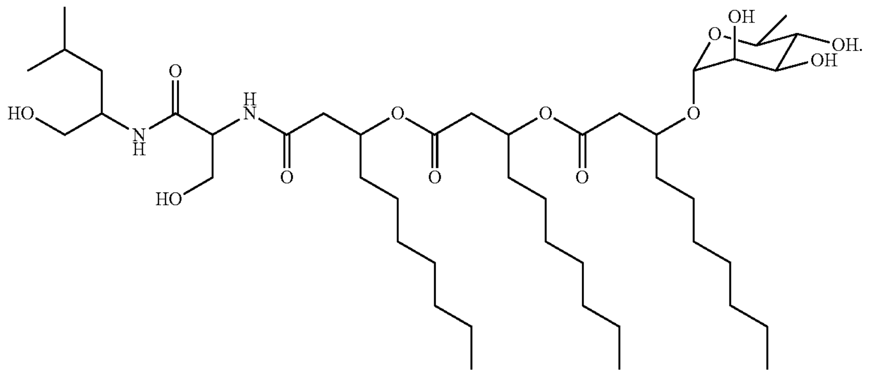 [SMILES: CCCCCCCC(CC(=O)NC(CO)C(=O)NC(CO)CC(C)C)OC(=O)CC(CCCCCCC)OC(=O)CC(CCCCCCC)OC1OC(C)C(O)C(O)C1O]

20. The method of claim 1, wherein the biosurfactant has the structure:

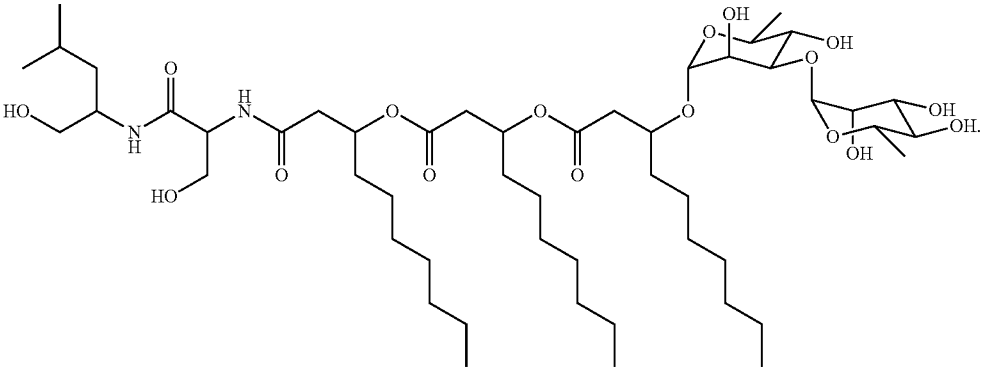 [SMILES: CCCCCCCC(CC(=O)NC(CO)C(=O)NC(CO)CC(C)C)OC(=O)CC(CCCCCCC)OC(=O)CC(CCCCCCC)OC1OC(C)C(O)C(OC2OC(C)C(O)C(O)C2O)C1O]

21. The method of claim 1, wherein the biosurfactant has the structure:

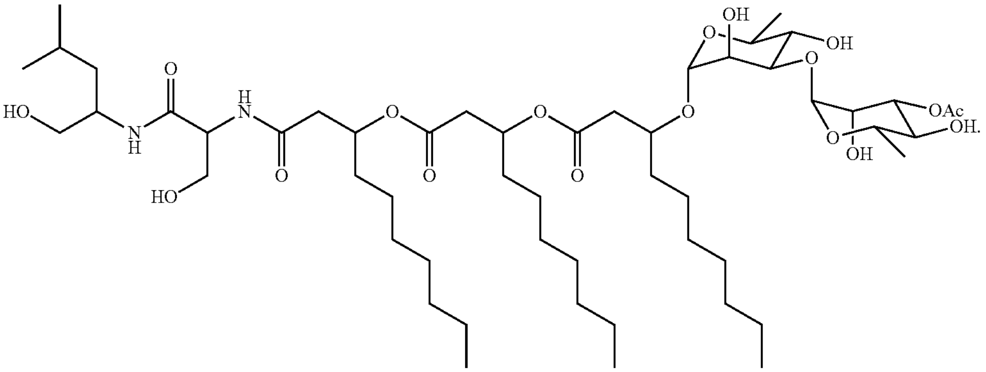 [SMILES: CCCCCCCC(CC(=O)NC(CO)C(=O)NC(CO)CC(C)C)OC(=O)CC(CCCCCCC)OC(=O)CC(CCCCCCC)OC1OC(C)C(O)C(OC2OC(C)C(O)C(OC(C)=O)C2O)C1O]

22. The method of claim 1, which includes adding one to four rhamnose moieties to the biosurfactant.

23. The method of claim 1, wherein the RlpE adds said at least one rhamnose moiety to the biosurfactant via dTDP-L-rhamnose.

* * * * *

SEQUENCE LISTING

```
<160> NUMBER OF SEQ ID NOS: 24

<210> SEQ ID NO 1
<211> LENGTH: 12721
<212> TYPE: DNA
<213> ORGANISM: Variovorax paradoxus

<400> SEQUENCE: 1

gtcgtgtctc cttcttttcg tggggtgttc caacgggccg actgggaggt cggctgaaaa     60

ccgctcgcca gtgtgcgtgc cgcaaggttt gccttcaata aaataatcaa gctaagtaat    120

atgaatggca tgcatatcga ctcggtcgac ctcaatctgc tgcgcctgtt cgatgcggtc    180

taccgcgagc gcagcgtgag ccgcgccgcg gagtcgctgg gcctcacgca gcctgcggca    240

agccatgggc tgggacggct gcggctgctt ttgaaagacg cgctcttcac gcgtgccccc    300
```

-continued

```
ggcggcgtgg cgcccacgcc gcgcgccgac cggctcgcgg tggcggtgca ggcggcgctc    360
ggcacgatcg aagcggcgct gcacgagccc gatcgcttcg agccccaggt gtcgcgcaag    420
agctttcgta ttcacatgag cgacatcggc gaggggcgct tcctgcccgc gctgatggcg    480
cggctcggcg agctggcgcc cggcgtgcgg ctggagaccc tgccgctctt gcctgcggag    540
gttgcgcccg cactcgacag cggccgcatc gatttcgcct tcggctttct ctcgaccgtg    600
cgcgacacgc agcgcacgca tcttctgaaa gaccgctaca tcgtgctgct gcgcaagggc    660
catccctttg tgaagcgccg gcgcaagggg caggcgctgc tcgaggcgct gcaggagctc    720
gactacgtgg cggtgcgcac gcacgccgac acgctgcgca tcttgcagtt gctcaacctc    780
gaagaccgcc tgcgcctcac gaccgagcac ttcatggtgc taccggccat cgtgcgcgcc    840
accgatctcg cggtggtgat gccgcgcaac atcgcgcgag ggtttgcgga ggagggcggc    900
tacgcgatcg tcgagccgcc gtttccgctg cgcgatttca gcgtgtcgct gcactggagc    960
aagcgcttcg agggcgaccc ggccaaccgt tggttgcggc aggtgatcac ggcgctgttc   1020
tccgagcgcg gctgaagttc gaccaccaaa gtacgcgccg cgcggtgcaa gcgcgcgcga   1080
ctgcgcgagt aacacgccga gagattcccc tacagctttc tcgcccagtt gctgcatcgc   1140
aacattcttt tggggtgcat gacgcgcgaa atacgatgaa agccttcgat tccgaaagcc   1200
gcgattcagg tcgcaacttc gggatgaaat ctttcgcgct caaagacgtt cgtgaaatgt   1260
tttcttccct aaaaccgtca ctgaaagtgt tgaaaccact tgtacagtgg actggcaatg   1320
tgaacggatt gttaccgcgg agcaccggca tttctccttg agcggccgat gcacgacgcg   1380
tccatttcac gcgcacatgc atcgttgcca atttcactca agacctggag aagtgcatga   1440
gtaccgtcga tcagctgggc cgcaccgccc cccttacctc ggggcagatg gcgatgtggc   1500
tcggcgcaaa gttcgcgtcg cccgacacca atttcaatct cgccgaagcc atcgacatcg   1560
caggcgagat cgaccccgcg atcttcctgg cggccatgcg acaggtggcc gatgaagtcg   1620
aggccacgcg cctgagcttc atcgataccc cgcaagggcc acgacaggtc gtcgcgcccg   1680
ttttcaccgg cgagatcccc tacctcgacc tcagcggcga gagcgatccg caggccgagg   1740
ccgagcgctg gatgcatgcg gactacaccc gcagcatcga cctcgcgcac gggcagctgt   1800
ggctgtccgc gctgatccgc ctcgcgcccg atcgccacat ctggtaccac cgcagccatc   1860
acatcgcgct cgacggcttc agcggcggcc tcatcgcacg ccgcttcgcc gacatctaca   1920
ccgcgatggt cgacaacaac gcagcggtgc ccgaagactc gcgccttgca ccgatctcgc   1980
agctggccga cgaagaacat gcctatcgcg agtccggccg cttcccgcgc gaccgccagt   2040
actggaccga gcgcttcgcc gatgcacccg atccgttgag cctcgcctcg caccgctcgg   2100
tcaacgtcgg tggcctcttg cgccagacgg tgcacctgcc ggcggccagc gtgcaagccc   2160
tgcagaccat cgcgcaagag ctcggcacca cgctgccgca aatcctcatc gccaccaccg   2220
cggcctacct gtaccgcgca acgggcatcg aggacatggc aatcggcatc cccgtcaccg   2280
cgcgccacaa cgaccgcatg cgccgcgtgc ccgcgatggt ggccaacgcg ctgccgctgc   2340
gcctggcgat gcgcgcggac ctgccgattc cggaactgat ccgcgaagtc ggccggcaga   2400
tgcggcagat cctgcggcac cagtcgtatc gctacgagca tttgcgcagc gacctcaaca   2460
tgctggtgaa caaccggcag ctcttcacca ccgtggtcaa cgtcgagccc ttcgactacg   2520
acttccgctt tgcgggccat gccgcgaagc cgcgcaacct ctcgaacggc acggccgagg   2580
acctcggcat cttcctgtac gagcgcggca acgggcagga cctgcagatc gacttcgacg   2640
ccaaccccgc ggtgcacacc gcagaggaac tggccgatca ccagcgccgg ctgcttgcct   2700
```

-continued

```
tcatcgacgc cgtgatccgc ctgccgttgc aggccgtcgg ccagatcgac ctgctcggtg   2760
ccgaagagcg gcagcaattg ctggtcgagt ggaacgacac ggcccacgcc gtgcccgaca   2820
cccatctcac cgcgttgatc gaagcgcagc tcgcagccga tccgcaagcc atcgcattgc   2880
gcttcgacgg cgaggcgatg aacaacgaag aactgaaccg ccgcgccaac cgtctcgccc   2940
acctgctgcg cgcacgcggc gctggcccgg agcgcaccgt ggcgctcgcg atcccgcgtt   3000
cgatggacct gatgattgcc ttgctcgcca cgttgaagac cggcgcggcc tacctgccgg   3060
tcgatccgga tttcccggcg gaccgcatcg ccttcatgct cggcgatgcg cagcccgtgt   3120
gcctcgtcac gaccgaagcc ctcgcggagt cgctgccggc agccgccccc acattgctgc   3180
tcgatgtagc gcaaacgatt gcggatctgg agagttgcaa cgacaccaac ccgggcatcg   3240
cgatcgaccc ttcgcatccg gcctatgtga tctacacctc gggctcgacc ggcatgccca   3300
agggtgcggt cgtgtcgcac cgcgccatcg tcaaccgcct gcgctggatg caggaccgct   3360
acggccttca ggccgacgac cgcgtgctgc agaagacgcc ttccagcttc gacgtgtcgg   3420
tgtgggagtt cttctggccg ctgatcgacg gtgccacgct ggtgcttgcg aaaccgggcg   3480
gccacaagga tgcggcctac ctcgcggggc tgatcgcgga ggagggcatc accacgatcc   3540
acttcgtgcc gtcgatgctc gaggtcttcc tgctcgagcc cacggcgggc gcatgcacca   3600
cgctgcgccg cgtgatctgc agcggcgaag ccttgtcgcc cgcgctgcaa tcgcagttcc   3660
agcagcacct ctcgtgcgag ctgcacaacc tctacggtcc gaccgaggcc gcggtcgacg   3720
tcacctcgtg ggagtgcgaa cgcacggacg acgcagaagc ctcgagcgtt cccatcggcc   3780
gcccgatctg gaacacccag atgcacgtgc tcgacagcgg cctgcagccc gtgccggccg   3840
gcgtgactgg cgagctgtac atcgcgggcg tcggcctcgc acgcggctac ctcaagcgcc   3900
cgttgctgag cgccgagcgt ttcatcgcca accccctacgg cacacccggc agccgcatgt  3960
accgcaccgg cgacctcgcg cgctggcgca aggacggcag ccttgacttc ctcggccgcg   4020
ccgaccagca ggtgaagatc cggggcctgc gcatcgagcc gggagagatc gaatccgtgc   4080
tgctgcagca tccgcaagtc gcgcaggccg ccgtggtggc gcgcgaagac gtaccgggcg   4140
aaaagcgtct cgtggcctac gtcgttgcga cggacgctgc cgatccgcaa gcggccgaac   4200
tgcgcacgcg cctcgcgcaa tcgctgcccg agtacatggt gccttcggcc ttcgtcagcc   4260
tcccgtcgct gccgctcgga cccagcggca agctcgaccg caaggcgctg ccgcccccg    4320
aagtgcaggc cgccacgccg tacgccgcgc cgcgcacgcc gaccgaaaag atcctggccg   4380
gcctctgggc cgagacgctg catttgccgc gcgtcggtgt caacgacaac ttcttcgaac   4440
tcggcggcca ctcgctgatg atcgtgcagc tcatgtcgat gatccggcag caattcatga   4500
tcgacctgcc ggtcgacacg ctgttccagg tctccaccat cgcgggcctt gccgagctgc   4560
tcgaccagga atcggtcgcc cgtccgagcc tgactccgat gccgcgcccc gcgcgcattc   4620
cgctgtcctt cgcgcagcgc cgcctgtggc tgatgaacca gctcgaaggc gcgaacccgg   4680
cctacaacat gccgctcgcg ctgcgcctgt cgggtgtgct cgatcgcacc gcattgcatg   4740
cggcgctcgg cgacctggtg cagcgccacg agagcctgcg cacggtctac ccgaacgaag   4800
acgggctgcc gtaccagcac atcctcgacg gcgcggatgc gcgtccggcg gtgatcgagg   4860
ccgacagcag cgaagaagaa atcgcggcgc agcttcacgc cgctgcgggc catgccttcg   4920
atctcggcag cgcggcgccc ttgcgcgtct acctgttcaa gctcgccggc gacgaacacg   4980
tgctgctgct gctcacgcac cacattgccg gcgatggcgc ctcgctgctg ccgctagcgc   5040
```

-continued

```
gcgacatcag cgtggcctat gccgcgcgct gcgaaggcaa ggcgccgggc tgggagccgc   5100
tgccgctgca atacgccgac tacgcgctgt ggcagcagga gctgctcggc agcgaagacg   5160
atgccgagag catggccggc cgccagcgtg agttctggcg ttcctcgctg agcgacctgc   5220
ccgagcaact ggcgctgccc gtcgaccacg cacggccgct cgtgccgacc taccgcggcg   5280
atgtggtccc gctgcagatt ccgtcgcatg tgcatgaacg catcctgcaa ctggcgcgcg   5340
acgggcaggc cagcgtcttc atggtgctgc aggccgcact cgcgggcctc ctgagccgcc   5400
tcggcgcggg cgacgacatc gtcatcggca gcccggtcgc ggggcgcagc gaccatgcgc   5460
tggacgaact catcggctgc ttcgtcaaca cgctggtgct gcgcactgac acctcgggcc   5520
agccgagcct gcgcgagctg gtctcgcgcg tgcgcgccac caacctcgcg gcctatgcga   5580
accaggagtt tccgtacgac cgcctcgtgg agctgctgcg tccgggccgc tcgcgcgcca   5640
acctgccgct gttccaggtc atgctgggct tccagggcac gagccgcctg tcgttcagcc   5700
tgccgggcct gtcgatcgcg ccgcagccgg tggccatcga caccgcgaag ttcgacctgt   5760
cgttcatcct cggcgagcaa cgcggtgccg atggcctgcc gggcggcatc tccggcggca   5820
tccagtacag caccgacctg ttcgagcgca gcacggtcga ggccatgggc gcgcggctgg   5880
tgcgtttgct ggaagaggcc tgcgaggcgc ccgacgatgc ggtgagtggc ctcgccatcc   5940
tgagcgcgga agaaaccgac cgcctgctgt ccgactggag cggccgcacg cgcgaccttg   6000
cgccgctctc gttcgccgac atggtggcct cgcatgccgc ggagcgcccg cttgcagatg   6060
cagtggtgct cgacgacgcg accgtcagct acgccgaact cgatgcacgc gccaaccggc   6120
tctcgcacct gctgcgtgcg caaggcatcg ggttggcgc catcgtcgcg acagtgctgc    6180
cgcgttcgct cgacctcatc gtggcgcact tggccatcgt gaaggccggc gcggcctacc   6240
tgcccatcga ccccaaccac atggccgcgc gcagcgcctt cgtgttcgag gaggccgcgc   6300
ccgccgcggt gctgacgcac gatgcgctgt tgcccgagct ggtcggcgtt ccccgctgca   6360
tcgcgctcga cagcgacagc atggttgccg cgctggccat ccagtcggat acgccgctgg   6420
tgcatgcggc caatccacag gatgccgcct acctcatcta cacctccggc tccaccggca   6480
tgcccaaggg cgtggtggtg ccgcatgcgg gcctgggcag cctcggcacc gcgatggcgg   6540
agcggctcgt catcggccac ggctcgcgcg tgctgcagtt ctcctccagc ggcttcgacg   6600
cgtcggtgat ggaccagctg atggcctttg gcgccggtgc cgcgctggtg gtgccggggc   6660
cggagcaact gctcggcacg gagctggccg atctgctcga gaagcaggcc gtgagccacg   6720
cgctgattcc gcccgccgcg ctcgcgaccc tgccgcacgg cgagttcccg cacctgcaga   6780
cgctggtggt cggcggcgat gcctgcaccg ccgcgctggc ggcgaagtgg tcgcaaggcc   6840
gccgcatgat caacgcctac ggcccgaccg agatcaccat ctgcgcgagc atgagcgcgc   6900
cgatgacggc cgaggagttg ccctccatcg gccagccgat ctggaacacg cggatgtatg   6960
tgctcgacag cgccctgcaa ccggtgccgc cgggtgtcgc gggcgagctc tacatcgccg   7020
gcagcggcgt ggcgcgcggc tatctcaacc ggccggcatt gagtgcggaa cgcttcatcg   7080
ccgacccgca tggcgcgccc ggcagccgca tgtaccgcag cggcgacctc gcacgctggc   7140
gcgccgacgg cacgctcgac ttcctcggcc gcgccgacca gcaggtgaag atccggggct   7200
tccgcatcga gccgggcgag atcgaatccg tgctgctcaa gcacccgttg atcacgcagg   7260
ccgccgtgat cgcccgcgag gacgtgcccg gcgagaagcg cctggtcgcc tacttcgtcg   7320
ccggttccga gccgcagccc accgagctgc gcgcccacat ggcgcaggcc ttgcccgact   7380
acatggtgcc ttcggccttc gtgcgcctgc cgtcgctgcc gctcacgcaa agcggcaagc   7440
```

-continued tcgacaagaa ggcgctgccg gtgcccgacc agcagcccgc cgcgctgtac gtggagcccc 7500
gcacgccgac cgagaaactg ctcgcgggcc tctggtccga gacgctgcac ctggagcgtg 7560
tcggcatcca cgacaacttc ttcgagatcg gcgggcattc gctcatggcg atccagctgg 7620
gcatgcgcat ccgccagcag gtgcgcgcgg acttcccgca cgccgaggtc tacaaccgcc 7680
cgacgattgc cgacctggcc gcctggctcg acaacgaagg cggcacggtc gaggcgctgg 7740
acctgtcgcg cgagctcgac ctgcccgcgc acatccgccc gcaggccact gcaccgaagc 7800
tcgcaccgcg ccgcgtgttc ctcaccggcg cgagcggctt cgtcggcagt cacctgctgg 7860
ccgcgctgtt gcgcgacacc gcggcctgcg tggtctgcca cgtgcgcgcg cccgacgagc 7920
aggccggcga gcagcgcctc aagcgcacgc tggcccagcg ccagctcggt gcgatctggg 7980
acaacgcgcg catcaaggtc gtgaccggcg acctcggcaa gccgcgcctg ggcctcgatg 8040
acgctgccgt gcaactggtg cgcgacggct gcgacgccat ctaccactgc gccgcgcagg 8100
tcgacttcct gcatccctac gcgagcctca agcccgcgaa cgtcgacagc gtggtcacgc 8160
tgctcgaatg gacggcgcag gggcgcgcga agagcatgca ctacgtctcc acgctggctg 8220
tgatcgacca gaacaacaag gaagacacca tcaccgagca atcggcgctg gcctcatgga 8280
gcgggctggt cgacggctac agccagagca agtgggtcgg cgatgcgctg gcccgcgagg 8340
cgcaggcgcg cggcatgccg gtggcgatct accggctggg ggcagtcacc ggcgaccaca 8400
cgcacgcgat ctgcaatgcc gacgacctga tctggcgcgt ggcgcatctc tatgccgacc 8460
tggaagcgat tcccgatatg gacctgccgc tcaacctcac accggtggac gacgtggcgc 8520
gcgccatcct cggccttgcg gcgcaggagg cctcgtgggg ccaggtgttc cacctgatga 8580
gccaggcggc gctgcgggtg cgcgacattc cgcacgtctt cgagcgcatg ggcatgcggc 8640
tggagccggt cgggctggag ccctggctgc agcgcgcgca tgcacggctg gccgtcgcgc 8700
atgaccgcga cctggccgcg gtgctcgcca tcctcgaccg ctacgacacc acggccacgc 8760
cgccgcaggt gagcggcgcg gccacgcatg cgcagctcga ggccatcggc gcgccgatcc 8820
gcccggtgga ccgcgacctg ctgcagcgct acttcgtcga cctgggcatc gacaccaagg 8880
cgcgccgcgc cctggaaacc accacttcat aggagcacac ggaatggcac gctatctcat 8940
cgcagcaacc gccttgccgg gacacgtcct gccgatgctg gccatcgcgc agcatctggt 9000
gaaccagggg cacgaggtgc gggtgcacac cgcgagccag ttcagggcgc aggccgaggc 9060
gaccggtgcg ggcttcacgc ccttcgagcg cacgatcgac ttcgactacc gcgacctgga 9120
caagcgcttt cccgagcgcc agcgcatcgc ctcggcgcat gcgcagctgt gcttcggcct 9180
gaagcacttc tttgccgatg cgatggccgc gcagcatgcg ggcctgcaat cgatcctcga 9240
agacttcgag gccgatgcca tcgtggtcga cacgatgttc tgcggcactt tcccgctgct 9300
gctaggcaag gagcgcgaag accgcccggc catcgtcggc atcggcatct cggcgctgcc 9360
gctctcgagc tgcgacaccg ccttcttcgg caccgcgctg ccgccgtcgt ccacgccgga 9420
agggcgggtg cgcaacaagg cgatgaacgc caacctcaaa caggcgatgt tcggcgaggt 9480
gcaacgctac ttcgacacgc tgctcgcgcg ttcgggcctg gccgcgctgc ccgatttctt 9540
cgtcgatgcg atggtgaagc tgcccgatct ttacctgcag ctcaccgcgc cttcgttcga 9600
atacccgcgc agcgacctgc ccgcgtcggt gcatttcgtc ggcccgctgc tctcgcccgc 9660
gagccgcgac ttcacgccgc ccgagtggtg gcacgagctg gacgacggcc gctcggtcgt 9720
gctggtcacg cagggcacgc tggccaacca gaatccgtcg cagctgatcg gcccgacgct 9780
gcaggcgctg gccggcgaca agaacatcct cgtcatcgcc accaccggcg gcccggtgcc 9840
gcccgccctg acggtgaacc tgcccgccaa cgcccgcgtg gtgccgttcc tgccctacga 9900
ccggctgctg cccaagctgc acgcgatggt caccaacggc ggctacggct cggtcaacca 9960
tgcattgagc ctcggtgtgc cgctggtggt ggccggcacc tccgaagaga agcccgagat 10020
cgccgcgcgc gtggcctggt cgggcgcggg catcaacctc gccaccggcc agccgaccgc 10080
gcgccaggtc ggcgacgcgg tgcgcaaggt actgggcaac tcgacctatc gccagcgtgc 10140
ggcggtgctg cgtgaggact tcgcttgcca tcgcgcgctg accggcatcg ccggcgccct 10200
cgaggcactt ctgcaaacct tcgcatccgc ggaaatggct tgaacctgaa ccccatacga 10260
caaaggaaat cccagatgag caacccgttc gacgacaaga acgccagctt ccaggtgctg 10320
gtgaacgacg agggccagca ctcgctgtgg cccgccttca tcgccgtgcc cgccggctgg 10380
caggtggcgc tggcgccgac cgaccgcgac gcctgcagcg cctacatcgc ggcgaactgg 10440
caggacatgc gcccgcgttc gctggtggtg gccacggcgg ccggctgacg ccgaggatgt 10500
ccttcccgtt cggtgccgtc gtcgtcacct atttcccgac cggcgagcaa gtggcgaacc 10560
tccattcgct ggcggcctcg tgtccgcacc tctgcgtggt cgacaacacg ccgcaggtgg 10620
gcgattggca tgcggcgctc gtcgatgcgg gcgtttcggt gctgcacaac ggcaaccgcg 10680
gcggcatcgc gggcgccttc aaccgcggca tcatcgacct cgaagcgcgg ggcgccgaac 10740
tcttcttcct gctcgaccag gattcgaagc tgccacccgg ctacttcgat gccatgtgcg 10800
aggctgcgat ggtggcccgg gagcggaagg gcgagggcaa tggtgaggaa gacgcggcct 10860
tcctgatcgg cccgctcgtc cacgacacga acctggacgc gctgatcccg caattcggcc 10920
tccagggcaa acgcgtctac cagttcgacc tgcggcagcc cttcaccgag ccgctgatgc 10980
gctgcgcctt catgatttcc tcgggctccc tgatttcgcg cggcgcctgg gcccggatcg 11040
gccggttcga cgagcgctat gtgatcgacc acgtggacac cgactactgc atgcgtgccc 11100
tgggtcgcgg cgtgccgctc tacctgaatc cgcacgtcgt gctgcggcac cagattggcg 11160
acatccgtgc ccggtcgctg ttcggctgga agatccactt catcaactac ccggccgcgc 11220
ggcgctacta catcgcgcgc aatgccatcg atctctcgcg ggcgcatgtg cgcgcctttc 11280
ccgcgatcct gttcatcaac gtttacacgc tcaagcagat cctgccgatg ctgatgttcg 11340
agcgcgaccg cttcaagaag accatcgcgc tgatgctcgg ctgcttcgat ggcctgttcg 11400
ggcggctcgg gggcctcggc gaggtgcatc cgcggatggg caaatacctg ggccgcagcg 11460
attgaccgcc acccttccag cgccgcgcgt acgccgcgcc gcgctcgcct tcatcttcgt 11520
cacggtgctg atcgacttca tggcgttcgg cctgatcctg cccggcctgc cgcacctggt 11580
ggagcggctg gccggcggca gcacggtaac ggcggcgtac tggatcgctg tgttcggcac 11640
cgcgttcgcg gcgatccagt tcgtgagctc gccgatccag ggcgcgctgt ccgaccgctt 11700
cgggcggcgg ccggtgatcc tgctgtcgtg cttcggcctc ggcgtggatt tcgtgttcat 11760
ggccctggcc gacagcctgc cgtggctgtt cgtcggccgg gtggtctccg gcgtgttctc 11820
ggccagcttc accatcgcca atgcctacat cgccgatgtg acgctgccgg aggagcgcgc 11880
ccgcagctac ggcatcgtgg gggccgcgtt cggcatgggc ctggtgttcg ggccggtgct 11940
cggcgggcaa ctgagccaca tcgatccgcg cctgccgttc tggttcgcgg ccggcttgac 12000
gctgctcagc ttctgctacg gatggttcgt gttgcccgaa tcgctgccgc ccgagcggcg 12060
tgcccgcaag ttcgactggt cgcatgccaa tccggttggg acgctggtgc tgctcaagcg 12120
ctatccgcag gtgttcggac tggcggcggt gatcttcctc gtgaacctgg ctcagtacgt 12180

-continued ctatcccagc gtgttcgtgc tgttcgccga ctaccggtat cactggaagg aagacgccgt 12240
gggctgggtg ctcggcgcgg tgggcgtgct cagcgtgctg gtcaatgcgc tgttgatcgg 12300
gccgggcgtg aagcgcttcg gcgagcgccg cgccctgttg ctcggcatgg gcttcggcgt 12360
gctcggcttc gtcatcatcg ggtttgccga cgctggatgg atcctcctgg ccggggtgcc 12420
gttcggcatt ctgctggcgt tcgccggacc ggcggcgcag gcgctggtca cgctgcaggt 12480
cggcaccgcc gagcagggcc gcatccaggg ggcgctcacc agcctggtgt cggtggcggg 12540
catcgtcggg ccggcgatgt tcgccggcag cttcggttac ttcatcggcg cggacgcgcc 12600
ggtgcacttg ccgggcgcgc cgtttttcct cgctgcggcg ttcctctgca tcggcacgct 12660
gatcgcgtgg cgctacgcac agccgaagcc cgcgacggca gcggtgcccg agccgacctg 12720
a 12721

<210> SEQ ID NO 2
<211> LENGTH: 3959
<212> TYPE: DNA
<213> ORGANISM: Variovorax paradoxus

<400> SEQUENCE: 2
ccgctgcgcc tcgcaacggg tttgctcctt cggtgcatcg cgatccctgc gggtgcgatg 60
gctctccaga cggcgtttga tgtgatgcag tactgacccc ctgttcgggc cgacctgagc 120
gtttatggga gtttgcgcct tcggtagggc caccggggtg gcccgctctc ctgcagtggg 180
gcgattgtag gtgggcactg ccaatgcgcc aaccccggga gtttcggccc ttgggccgat 240
gggataatca tccgttcatt cgccggaggg cgatcgttcg acaacaacag gggaccccat 300
gatcctggta accggcggcg caggcttcat tggcgccaat ttcgtactcg actggctcgc 360
acagagcgat gaaccggtcg tgaacctaga caagctgacc tacgcgggca acctcgagac 420
gctcgcatcg ctcaaggaca acccgaagca catcttcgtg cagggcgaca tcggcgacag 480
cgcgctgctc gaccgcctgc tggccgagca caagccgcgt gccgtggtca acttcgcggc 540
cgaatcgcac gtcgaccgct cgatccacgg ccccgaagac ttcgtgcaga ccaacgtgct 600
gggcaccttc cgcctgctcg aatccgtgcg cggtttctgg aatgccctgc cggccgacca 660
gaaggccgcc ttccgcttcc tgcatgtgtc gaccgacgag gtctacggct cgctctccaa 720
gaccgacccg gccttcaccg aagagaacaa gtacgagccc aacagcccgt actcggccag 780
caaggccgcc agcgaccacc tcgtgcgcgc ctggcaccac acctacggcc tgccggtggt 840
caccaccaac tgctcgaaca actacgggcc gttccacttc cccgagaagc tcattcccct 900
gatgatcgtc aacgcgctgg cgggcaagcc gctgcccgtg tacggcgacg gcatgcaggt 960
gcgcgactgg ctctacgtga aggaccactg cagcgccatc cgccgcgtgc tcgaagccgg 1020
caagctcggc gagacctaca acgtgggcgg ctggaacgag aagcccaaca tcgagatcgt 1080
caacaccgtc tgcgcgctgc tcgacgagct gagccccaag gccggcggca agccgtacaa 1140
ggaacagatc acctatgtga ccgaccgccc cggccacgac cgccgctacg cgatcgacgc 1200
acgcaagctc gagcgcgaac tcggctggaa acctgccgag accttcgaca gcggcatccg 1260
caagacggtc gagtggtacc tcgcgaacgg cgagtgggtg cgcaacgtgc aaagcggcgc 1320
gtaccgcgag tgggtcgaga agcaatacga cgccgcaccg gcgaaggcca ccgcatgaag 1380
ctgctgctgc tgggcaaggg cggacaggtc ggctgggagc tgcaacgcag cctcgcgccc 1440
ctgggcgaac tggtggcgct cgatttcgac agcaccgact tcaacgccga cttcagtcgc 1500

-continued

```
cccgagcagc tggccgagac agtgctgaag gtgcgccccg acgtcatcgt caatgccgca   1560

gcgcacaccg cggtcgacaa ggccgagagc gagcccgagt tcgcgcgcaa gctcaacgcc   1620

acctcgcccg gcgtggtggc cgaagccgcg cagcagatcg gcgcgctgat ggttcactac   1680

tcgaccgact acgtcttcga cggcagcggc agcaagccgt ggaaagaaga cgatgcgacc   1740

ggcccgctca gcgtctacgg cagcaccaag ctcgaaggcg agcaactggt ggcaaagcac   1800

tgtgcgaagc acctgatctt tcgcaccagc tgggtctatg ccgcgcgcgg cggcaacttc   1860

gccaagacca tgctgcgcat cgccaaggag cgcgacaagc tgaccgtcat cgacgaccag   1920

ttcggcgcgc ccaccggcgc ggaactgctg gccgacatca ccgcgcacgc gattcgcgcg   1980

acgctgcagg acccgtccaa ggccgggctc tatcacgcgg tggccggtgg cgtgaccacg   2040

tggcacggct atgcgcgctt cgtgatcgag caggccaagg cggcgggcgt ggaactgaag   2100

gccggccccg aagcggtcga gcccgtgccc accacggcat tcccgacgcc ggccaggcgg   2160

ccgcacaact cgcgcctgga caccaccaag ctgcaatcga ccttcggcct cgtgctgccc   2220

gagtggcagt ccggcgtcgc ccgcatgttg cgcgaaacct tctgatattc gcagagcaag   2280

agagacacga acaccccatg accaagacga cgcaacgcaa aggcatcatc ctcgccggtg   2340

gctcgggcac ccgcctgcac cccgcgacgc ttgccatgag caaacaactg ctgccggtgt   2400

acgacaagcc gatgatctat tacccgctga gcacgctgat gctgggcggc atgcgcgaca   2460

tcctgatcat cagcacgccg caggacacgc cgcgtttcca gcaactgctg ggggatggca   2520

gccaatgggg catcaacctg cagtacgcgg tgcagccgag cccggatggt ctggcgcagg   2580

cgttcatcat cggtgacaag ttcgtgggca acgacccgag tgcgctggtg ctgggggaca   2640

acatcttcta tggccacgac ttcgcccatc tgctggccga tgccgacgcc aagacctcgg   2700

gtgcgacggt gttcgcctac cacgtgcacg accccgagcg ctacggcgtg gtggccttcg   2760

atgccaaggg cagggcgagc agcatcgaag aaaagccgct caagcccaag agcagctatg   2820

cggtcacggg cctctacttc tacgacaacc aggtcgtcga catcgccaag gccgtgaagc   2880

cgagcgcgcg cggcgaactc gagatcaccg cggtcaacca ggcgtatctc gacctcgacc   2940

agctgaacgt gcagatcatg cagcgcggct atgcgtggct cgataccggt acgcacgaca   3000

gcctgctgga agccgggcag ttcattgcca cgctcgagca ccgccagggg ctgaagatcg   3060

catgccccga agagatcgca tggcgcaatg gcttcatctc aaccgagcaa ctcgaaaagc   3120

tcgcggcgcc gctggaaaag agcggctacg gcaagtacct caagcacctg ctgaacgacg   3180

aggtgcgctc gtgaaggcca cgcccacctc gattcctgac gtgctcgtga tcgagccgaa   3240

ggtgtttggc gatgcacggg gcttcttctt cgaaagcttc aaccagaagg ccttcgacga   3300

agcgatcggc aagcatgtcg acttcgtgca ggacaaccat tcgcgatcgg ccaagggtgt   3360

gctgcggggg ctgcattacc aggtccagca gccgcaaggc aagctcgtgc gggtggtgcg   3420

tggtgcggtg ttcgacgtgg ccgtcgacat ccgcaagtcg tcgccgactt ttggcaaatg   3480

ggtgggtgtc gagttgaacg aagacaacca caagcagctc tgggtgccgg caggattcgc   3540

gcacggtttc ctggtgttga gcgagaccgc ggaattcctc tacaagacca ccgactacta   3600

cgcgcccgcc cacgagcgcg cgattgtctg gaacgacccc gctgtcggta ttcgatggcc   3660

ggatgtggga ggggcaccgg tcctgtcgaa gaaggacgaa gacgggtgtc ttctgcaagc   3720

ggcagaggtt ttctagtgtc ctttcgtcag atagcggggc ggcttcgcgt atcgggatcc   3780

cgcgttgagc ccgcaagagt gccctgagag ggggggcgaa aaactcacaa cgccactgcc   3840

tcgagcaaac gtgcgtctcg cagctttctg aagttgttgc accttctttt tttttctctt   3900
```

-continued acatctttga aatgattttg aaaatccgcg gcgatcgcat gcatgctgct ggaatcacc 3959

<210> SEQ ID NO 3
<211> LENGTH: 915
<212> TYPE: DNA
<213> ORGANISM: Variovorax paradoxus

<400> SEQUENCE: 3
atgaatggca tgcatatcga ctcggtcgac ctcaatctgc tgcgcctgtt cgatgcggtc 60
taccgcgagc gcagcgtgag ccgcgccgcg gagtcgctgg gcctcacgca gcctgcggca 120
agccatgggc tgggacggct gcggctgctt ttgaaagacg cgctcttcac gcgtgccccc 180
ggcggcgtgg cgcccacgcc gcgcgccgac cggctcgcgg tggcggtgca ggcggcgctc 240
ggcacgatcg aagcggcgct gcacgagccc gatcgcttcg agccccaggt gtcgcgcaag 300
agctttcgta ttcacatgag cgacatcggc gaggggcgct tcctgcccgc gctgatggcg 360
cggctcggcg agctggcgcc cggcgtgcgg ctggagaccc tgccgctctt gcctgcggag 420
gttgcgcccg cactcgacag cggccgcatc gatttcgcct tcggctttct ctcgaccgtg 480
cgcgacacgc agcgcacgca tcttctgaaa gaccgctaca tcgtgctgct gcgcaagggc 540
catccctttg tgaagcgccg gcgcaagggg caggcgctgc tcgaggcgct gcaggagctc 600
gactacgtgg cggtgcgcac gcacgccgac acgctgcgca tcttgcagtt gctcaacctc 660
gaagaccgcc tgcgcctcac gaccgagcac ttcatggtgc taccggccat cgtgcgcgcc 720
accgatctcg cggtggtgat gccgcgcaac atcgcgcgag ggtttgcgga ggagggcggc 780
tacgcgatcg tcgagccgcc gtttccgctg cgcgatttca gcgtgtcgct gcactggagc 840
aagcgcttcg agggcgaccc ggccaaccgt tggttgcggc aggtgatcac ggcgctgttc 900
tccgagcgcg gctga 915

<210> SEQ ID NO 4
<211> LENGTH: 304
<212> TYPE: PRT
<213> ORGANISM: Variovorax paradoxus

<400> SEQUENCE: 4

```
Met Asn Gly Met His Ile Asp Ser Val Asp Leu Asn Leu Leu Arg Leu
1               5                   10                  15

Phe Asp Ala Val Tyr Arg Glu Arg Ser Val Ser Arg Ala Ala Glu Ser
            20                  25                  30

Leu Gly Leu Thr Gln Pro Ala Ala Ser His Gly Leu Gly Arg Leu Arg
        35                  40                  45

Leu Leu Leu Lys Asp Ala Leu Phe Thr Arg Ala Pro Gly Gly Val Ala
    50                  55                  60

Pro Thr Pro Arg Ala Asp Arg Leu Ala Val Ala Val Gln Ala Ala Leu
65                  70                  75                  80

Gly Thr Ile Glu Ala Ala Leu His Glu Pro Asp Arg Phe Glu Pro Gln
                85                  90                  95

Val Ser Arg Lys Ser Phe Arg Ile His Met Ser Asp Ile Gly Glu Gly
            100                 105                 110

Arg Phe Leu Pro Ala Leu Met Ala Arg Leu Gly Glu Leu Ala Pro Gly
        115                 120                 125

Val Arg Leu Glu Thr Leu Pro Leu Leu Pro Ala Glu Val Ala Pro Ala
    130                 135                 140

Leu Asp Ser Gly Arg Ile Asp Phe Ala Phe Gly Phe Leu Ser Thr Val
```

-continued

```
145                 150                 155                 160

Arg Asp Thr Gln Arg Thr His Leu Leu Lys Asp Arg Tyr Ile Val Leu
                165                 170                 175

Leu Arg Lys Gly His Pro Phe Val Lys Arg Arg Arg Lys Gly Gln Ala
            180                 185                 190

Leu Leu Glu Ala Leu Gln Glu Leu Asp Tyr Val Ala Val Arg Thr His
        195                 200                 205

Ala Asp Thr Leu Arg Ile Leu Gln Leu Leu Asn Leu Glu Asp Arg Leu
    210                 215                 220

Arg Leu Thr Thr Glu His Phe Met Val Leu Pro Ala Ile Val Arg Ala
225                 230                 235                 240

Thr Asp Leu Ala Val Val Met Pro Arg Asn Ile Ala Arg Gly Phe Ala
                245                 250                 255

Glu Glu Gly Gly Tyr Ala Ile Val Glu Pro Pro Phe Pro Leu Arg Asp
            260                 265                 270

Phe Ser Val Ser Leu His Trp Ser Lys Arg Phe Glu Gly Asp Pro Ala
        275                 280                 285

Asn Arg Trp Leu Arg Gln Val Ile Thr Ala Leu Phe Ser Glu Arg Gly
    290                 295                 300


<210> SEQ ID NO 5
<211> LENGTH: 7476
<212> TYPE: DNA
<213> ORGANISM: Variovorax paradoxus

<400> SEQUENCE: 5

atgagtaccg tcgatcagct gggccgcacc gcccccctta cctcggggca gatggcgatg     60

tggctcggcg caaagttcgc gtcgcccgac accaatttca atctcgccga agccatcgac    120

atcgcaggcg agatcgaccc cgcgatcttc ctggcggcca tgcgacaggt ggccgatgaa    180

gtcgaggcca cgcgcctgag cttcatcgat accccgcaag ggccacgaca ggtcgtcgcg    240

cccgttttca ccggcgagat cccctacctc gacctcagcg gcgagagcga tccgcaggcc    300

gaggccgagc gctggatgca tgcggactac acccgcagca tcgacctcgc gcacgggcag    360

ctgtggctgt ccgcgctgat ccgcctcgcg cccgatcgcc acatctggta ccaccgcagc    420

catcacatcg cgctcgacgg cttcagcggc ggcctcatcg cacgccgctt cgccgacatc    480

tacaccgcga tggtcgacaa caacgcagcg gtgcccgaag actcgcgcct tgcaccgatc    540

tcgcagctgg ccgacgaaga acatgcctat cgcgagtccg gccgcttccc gcgcgaccgc    600

cagtactgga ccgagcgctt cgccgatgca cccgatccgt tgagcctcgc ctcgcaccgc    660

tcggtcaacg tcggtggcct cttgcgccag acggtgcacc tgccggcggc cagcgtgcaa    720

gccctgcaga ccatcgcgca agagctcggc accacgctgc cgcaaatcct catcgccacc    780

accgcggcct acctgtaccg cgcaacgggc atcgaggaca tggcaatcgg catccccgtc    840

accgcgcgcc acaacgaccg catgcgccgc gtgcccgcga tggtggccaa cgcgctgccg    900

ctgcgcctgg cgatgcgcgc ggacctgccg attccggaac tgatccgcga agtcggccgg    960

cagatgcggc agatcctgcg gcaccagtcg tatcgctacg agcatttgcg cagcgacctc   1020

aacatgctgg tgaacaaccg gcagctcttc accaccgtgg tcaacgtcga gcccttcgac   1080

tacgacttcc gctttgcggg ccatgccgcg aagccgcgca acctctcgaa cggcacggcc   1140

gaggacctcg gcatcttcct gtacgagcgc ggcaacgggc aggacctgca gatcgacttc   1200

gacgccaacc ccgcggtgca caccgcagag gaactggccg atcaccagcg ccggctgctt   1260
```

-continued

```
gccttcatcg acgccgtgat ccgcctgccg ttgcaggccg tcggccagat cgacctgctc   1320
ggtgccgaag agcggcagca attgctggtc gagtggaacg acacggccca cgccgtgccc   1380
gacacccatc tcaccgcgtt gatcgaagcg cagctcgcag ccgatccgca agccatcgca   1440
ttgcgcttcg acggcgaggc gatgaacaac gaagaactga accgccgcgc caaccgtctc   1500
gcccacctgc tgcgcgcacg cggcgctggc ccggagcgca ccgtggcgct cgcgatcccg   1560
cgttcgatgg acctgatgat tgccttgctc gccacgttga agaccggcgc ggcctacctg   1620
ccggtcgatc cggatttccc ggcggaccgc atcgccttca tgctcggcga tgcgcagccc   1680
gtgtgcctcg tcacgaccga agccctcgcg gagtcgctgc cggcagccgc ccccacattg   1740
ctgctcgatg tagcgcaaac gattgcggat ctggagagtt gcaacgacac caacccgggc   1800
atcgcgatcg acccttcgca tccggcctat gtgatctaca cctcgggctc gaccggcatg   1860
cccaagggtg cggtcgtgtc gcaccgcgcc atcgtcaacc gcctgcgctg gatgcaggac   1920
cgctacggcc ttcaggccga cgaccgcgtg ctgcagaaga cgccttccag cttcgacgtg   1980
tcggtgtggg agttcttctg gccgctgatc gacggtgcca cgctggtgct tgcgaaaccg   2040
ggcggccaca aggatgcggc ctacctcgcg gggctgatcg cggaggaggg catcaccacg   2100
atccacttcg tgccgtcgat gctcgaggtc ttcctgctcg agcccacggc gggcgcatgc   2160
accacgctgc gccgcgtgat ctgcagcggc gaagccttgt cgcccgcgct gcaatcgcag   2220
ttccagcagc acctctcgtg cgagctgcac aacctctacg gtccgaccga ggccgcggtc   2280
gacgtcacct cgtgggagtg cgaacgcacg gacgacgcag aagcctcgag cgttcccatc   2340
ggccgcccga tctggaacac ccagatgcac gtgctcgaca gcggcctgca gcccgtgccg   2400
gccggcgtga ctggcgagct gtacatcgcg ggcgtcggcc tcgcacgcgg ctacctcaag   2460
cgcccgttgc tgagcgccga gcgtttcatc gccaacccct acggcacacc cggcagccgc   2520
atgtaccgca ccggcgacct cgcgcgctgg cgcaaggacg gcagccttga cttcctcggc   2580
cgcgccgacc agcaggtgaa gatccggggc ctgcgcatcg agccgggaga gatcgaatcc   2640
gtgctgctgc agcatccgca agtcgcgcag gccgccgtgg tggcgcgcga agacgtaccg   2700
ggcgaaaagc gtctcgtggc ctacgtcgtt gcgacggacg ctgccgatcc gcaagcggcc   2760
gaactgcgca cgcgcctcgc gcaatcgctg cccgagtaca tggtgccttc ggccttcgtc   2820
agcctcccgt cgctgccgct cggacccagc ggcaagctcg accgcaaggc gctgccgccc   2880
cccgaagtgc aggccgccac gccgtacgcc gcgccgcgca cgccgaccga aaagatcctg   2940
gccggcctct gggccgagac gctgcatttg ccgcgcgtcg gtgtcaacga caacttcttc   3000
gaactcggcg gccactcgct gatgatcgtg cagctcatgt cgatgatccg gcagcaattc   3060
atgatcgacc tgccggtcga cacgctgttc caggtctcca ccatcgcggg ccttgccgag   3120
ctgctcgacc aggaatcggt cgcccgtccg agcctgactc cgatgccgcg ccccgcgcgc   3180
attccgctgt ccttcgcgca gcgccgcctg tggctgatga accagctcga aggcgcgaac   3240
ccggcctaca acatgccgct cgcgctgcgc ctgtcgggtg tgctcgatcg caccgcattg   3300
catgcggcgc tcggcgacct ggtgcagcgc cacgagagcc tgcgcacggt ctacccgaac   3360
gaagacgggc tgccgtacca gcacatcctc gacggcgcgg atgcgcgtcc ggcggtgatc   3420
gaggccgaca gcagcgaaga agaaatcgcg gcgcagcttc acgccgctgc gggccatgcc   3480
ttcgatctcg gcagcgcggc gcccttgcgc gtctacctgt tcaagctcgc cggcgacgaa   3540
cacgtgctgc tgctgctcac gcaccacatt gccggcgatg gcgcctcgct gctgccgcta   3600
gcgcgcgaca tcagcgtggc ctatgccgcg cgctgcgaag gcaaggcgcc gggctgggag   3660
```

-continued

```
ccgctgccgc tgcaatacgc cgactacgcg ctgtggcagc aggagctgct cggcagcgaa   3720
gacgatgccg agagcatggc cggccgccag cgtgagttct ggcgttcctc gctgagcgac   3780
ctgcccgagc aactggcgct gcccgtcgac cacgcacggc cgctcgtgcc gacctaccgc   3840
ggcgatgtgg tcccgctgca gattccgtcg catgtgcatg aacgcatcct gcaactggcg   3900
cgcgacgggc aggccagcgt cttcatggtg ctgcaggccg cactcgcggg cctcctgagc   3960
cgcctcggcg cgggcgacga catcgtcatc ggcagcccgg tcgcggggcg cagcgaccat   4020
gcgctggacg aactcatcgg ctgcttcgtc aacacgctgg tgctgcgcac tgacacctcg   4080
ggccagccga gcctgcgcga gctggtctcg cgcgtgcgcg ccaccaacct cgcggcctat   4140
gcgaaccagg agtttccgta cgaccgcctc gtggagctgc tgcgtccggg ccgctcgcgc   4200
gccaacctgc cgctgttcca ggtcatgctg ggcttccagg gcacgagccg cctgtcgttc   4260
agcctgccgg gcctgtcgat cgcgccgcag ccggtggcca tcgacaccgc gaagttcgac   4320
ctgtcgttca tcctcggcga gcaacgcggt gccgatggcc tgccgggcgg catctccggc   4380
ggcatccagt acagcaccga cctgttcgag cgcagcacgg tcgaggccat gggcgcgcgg   4440
ctggtgcgtt tgctggaaga ggcctgcgag gcgcccgacg atgcggtgag tggcctcgcc   4500
atcctgagcg cggaagaaac cgaccgcctg ctgtccgact ggagcggccg cacgcgcgac   4560
cttgcgccgc tctcgttcgc cgacatggtg gcctcgcatg ccgcggagcg cccgcttgca   4620
gatgcagtgg tgctcgacga cgcgaccgtc agctacgccg aactcgatgc acgcgccaac   4680
cggctctcgc acctgctgcg tgcgcaaggc atcggggttg gcgccatcgt cgcgacagtg   4740
ctgccgcgtt cgctcgacct catcgtggcg cacttggcca tcgtgaaggc cggcgcggcc   4800
tacctgccca tcgaccccaa ccacatggcc gcgcgcagcg ccttcgtgtt cgaggaggcc   4860
gcgcccgccg cggtgctgac gcacgatgcg ctgttgcccg agctggtcgg cgttccccgc   4920
tgcatcgcgc tcgacagcga cagcatggtt gccgcgctgg ccatccagtc ggatacgccg   4980
ctggtgcatg cggccaatcc acaggatgcc gcctacctca tctacacctc cggctccacc   5040
ggcatgccca agggcgtggt ggtgccgcat gcgggcctgg gcagcctcgg caccgcgatg   5100
gcggagcggc tcgtcatcgg ccacggctcg cgcgtgctgc agttctcctc cagcggcttc   5160
gacgcgtcgg tgatggacca gctgatggcc tttggcgccg gtgccgcgct ggtggtgccg   5220
gggccggagc aactgctcgg cacggagctg gccgatctgc tcgagaagca ggccgtgagc   5280
cacgcgctga ttccgcccgc cgcgctcgcg accctgccgc acggcgagtt cccgcacctg   5340
cagacgctgg tggtcggcgg cgatgcctgc accgccgcgc tggcggcgaa gtggtcgcaa   5400
ggccgccgca tgatcaacgc ctacggcccg accgagatca ccatctgcgc gagcatgagc   5460
gcgccgatga cggccgagga gttgccctcc atcggccagc cgatctggaa cacgcggatg   5520
tatgtgctcg acagcgccct gcaaccggtg ccgccgggtg tcgcgggcga gctctacatc   5580
gccggcagcg gcgtggcgcg cggctatctc aaccggccgg cattgagtgc ggaacgcttc   5640
atcgccgacc cgcatggcgc gcccggcagc cgcatgtacc gcagcggcga cctcgcacgc   5700
tggcgcgccg acggcacgct cgacttcctc ggccgcgccg accagcaggt gaagatccgg   5760
ggcttccgca tcgagccggg cgagatcgaa tccgtgctgc tcaagcaccc gttgatcacg   5820
caggccgccg tgatcgcccg cgaggacgtg cccggcgaga agcgcctggt cgcctacttc   5880
gtcgccggtt ccgagccgca gcccaccgag ctgcgcgccc acatggcgca ggccttgccc   5940
gactacatgg tgccttcggc cttcgtgcgc ctgccgtcgc tgccgctcac gcaaagcggc   6000
```

-continued

```
aagctcgaca agaaggcgct gccggtgccc gaccagcagc ccgccgcgct gtacgtggag   6060

ccccgcacgc cgaccgagaa actgctcgcg ggcctctggt ccgagacgct gcacctggag   6120

cgtgtcggca tccacgacaa cttcttcgag atcggcgggc attcgctcat ggcgatccag   6180

ctgggcatgc gcatccgcca gcaggtgcgc gcggacttcc cgcacgccga ggtctacaac   6240

cgcccgacga ttgccgacct ggccgcctgg ctcgacaacg aaggcggcac ggtcgaggcg   6300

ctggacctgt cgcgcgagct cgacctgccc gcgcacatcc gcccgcaggc cactgcaccg   6360

aagctcgcac cgcgccgcgt gttcctcacc ggcgcgagcg gcttcgtcgg cagtcacctg   6420

ctggccgcgc tgttgcgcga caccgcggcc tgcgtggtct gccacgtgcg cgcgcccgac   6480

gagcaggccg gcgagcagcg cctcaagcgc acgctggccc agcgccagct cggtgcgatc   6540

tgggacaacg cgcgcatcaa ggtcgtgacc ggcgacctcg gcaagccgcg cctgggcctc   6600

gatgacgctg ccgtgcaact ggtgcgcgac ggctgcgacg ccatctacca ctgcgccgcg   6660

caggtcgact tcctgcatcc ctacgcgagc ctcaagcccg cgaacgtcga cagcgtggtc   6720

acgctgctcg aatggacggc gcaggggcgc gcgaagagca tgcactacgt ctccacgctg   6780

gctgtgatcg accagaacaa caaggaagac accatcaccg agcaatcggc gctggcctca   6840

tggagcgggc tggtcgacgg ctacagccag agcaagtggg tcggcgatgc gctggcccgc   6900

gaggcgcagg cgcgcggcat gccggtggcg atctaccggc tgggggcagt caccggcgac   6960

cacacgcacg cgatctgcaa tgccgacgac ctgatctggc gcgtggcgca tctctatgcc   7020

gacctggaag cgattcccga tatggacctg ccgctcaacc tcacaccggt ggacgacgtg   7080

gcgcgcgcca tcctcggcct tgcggcgcag gaggcctcgt ggggccaggt gttccacctg   7140

atgagccagg cggcgctgcg ggtgcgcgac attccgcacg tcttcgagcg catgggcatg   7200

cggctggagc cggtcgggct ggagccctgg ctgcagcgcg cgcatgcacg gctggccgtc   7260

gcgcatgacc gcgacctggc cgcggtgctc gccatcctcg accgctacga caccacggcc   7320

acgccgccgc aggtgagcgg cgcggccacg catgcgcagc tcgaggccat cggcgcgccg   7380

atccgcccgg tggaccgcga cctgctgcag cgctacttcg tcgacctggg catcgacacc   7440

aaggcgcgcc gcgccctgga aaccaccact tcatag                             7476
```

<210> SEQ ID NO 6
<211> LENGTH: 2491
<212> TYPE: PRT
<213> ORGANISM: Variovorax paradoxus

<400> SEQUENCE: 6

```
Met Ser Thr Val Asp Gln Leu Gly Arg Thr Ala Pro Leu Thr Ser Gly
1               5                   10                  15

Gln Met Ala Met Trp Leu Gly Ala Lys Phe Ala Ser Pro Asp Thr Asn
            20                  25                  30

Phe Asn Leu Ala Glu Ala Ile Asp Ile Ala Gly Glu Ile Asp Pro Ala
        35                  40                  45

Ile Phe Leu Ala Ala Met Arg Gln Val Ala Asp Glu Val Glu Ala Thr
    50                  55                  60

Arg Leu Ser Phe Ile Asp Thr Pro Gln Gly Pro Arg Gln Val Val Ala
65                  70                  75                  80

Pro Val Phe Thr Gly Glu Ile Pro Tyr Leu Asp Leu Ser Gly Glu Ser
                85                  90                  95

Asp Pro Gln Ala Glu Ala Glu Arg Trp Met His Ala Asp Tyr Thr Arg
            100                 105                 110
```

-continued

```
Ser Ile Asp Leu Ala His Gly Gln Leu Trp Leu Ser Ala Leu Ile Arg
        115                 120                 125

Leu Ala Pro Asp Arg His Ile Trp Tyr His Arg Ser His His Ile Ala
    130                 135                 140

Leu Asp Gly Phe Ser Gly Gly Leu Ile Ala Arg Arg Phe Ala Asp Ile
145                 150                 155                 160

Tyr Thr Ala Met Val Asp Asn Asn Ala Ala Val Pro Glu Asp Ser Arg
                165                 170                 175

Leu Ala Pro Ile Ser Gln Leu Ala Asp Glu Glu His Ala Tyr Arg Glu
            180                 185                 190

Ser Gly Arg Phe Pro Arg Asp Arg Gln Tyr Trp Thr Glu Arg Phe Ala
        195                 200                 205

Asp Ala Pro Asp Pro Leu Ser Leu Ala Ser His Arg Ser Val Asn Val
    210                 215                 220

Gly Gly Leu Leu Arg Gln Thr Val His Leu Pro Ala Ala Ser Val Gln
225                 230                 235                 240

Ala Leu Gln Thr Ile Ala Gln Glu Leu Gly Thr Thr Leu Pro Gln Ile
                245                 250                 255

Leu Ile Ala Thr Thr Ala Ala Tyr Leu Tyr Arg Ala Thr Gly Ile Glu
            260                 265                 270

Asp Met Ala Ile Gly Ile Pro Val Thr Ala Arg His Asn Asp Arg Met
        275                 280                 285

Arg Arg Val Pro Ala Met Val Ala Asn Ala Leu Pro Leu Arg Leu Ala
    290                 295                 300

Met Arg Ala Asp Leu Pro Ile Pro Glu Leu Ile Arg Glu Val Gly Arg
305                 310                 315                 320

Gln Met Arg Gln Ile Leu Arg His Gln Ser Tyr Arg Tyr Glu His Leu
                325                 330                 335

Arg Ser Asp Leu Asn Met Leu Val Asn Asn Arg Gln Leu Phe Thr Thr
            340                 345                 350

Val Val Asn Val Glu Pro Phe Asp Tyr Asp Phe Arg Phe Ala Gly His
        355                 360                 365

Ala Ala Lys Pro Arg Asn Leu Ser Asn Gly Thr Ala Glu Asp Leu Gly
    370                 375                 380

Ile Phe Leu Tyr Glu Arg Gly Asn Gly Gln Asp Leu Gln Ile Asp Phe
385                 390                 395                 400

Asp Ala Asn Pro Ala Val His Thr Ala Glu Glu Leu Ala Asp His Gln
                405                 410                 415

Arg Arg Leu Leu Ala Phe Ile Asp Ala Val Ile Arg Leu Pro Leu Gln
            420                 425                 430

Ala Val Gly Gln Ile Asp Leu Leu Gly Ala Glu Glu Arg Gln Gln Leu
        435                 440                 445

Leu Val Glu Trp Asn Asp Thr Ala His Ala Val Pro Asp Thr His Leu
    450                 455                 460

Thr Ala Leu Ile Glu Ala Gln Leu Ala Ala Asp Pro Gln Ala Ile Ala
465                 470                 475                 480

Leu Arg Phe Asp Gly Glu Ala Met Asn Asn Glu Glu Leu Asn Arg Arg
                485                 490                 495

Ala Asn Arg Leu Ala His Leu Leu Arg Ala Arg Gly Ala Gly Pro Glu
            500                 505                 510

Arg Thr Val Ala Leu Ala Ile Pro Arg Ser Met Asp Leu Met Ile Ala
        515                 520                 525

Leu Leu Ala Thr Leu Lys Thr Gly Ala Ala Tyr Leu Pro Val Asp Pro
```

```
    530                 535                 540

Asp Phe Pro Ala Asp Arg Ile Ala Phe Met Leu Gly Asp Ala Gln Pro
545                 550                 555                 560

Val Cys Leu Val Thr Thr Glu Ala Leu Ala Glu Ser Leu Pro Ala Ala
                565                 570                 575

Ala Pro Thr Leu Leu Leu Asp Val Ala Gln Thr Ile Ala Asp Leu Glu
            580                 585                 590

Ser Cys Asn Asp Thr Asn Pro Gly Ile Ala Ile Asp Pro Ser His Pro
        595                 600                 605

Ala Tyr Val Ile Tyr Thr Ser Gly Ser Thr Gly Met Pro Lys Gly Ala
    610                 615                 620

Val Val Ser His Arg Ala Ile Val Asn Arg Leu Arg Trp Met Gln Asp
625                 630                 635                 640

Arg Tyr Gly Leu Gln Ala Asp Asp Arg Val Leu Gln Lys Thr Pro Ser
                645                 650                 655

Ser Phe Asp Val Ser Val Trp Glu Phe Phe Trp Pro Leu Ile Asp Gly
            660                 665                 670

Ala Thr Leu Val Leu Ala Lys Pro Gly Gly His Lys Asp Ala Ala Tyr
        675                 680                 685

Leu Ala Gly Leu Ile Ala Glu Glu Gly Ile Thr Thr Ile His Phe Val
    690                 695                 700

Pro Ser Met Leu Glu Val Phe Leu Leu Glu Pro Thr Ala Gly Ala Cys
705                 710                 715                 720

Thr Thr Leu Arg Arg Val Ile Cys Ser Gly Glu Ala Leu Ser Pro Ala
                725                 730                 735

Leu Gln Ser Gln Phe Gln Gln His Leu Ser Cys Glu Leu His Asn Leu
            740                 745                 750

Tyr Gly Pro Thr Glu Ala Ala Val Asp Val Thr Ser Trp Glu Cys Glu
        755                 760                 765

Arg Thr Asp Asp Ala Glu Ala Ser Ser Val Pro Ile Gly Arg Pro Ile
    770                 775                 780

Trp Asn Thr Gln Met His Val Leu Asp Ser Gly Leu Gln Pro Val Pro
785                 790                 795                 800

Ala Gly Val Thr Gly Glu Leu Tyr Ile Ala Gly Val Gly Leu Ala Arg
                805                 810                 815

Gly Tyr Leu Lys Arg Pro Leu Leu Ser Ala Glu Arg Phe Ile Ala Asn
            820                 825                 830

Pro Tyr Gly Thr Pro Gly Ser Arg Met Tyr Arg Thr Gly Asp Leu Ala
        835                 840                 845

Arg Trp Arg Lys Asp Gly Ser Leu Asp Phe Leu Gly Arg Ala Asp Gln
    850                 855                 860

Gln Val Lys Ile Arg Gly Leu Arg Ile Glu Pro Gly Glu Ile Glu Ser
865                 870                 875                 880

Val Leu Leu Gln His Pro Gln Val Ala Gln Ala Ala Val Val Ala Arg
                885                 890                 895

Glu Asp Val Pro Gly Glu Lys Arg Leu Val Ala Tyr Val Val Ala Thr
            900                 905                 910

Asp Ala Ala Asp Pro Gln Ala Ala Glu Leu Arg Thr Arg Leu Ala Gln
        915                 920                 925

Ser Leu Pro Glu Tyr Met Val Pro Ser Ala Phe Val Ser Leu Pro Ser
    930                 935                 940

Leu Pro Leu Gly Pro Ser Gly Lys Leu Asp Arg Lys Ala Leu Pro Pro
945                 950                 955                 960
```

-continued

```
Pro Glu Val Gln Ala Ala Thr Pro Tyr Ala Ala Pro Arg Thr Pro Thr
                965                 970                 975

Glu Lys Ile Leu Ala Gly Leu Trp Ala Glu Thr Leu His Leu Pro Arg
            980                 985                 990

Val Gly Val Asn Asp Asn Phe Phe  Glu Leu Gly Gly His  Ser Leu Met
        995                 1000                 1005

Ile Val  Gln Leu Met Ser Met  Ile Arg Gln Gln Phe  Met Ile Asp
    1010                 1015                 1020

Leu Pro  Val Asp Thr Leu Phe  Gln Val Ser Thr Ile  Ala Gly Leu
    1025                 1030                 1035

Ala Glu  Leu Leu Asp Gln Glu  Ser Val Ala Arg Pro  Ser Leu Thr
    1040                 1045                 1050

Pro Met  Pro Arg Pro Ala Arg  Ile Pro Leu Ser Phe  Ala Gln Arg
    1055                 1060                 1065

Arg Leu  Trp Leu Met Asn Gln  Leu Glu Gly Ala Asn  Pro Ala Tyr
    1070                 1075                 1080

Asn Met  Pro Leu Ala Leu Arg  Leu Ser Gly Val Leu  Asp Arg Thr
    1085                 1090                 1095

Ala Leu  His Ala Ala Leu Gly  Asp Leu Val Gln Arg  His Glu Ser
    1100                 1105                 1110

Leu Arg  Thr Val Tyr Pro Asn  Glu Asp Gly Leu Pro  Tyr Gln His
    1115                 1120                 1125

Ile Leu  Asp Gly Ala Asp Ala  Arg Pro Ala Val Ile  Glu Ala Asp
    1130                 1135                 1140

Ser Ser  Glu Glu Glu Ile Ala  Ala Gln Leu His Ala  Ala Ala Gly
    1145                 1150                 1155

His Ala  Phe Asp Leu Gly Ser  Ala Ala Pro Leu Arg  Val Tyr Leu
    1160                 1165                 1170

Phe Lys  Leu Ala Gly Asp Glu  His Val Leu Leu Leu  Leu Thr His
    1175                 1180                 1185

His Ile  Ala Gly Asp Gly Ala  Ser Leu Leu Pro Leu  Ala Arg Asp
    1190                 1195                 1200

Ile Ser  Val Ala Tyr Ala Ala  Arg Cys Glu Gly Lys  Ala Pro Gly
    1205                 1210                 1215

Trp Glu  Pro Leu Pro Leu Gln  Tyr Ala Asp Tyr Ala  Leu Trp Gln
    1220                 1225                 1230

Gln Glu  Leu Leu Gly Ser Glu  Asp Asp Ala Glu Ser  Met Ala Gly
    1235                 1240                 1245

Arg Gln  Arg Glu Phe Trp Arg  Ser Ser Leu Ser Asp  Leu Pro Glu
    1250                 1255                 1260

Gln Leu  Ala Leu Pro Val Asp  His Ala Arg Pro Leu  Val Pro Thr
    1265                 1270                 1275

Tyr Arg  Gly Asp Val Val Pro  Leu Gln Ile Pro Ser  His Val His
    1280                 1285                 1290

Glu Arg  Ile Leu Gln Leu Ala  Arg Asp Gly Gln Ala  Ser Val Phe
    1295                 1300                 1305

Met Val  Leu Gln Ala Ala Leu  Ala Gly Leu Leu Ser  Arg Leu Gly
    1310                 1315                 1320

Ala Gly  Asp Asp Ile Val Ile  Gly Ser Pro Val Ala  Gly Arg Ser
    1325                 1330                 1335

Asp His  Ala Leu Asp Glu Leu  Ile Gly Cys Phe Val  Asn Thr Leu
    1340                 1345                 1350
```

-continued

```
Val Leu  Arg Thr Asp Thr Ser  Gly Gln Pro Ser Leu  Arg Glu Leu
    1355                 1360                 1365

Val Ser  Arg Val Arg Ala Thr  Asn Leu Ala Ala Tyr  Ala Asn Gln
    1370                 1375                 1380

Glu Phe  Pro Tyr Asp Arg Leu  Val Glu Leu Leu Arg  Pro Gly Arg
    1385                 1390                 1395

Ser Arg  Ala Asn Leu Pro Leu  Phe Gln Val Met Leu  Gly Phe Gln
    1400                 1405                 1410

Gly Thr  Ser Arg Leu Ser Phe  Ser Leu Pro Gly Leu  Ser Ile Ala
    1415                 1420                 1425

Pro Gln  Pro Val Ala Ile Asp  Thr Ala Lys Phe Asp  Leu Ser Phe
    1430                 1435                 1440

Ile Leu  Gly Glu Gln Arg Gly  Ala Asp Gly Leu Pro  Gly Gly Ile
    1445                 1450                 1455

Ser Gly  Gly Ile Gln Tyr Ser  Thr Asp Leu Phe Glu  Arg Ser Thr
    1460                 1465                 1470

Val Glu  Ala Met Gly Ala Arg  Leu Val Arg Leu Leu  Glu Glu Ala
    1475                 1480                 1485

Cys Glu  Ala Pro Asp Asp Ala  Val Ser Gly Leu Ala  Ile Leu Ser
    1490                 1495                 1500

Ala Glu  Glu Thr Asp Arg Leu  Leu Ser Asp Trp Ser  Gly Arg Thr
    1505                 1510                 1515

Arg Asp  Leu Ala Pro Leu Ser  Phe Ala Asp Met Val  Ala Ser His
    1520                 1525                 1530

Ala Ala  Glu Arg Pro Leu Ala  Asp Ala Val Val Leu  Asp Asp Ala
    1535                 1540                 1545

Thr Val  Ser Tyr Ala Glu Leu  Asp Ala Arg Ala Asn  Arg Leu Ser
    1550                 1555                 1560

His Leu  Leu Arg Ala Gln Gly  Ile Gly Val Gly Ala  Ile Val Ala
    1565                 1570                 1575

Thr Val  Leu Pro Arg Ser Leu  Asp Leu Ile Val Ala  His Leu Ala
    1580                 1585                 1590

Ile Val  Lys Ala Gly Ala Ala  Tyr Leu Pro Ile Asp  Pro Asn His
    1595                 1600                 1605

Met Ala  Ala Arg Ser Ala Phe  Val Phe Glu Glu Ala  Ala Pro Ala
    1610                 1615                 1620

Ala Val  Leu Thr His Asp Ala  Leu Leu Pro Glu Leu  Val Gly Val
    1625                 1630                 1635

Pro Arg  Cys Ile Ala Leu Asp  Ser Asp Ser Met Val  Ala Ala Leu
    1640                 1645                 1650

Ala Ile  Gln Ser Asp Thr Pro  Leu Val His Ala Ala  Asn Pro Gln
    1655                 1660                 1665

Asp Ala  Ala Tyr Leu Ile Tyr  Thr Ser Gly Ser Thr  Gly Met Pro
    1670                 1675                 1680

Lys Gly  Val Val Val Pro His  Ala Gly Leu Gly Ser  Leu Gly Thr
    1685                 1690                 1695

Ala Met  Ala Glu Arg Leu Val  Ile Gly His Gly Ser  Arg Val Leu
    1700                 1705                 1710

Gln Phe  Ser Ser Ser Gly Phe  Asp Ala Ser Val Met  Asp Gln Leu
    1715                 1720                 1725

Met Ala  Phe Gly Ala Gly Ala  Ala Leu Val Val Pro  Gly Pro Glu
    1730                 1735                 1740

Gln Leu  Leu Gly Thr Glu Leu  Ala Asp Leu Leu Glu  Lys Gln Ala
```

-continued

```
    1745                1750                1755

Val Ser  His Ala Leu Ile Pro  Pro Ala Ala Leu Ala  Thr Leu Pro
    1760                1765                1770

His Gly  Glu Phe Pro His Leu  Gln Thr Leu Val Val  Gly Gly Asp
    1775                1780                1785

Ala Cys  Thr Ala Ala Leu Ala  Ala Lys Trp Ser Gln  Gly Arg Arg
    1790                1795                1800

Met Ile  Asn Ala Tyr Gly Pro  Thr Glu Ile Thr Ile  Cys Ala Ser
    1805                1810                1815

Met Ser  Ala Pro Met Thr Ala  Glu Glu Leu Pro Ser  Ile Gly Gln
    1820                1825                1830

Pro Ile  Trp Asn Thr Arg Met  Tyr Val Leu Asp Ser  Ala Leu Gln
    1835                1840                1845

Pro Val  Pro Pro Gly Val Ala  Gly Glu Leu Tyr Ile  Ala Gly Ser
    1850                1855                1860

Gly Val  Ala Arg Gly Tyr Leu  Asn Arg Pro Ala Leu  Ser Ala Glu
    1865                1870                1875

Arg Phe  Ile Ala Asp Pro His  Gly Ala Pro Gly Ser  Arg Met Tyr
    1880                1885                1890

Arg Ser  Gly Asp Leu Ala Arg  Trp Arg Ala Asp Gly  Thr Leu Asp
    1895                1900                1905

Phe Leu  Gly Arg Ala Asp Gln  Gln Val Lys Ile Arg  Gly Phe Arg
    1910                1915                1920

Ile Glu  Pro Gly Glu Ile Glu  Ser Val Leu Leu Lys  His Pro Leu
    1925                1930                1935

Ile Thr  Gln Ala Ala Val Ile  Ala Arg Glu Asp Val  Pro Gly Glu
    1940                1945                1950

Lys Arg  Leu Val Ala Tyr Phe  Val Ala Gly Ser Glu  Pro Gln Pro
    1955                1960                1965

Thr Glu  Leu Arg Ala His Met  Ala Gln Ala Leu Pro  Asp Tyr Met
    1970                1975                1980

Val Pro  Ser Ala Phe Val Arg  Leu Pro Ser Leu Pro  Leu Thr Gln
    1985                1990                1995

Ser Gly  Lys Leu Asp Lys Lys  Ala Leu Pro Val Pro  Asp Gln Gln
    2000                2005                2010

Pro Ala  Ala Leu Tyr Val Glu  Pro Arg Thr Pro Thr  Glu Lys Leu
    2015                2020                2025

Leu Ala  Gly Leu Trp Ser Glu  Thr Leu His Leu Glu  Arg Val Gly
    2030                2035                2040

Ile His  Asp Asn Phe Phe Glu  Ile Gly Gly His Ser  Leu Met Ala
    2045                2050                2055

Ile Gln  Leu Gly Met Arg Ile  Arg Gln Gln Val Arg  Ala Asp Phe
    2060                2065                2070

Pro His  Ala Glu Val Tyr Asn  Arg Pro Thr Ile Ala  Asp Leu Ala
    2075                2080                2085

Ala Trp  Leu Asp Asn Glu Gly  Gly Thr Val Glu Ala  Leu Asp Leu
    2090                2095                2100

Ser Arg  Glu Leu Asp Leu Pro  Ala His Ile Arg Pro  Gln Ala Thr
    2105                2110                2115

Ala Pro  Lys Leu Ala Pro Arg  Arg Val Phe Leu Thr  Gly Ala Ser
    2120                2125                2130

Gly Phe  Val Gly Ser His Leu  Leu Ala Ala Leu Leu  Arg Asp Thr
    2135                2140                2145
```

-continued

```
Ala Ala  Cys Val Val Cys His  Val Arg Ala Pro Asp  Glu Gln Ala
    2150                 2155                 2160

Gly Glu  Gln Arg Leu Lys Arg  Thr Leu Ala Gln Arg  Gln Leu Gly
    2165                 2170                 2175

Ala Ile  Trp Asp Asn Ala Arg  Ile Lys Val Val Thr  Gly Asp Leu
    2180                 2185                 2190

Gly Lys  Pro Arg Leu Gly Leu  Asp Asp Ala Ala Val  Gln Leu Val
    2195                 2200                 2205

Arg Asp  Gly Cys Asp Ala Ile  Tyr His Cys Ala Ala  Gln Val Asp
    2210                 2215                 2220

Phe Leu  His Pro Tyr Ala Ser  Leu Lys Pro Ala Asn  Val Asp Ser
    2225                 2230                 2235

Val Val  Thr Leu Leu Glu Trp  Thr Ala Gln Gly Arg  Ala Lys Ser
    2240                 2245                 2250

Met His  Tyr Val Ser Thr Leu  Ala Val Ile Asp Gln  Asn Asn Lys
    2255                 2260                 2265

Glu Asp  Thr Ile Thr Glu Gln  Ser Ala Leu Ala Ser  Trp Ser Gly
    2270                 2275                 2280

Leu Val  Asp Gly Tyr Ser Gln  Ser Lys Trp Val Gly  Asp Ala Leu
    2285                 2290                 2295

Ala Arg  Glu Ala Gln Ala Arg  Gly Met Pro Val Ala  Ile Tyr Arg
    2300                 2305                 2310

Leu Gly  Ala Val Thr Gly Asp  His Thr His Ala Ile  Cys Asn Ala
    2315                 2320                 2325

Asp Asp  Leu Ile Trp Arg Val  Ala His Leu Tyr Ala  Asp Leu Glu
    2330                 2335                 2340

Ala Ile  Pro Asp Met Asp Leu  Pro Leu Asn Leu Thr  Pro Val Asp
    2345                 2350                 2355

Asp Val  Ala Arg Ala Ile Leu  Gly Leu Ala Ala Gln  Glu Ala Ser
    2360                 2365                 2370

Trp Gly  Gln Val Phe His Leu  Met Ser Gln Ala Ala  Leu Arg Val
    2375                 2380                 2385

Arg Asp  Ile Pro His Val Phe  Glu Arg Met Gly Met  Arg Leu Glu
    2390                 2395                 2400

Pro Val  Gly Leu Glu Pro Trp  Leu Gln Arg Ala His  Ala Arg Leu
    2405                 2410                 2415

Ala Val  Ala His Asp Arg Asp  Leu Ala Ala Val Leu  Ala Ile Leu
    2420                 2425                 2430

Asp Arg  Tyr Asp Thr Thr Ala  Thr Pro Pro Gln Val  Ser Gly Ala
    2435                 2440                 2445

Ala Thr  His Ala Gln Leu Glu  Ala Ile Gly Ala Pro  Ile Arg Pro
    2450                 2455                 2460

Val Asp  Arg Asp Leu Leu Gln  Arg Tyr Phe Val Asp  Leu Gly Ile
    2465                 2470                 2475

Asp Thr  Lys Ala Arg Arg Ala  Leu Glu Thr Thr Thr  Ser
    2480                 2485                 2490
```

<210> SEQ ID NO 7
<211> LENGTH: 1320
<212> TYPE: DNA
<213> ORGANISM: Variovorax paradoxus

<400> SEQUENCE: 7

```
atggcacgct atctcatcgc agcaaccgcc ttgccgggac acgtcctgcc gatgctggcc     60
```

```
atcgcgcagc atctggtgaa ccaggggcac gaggtgcggg tgcacaccgc gagccagttc    120

agggcgcagg ccgaggcgac cggtgcgggc ttcacgccct tcgagcgcac gatcgacttc    180

gactaccgcg acctggacaa gcgctttccc gagcgccagc gcatcgcctc ggcgcatgcg    240

cagctgtgct tcggcctgaa gcacttcttt gccgatgcga tggccgcgca gcatgcgggc    300

ctgcaatcga tcctcgaaga cttcgaggcc gatgccatcg tggtcgacac gatgttctgc    360

ggcactttcc cgctgctgct aggcaaggag cgcgaagacc gcccggccat cgtcggcatc    420

ggcatctcgg cgctgccgct ctcgagctgc gacaccgcct tcttcggcac cgcgctgccg    480

ccgtcgtcca cgccggaagg gcgggtgcgc aacaaggcga tgaacgccaa cctcaaacag    540

gcgatgttcg gcgaggtgca acgctacttc gacacgctgc tcgcgcgttc gggcctggcc    600

gcgctgcccg atttcttcgt cgatgcgatg gtgaagctgc ccgatcttta cctgcagctc    660

accgcgcctt cgttcgaata cccgcgcagc gacctgcccg cgtcggtgca tttcgtcggc    720

ccgctgctct cgcccgcgag ccgcgacttc acgccgcccg agtggtggca cgagctggac    780

gacggccgct cggtcgtgct ggtcacgcag ggcacgctgg ccaaccagaa tccgtcgcag    840

ctgatcggcc cgacgctgca ggcgctggcc ggcgacaaga acatcctcgt catcgccacc    900

accggcggcc cggtgccgcc cgccctgacg gtgaacctgc ccgccaacgc ccgcgtggtg    960

ccgttcctgc cctacgaccg gctgctgccc aagctgcacg cgatggtcac caacggcggc   1020

tacggctcgg tcaaccatgc attgagcctc ggtgtgccgc tggtggtggc cggcacctcc   1080

gaagagaagc ccgagatcgc cgcgcgcgtg gcctggtcgg gcgcgggcat caacctcgcc   1140

accggccagc cgaccgcgcg ccaggtcggc gacgcggtgc gcaaggtact gggcaactcg   1200

acctatcgcc agcgtgcggc ggtgctgcgt gaggacttcg cttgccatcg cgcgctgacc   1260

ggcatcgccg gcgccctcga ggcacttctg caaaccttcg catccgcgga aatggcttga   1320
```

```
<210> SEQ ID NO 8
<211> LENGTH: 439
<212> TYPE: PRT
<213> ORGANISM: Variovorax paradoxus

<400> SEQUENCE: 8

Met Ala Arg Tyr Leu Ile Ala Ala Thr Ala Leu Pro Gly His Val Leu
1               5                   10                  15

Pro Met Leu Ala Ile Ala Gln His Leu Val Asn Gln Gly His Glu Val
            20                  25                  30

Arg Val His Thr Ala Ser Gln Phe Arg Ala Gln Ala Glu Ala Thr Gly
        35                  40                  45

Ala Gly Phe Thr Pro Phe Glu Arg Thr Ile Asp Phe Asp Tyr Arg Asp
    50                  55                  60

Leu Asp Lys Arg Phe Pro Glu Arg Gln Arg Ile Ala Ser Ala His Ala
65                  70                  75                  80

Gln Leu Cys Phe Gly Leu Lys His Phe Phe Ala Asp Ala Met Ala Ala
                85                  90                  95

Gln His Ala Gly Leu Gln Ser Ile Leu Glu Asp Phe Glu Ala Asp Ala
            100                 105                 110

Ile Val Val Asp Thr Met Phe Cys Gly Thr Phe Pro Leu Leu Leu Gly
        115                 120                 125

Lys Glu Arg Glu Asp Arg Pro Ala Ile Val Gly Ile Gly Ile Ser Ala
    130                 135                 140

Leu Pro Leu Ser Ser Cys Asp Thr Ala Phe Phe Gly Thr Ala Leu Pro
```

```
145                 150                 155                 160

Pro Ser Ser Thr Pro Glu Gly Arg Val Arg Asn Lys Ala Met Asn Ala
                165                 170                 175

Asn Leu Lys Gln Ala Met Phe Gly Glu Val Gln Arg Tyr Phe Asp Thr
            180                 185                 190

Leu Leu Ala Arg Ser Gly Leu Ala Ala Leu Pro Asp Phe Phe Val Asp
        195                 200                 205

Ala Met Val Lys Leu Pro Asp Leu Tyr Leu Gln Leu Thr Ala Pro Ser
    210                 215                 220

Phe Glu Tyr Pro Arg Ser Asp Leu Pro Ala Ser Val His Phe Val Gly
225                 230                 235                 240

Pro Leu Leu Ser Pro Ala Ser Arg Asp Phe Thr Pro Pro Glu Trp Trp
                245                 250                 255

His Glu Leu Asp Asp Gly Arg Ser Val Val Leu Val Thr Gln Gly Thr
            260                 265                 270

Leu Ala Asn Gln Asn Pro Ser Gln Leu Ile Gly Pro Thr Leu Gln Ala
        275                 280                 285

Leu Ala Gly Asp Lys Asn Ile Leu Val Ile Ala Thr Thr Gly Gly Pro
    290                 295                 300

Val Pro Pro Ala Leu Thr Val Asn Leu Pro Ala Asn Ala Arg Val Val
305                 310                 315                 320

Pro Phe Leu Pro Tyr Asp Arg Leu Leu Pro Lys Leu His Ala Met Val
                325                 330                 335

Thr Asn Gly Gly Tyr Gly Ser Val Asn His Ala Leu Ser Leu Gly Val
            340                 345                 350

Pro Leu Val Val Ala Gly Thr Ser Glu Glu Lys Pro Glu Ile Ala Ala
        355                 360                 365

Arg Val Ala Trp Ser Gly Ala Gly Ile Asn Leu Ala Thr Gly Gln Pro
    370                 375                 380

Thr Ala Arg Gln Val Gly Asp Ala Val Arg Lys Val Leu Gly Asn Ser
385                 390                 395                 400

Thr Tyr Arg Gln Arg Ala Ala Val Leu Arg Glu Asp Phe Ala Cys His
                405                 410                 415

Arg Ala Leu Thr Gly Ile Ala Gly Ala Leu Glu Ala Leu Leu Gln Thr
            420                 425                 430

Phe Ala Ser Ala Glu Met Ala
        435


<210> SEQ ID NO 9
<211> LENGTH: 213
<212> TYPE: DNA
<213> ORGANISM: Variovorax paradoxus

<400> SEQUENCE: 9

atgagcaacc cgttcgacga caagaacgcc agcttccagg tgctggtgaa cgacgagggc      60

cagcactcgc tgtggcccgc cttcatcgcc gtgcccgccg gctggcaggt ggcgctggcg     120

ccgaccgacc gcgacgcctg cagcgcctac atcgcggcga actggcagga catgcgcccg     180

cgttcgctgg tggtggccac ggcggccggc tga                                  213


<210> SEQ ID NO 10
<211> LENGTH: 70
<212> TYPE: PRT
<213> ORGANISM: Variovorax paradoxus

<400> SEQUENCE: 10
```

```
Met Ser Asn Pro Phe Asp Asp Lys Asn Ala Ser Phe Gln Val Leu Val
1               5                   10                  15

Asn Asp Glu Gly Gln His Ser Leu Trp Pro Ala Phe Ile Ala Val Pro
            20                  25                  30

Ala Gly Trp Gln Val Ala Leu Ala Pro Thr Asp Arg Asp Ala Cys Ser
        35                  40                  45

Ala Tyr Ile Ala Ala Asn Trp Gln Asp Met Arg Pro Arg Ser Leu Val
    50                  55                  60

Val Ala Thr Ala Ala Gly
65                  70
```

<210> SEQ ID NO 11
<211> LENGTH: 969
<212> TYPE: DNA
<213> ORGANISM: Variovorax paradoxus

<400> SEQUENCE: 11

```
atgtccttcc cgttcggtgc cgtcgtcgtc acctatttcc cgaccggcga gcaagtggcg     60

aacctccatt cgctggcggc ctcgtgtccg cacctctgcg tggtcgacaa cacgccgcag    120

gtgggcgatt ggcatgcggc gctcgtcgat gcgggcgttt cggtgctgca caacggcaac    180

cgcggcggca tcgcgggcgc cttcaaccgc ggcatcatcg acctcgaagc gcggggcgcc    240

gaactcttct tcctgctcga ccaggattcg aagctgccac ccggctactt cgatgccatg    300

tgcgaggctg cgatggtggc ccgggagcgg aagggcgagg gcaatggtga ggaagacgcg    360

gccttcctga tcggcccgct cgtccacgac acgaacctgg acgcgctgat cccgcaattc    420

ggcctccagg gcaaacgcgt ctaccagttc gacctgcggc agcccttcac cgagccgctg    480

atgcgctgcg ccttcatgat ttcctcgggc tccctgattt cgcgcggcgc ctgggcccgg    540

atcggccggt tcgacgagcg ctatgtgatc gaccacgtgg acaccgacta ctgcatgcgt    600

gccctgggtc gcggcgtgcc gctctacctg aatccgcacg tcgtgctgcg gcaccagatt    660

ggcgacatcc gtgcccggtc gctgttcggc tggaagatcc acttcatcaa ctacccggcc    720

gcgcggcgct actacatcgc gcgcaatgcc atcgatctct cgcgggcgca tgtgcgcgcc    780

tttcccgcga tcctgttcat caacgtttac acgctcaagc agatcctgcc gatgctgatg    840

ttcgagcgcg accgcttcaa gaagaccatc gcgctgatgc tcggctgctt cgatggcctg    900

ttcgggcggc tcgggggcct cggcgaggtg catccgcgga tgggcaaata cctgggccgc    960

agcgattga                                                            969
```

<210> SEQ ID NO 12
<211> LENGTH: 322
<212> TYPE: PRT
<213> ORGANISM: Variovorax paradoxus

<400> SEQUENCE: 12

```
Met Ser Phe Pro Phe Gly Ala Val Val Val Thr Tyr Phe Pro Thr Gly
1               5                   10                  15

Glu Gln Val Ala Asn Leu His Ser Leu Ala Ala Ser Cys Pro His Leu
            20                  25                  30

Cys Val Val Asp Asn Thr Pro Gln Val Gly Asp Trp His Ala Ala Leu
        35                  40                  45

Val Asp Ala Gly Val Ser Val Leu His Asn Gly Asn Arg Gly Gly Ile
    50                  55                  60

Ala Gly Ala Phe Asn Arg Gly Ile Ile Asp Leu Glu Ala Arg Gly Ala
```

-continued

```
65                  70                  75                  80

Glu Leu Phe Phe Leu Leu Asp Gln Asp Ser Lys Leu Pro Pro Gly Tyr
                85                  90                  95

Phe Asp Ala Met Cys Glu Ala Ala Met Val Ala Arg Glu Arg Lys Gly
            100                 105                 110

Glu Gly Asn Gly Glu Glu Asp Ala Ala Phe Leu Ile Gly Pro Leu Val
        115                 120                 125

His Asp Thr Asn Leu Asp Ala Leu Ile Pro Gln Phe Gly Leu Gln Gly
    130                 135                 140

Lys Arg Val Tyr Gln Phe Asp Leu Arg Gln Pro Phe Thr Glu Pro Leu
145                 150                 155                 160

Met Arg Cys Ala Phe Met Ile Ser Ser Gly Ser Leu Ile Ser Arg Gly
                165                 170                 175

Ala Trp Ala Arg Ile Gly Arg Phe Asp Glu Arg Tyr Val Ile Asp His
            180                 185                 190

Val Asp Thr Asp Tyr Cys Met Arg Ala Leu Gly Arg Gly Val Pro Leu
        195                 200                 205

Tyr Leu Asn Pro His Val Val Leu Arg His Gln Ile Gly Asp Ile Arg
    210                 215                 220

Ala Arg Ser Leu Phe Gly Trp Lys Ile His Phe Ile Asn Tyr Pro Ala
225                 230                 235                 240

Ala Arg Arg Tyr Tyr Ile Ala Arg Asn Ala Ile Asp Leu Ser Arg Ala
                245                 250                 255

His Val Arg Ala Phe Pro Ala Ile Leu Phe Ile Asn Val Tyr Thr Leu
            260                 265                 270

Lys Gln Ile Leu Pro Met Leu Met Phe Glu Arg Asp Arg Phe Lys Lys
        275                 280                 285

Thr Ile Ala Leu Met Leu Gly Cys Phe Asp Gly Leu Phe Gly Arg Leu
    290                 295                 300

Gly Gly Leu Gly Glu Val His Pro Arg Met Gly Lys Tyr Leu Gly Arg
305                 310                 315                 320

Ser Asp
```

<210> SEQ ID NO 13
<211> LENGTH: 1260
<212> TYPE: DNA
<213> ORGANISM: Variovorax paradoxus

<400> SEQUENCE: 13

```
ttgaccgcca cccttccagc gccgcgcgta cgccgcgccg cgctcgcctt catcttcgtc      60

acggtgctga tcgacttcat ggcgttcggc ctgatcctgc ccggcctgcc gcacctggtg     120

gagcggctgg ccggcggcag cacggtaacg gcggcgtact ggatcgctgt gttcggcacc     180

gcgttcgcgg cgatccagtt cgtgagctcg ccgatccagg gcgcgctgtc cgaccgcttc     240

gggcggcggc cggtgatcct gctgtcgtgc ttcggcctcg gcgtggattt cgtgttcatg     300

gccctggccg acagcctgcc gtggctgttc gtcggccggg tggtctccgg cgtgttctcg     360

gccagcttca ccatcgccaa tgcctacatc gccgatgtga cgctgccgga ggagcgcgcc     420

cgcagctacg gcatcgtggg ggccgcgttc ggcatgggcc tggtgttcgg gccggtgctc     480

ggcgggcaac tgagccacat cgatccgcgc ctgccgttct ggttcgcggc cggcttgacg     540

ctgctcagct tctgctacgg atggttcgtg ttgcccgaat cgctgccgcc cgagcggcgt     600

gcccgcaagt tcgactggtc gcatgccaat ccggttggga cgctggtgct gctcaagcgc     660
```

-continued

```
tatccgcagg tgttcggact ggcggcggtg atcttcctcg tgaacctggc tcagtacgtc    720

tatcccagcg tgttcgtgct gttcgccgac taccggtatc actggaagga agacgccgtg    780

ggctgggtgc tcggcgcggt gggcgtgctc agcgtgctgg tcaatgcgct gttgatcggg    840

ccgggcgtga agcgcttcgg cgagcgccgc gccctgttgc tcggcatggg cttcggcgtg    900

ctcggcttcg tcatcatcgg gtttgccgac gctggatgga tcctcctggc cggggtgccg    960

ttcggcattc tgctggcgtt cgccggaccg gcggcgcagg cgctggtcac gctgcaggtc   1020

ggcaccgccg agcagggccg catccagggg gcgctcacca gcctggtgtc ggtggcgggc   1080

atcgtcgggc cggcgatgtt cgccggcagc ttcggttact tcatcggcgc ggacgcgccg   1140

gtgcacttgc cgggcgcgcc gtttttcctc gctgcggcgt tcctctgcat cggcacgctg   1200

atcgcgtggc gctacgcaca gccgaagccc gcgacggcag cggtgcccga gccgacctga   1260


<210> SEQ ID NO 14
<211> LENGTH: 419
<212> TYPE: PRT
<213> ORGANISM: Variovorax paradoxus

<400> SEQUENCE: 14

Met Thr Ala Thr Leu Pro Ala Pro Arg Val Arg Arg Ala Ala Leu Ala
1               5                   10                  15

Phe Ile Phe Val Thr Val Leu Ile Asp Phe Met Ala Phe Gly Leu Ile
            20                  25                  30

Leu Pro Gly Leu Pro His Leu Val Glu Arg Leu Ala Gly Gly Ser Thr
        35                  40                  45

Val Thr Ala Ala Tyr Trp Ile Ala Val Phe Gly Thr Ala Phe Ala Ala
    50                  55                  60

Ile Gln Phe Val Ser Ser Pro Ile Gln Gly Ala Leu Ser Asp Arg Phe
65                  70                  75                  80

Gly Arg Arg Pro Val Ile Leu Leu Ser Cys Phe Gly Leu Gly Val Asp
                85                  90                  95

Phe Val Phe Met Ala Leu Ala Asp Ser Leu Pro Trp Leu Phe Val Gly
            100                 105                 110

Arg Val Val Ser Gly Val Phe Ser Ala Ser Phe Thr Ile Ala Asn Ala
        115                 120                 125

Tyr Ile Ala Asp Val Thr Leu Pro Glu Glu Arg Ala Arg Ser Tyr Gly
    130                 135                 140

Ile Val Gly Ala Ala Phe Gly Met Gly Leu Val Phe Gly Pro Val Leu
145                 150                 155                 160

Gly Gly Gln Leu Ser His Ile Asp Pro Arg Leu Pro Phe Trp Phe Ala
                165                 170                 175

Ala Gly Leu Thr Leu Leu Ser Phe Cys Tyr Gly Trp Phe Val Leu Pro
            180                 185                 190

Glu Ser Leu Pro Pro Glu Arg Arg Ala Arg Lys Phe Asp Trp Ser His
        195                 200                 205

Ala Asn Pro Val Gly Thr Leu Val Leu Leu Lys Arg Tyr Pro Gln Val
    210                 215                 220

Phe Gly Leu Ala Ala Val Ile Phe Leu Val Asn Leu Ala Gln Tyr Val
225                 230                 235                 240

Tyr Pro Ser Val Phe Val Leu Phe Ala Asp Tyr Arg Tyr His Trp Lys
                245                 250                 255

Glu Asp Ala Val Gly Trp Val Leu Gly Ala Val Gly Val Leu Ser Val
            260                 265                 270
```

-continued

```
Leu Val Asn Ala Leu Leu Ile Gly Pro Gly Val Lys Arg Phe Gly Glu
        275                 280                 285

Arg Arg Ala Leu Leu Leu Gly Met Gly Phe Gly Val Leu Gly Phe Val
    290                 295                 300

Ile Ile Gly Phe Ala Asp Ala Gly Trp Ile Leu Leu Ala Gly Val Pro
305                 310                 315                 320

Phe Gly Ile Leu Leu Ala Phe Ala Gly Pro Ala Ala Gln Ala Leu Val
                325                 330                 335

Thr Leu Gln Val Gly Thr Ala Glu Gln Gly Arg Ile Gln Gly Ala Leu
            340                 345                 350

Thr Ser Leu Val Ser Val Ala Gly Ile Val Gly Pro Ala Met Phe Ala
        355                 360                 365

Gly Ser Phe Gly Tyr Phe Ile Gly Ala Asp Ala Pro Val His Leu Pro
    370                 375                 380

Gly Ala Pro Phe Phe Leu Ala Ala Ala Phe Leu Cys Ile Gly Thr Leu
385                 390                 395                 400

Ile Ala Trp Arg Tyr Ala Gln Pro Lys Pro Ala Thr Ala Ala Val Pro
                405                 410                 415

Glu Pro Thr
```

<210> SEQ ID NO 15
<211> LENGTH: 1080
<212> TYPE: DNA
<213> ORGANISM: Variovorax paradoxus

<400> SEQUENCE: 15

```
atgatcctgg taaccggcgg cgcaggcttc attggcgcca atttcgtact cgactggctc      60

gcacagagcg atgaaccggt cgtgaaccta gacaagctga cctacgcggg caacctcgag     120

acgctcgcat cgctcaagga caacccgaag cacatcttcg tgcagggcga catcggcgac     180

agcgcgctgc tcgaccgcct gctggccgag cacaagccgc gtgccgtggt caacttcgcg     240

gccgaatcgc acgtcgaccg ctcgatccac ggccccgaag acttcgtgca gaccaacgtg     300

ctgggcacct tccgcctgct cgaatccgtg cgcggtttct ggaatgccct gccggccgac     360

cagaaggccg ccttccgctt cctgcatgtg tcgaccgacg aggtctacgg ctcgctctcc     420

aagaccgacc cggccttcac cgaagagaac aagtacgagc ccaacagccc gtactcggcc     480

agcaaggccg ccagcgacca cctcgtgcgc gcctggcacc acacctacgg cctgccggtg     540

gtcaccacca actgctcgaa caactacggg ccgttccact tccccgagaa gctcattccc     600

ctgatgatcg tcaacgcgct ggcgggcaag ccgctgcccg tgtacggcga cggcatgcag     660

gtgcgcgact ggctctacgt gaaggaccac tgcagcgcca tccgccgcgt gctcgaagcc     720

ggcaagctcg gcgagaccta caacgtgggc ggctggaacg agaagcccaa catcgagatc     780

gtcaacaccg tctgcgcgct gctcgacgag ctgagcccca aggccggcgg caagccgtac     840

aaggaacaga tcacctatgt gaccgaccgc cccggccacg accgccgcta cgcgatcgac     900

gcacgcaagc tcgagcgcga actcggctgg aaacctgccg agaccttcga cagcggcatc     960

cgcaagacgg tcgagtggta cctcgcgaac ggcgagtggg tgcgcaacgt gcaaagcggc    1020

gcgtaccgcg agtgggtcga gaagcaatac gacgccgcac cggcgaaggc caccgcatga    1080
```

<210> SEQ ID NO 16
<211> LENGTH: 359
<212> TYPE: PRT
<213> ORGANISM: Variovorax paradoxus

<400> SEQUENCE: 16

```
Met Ile Leu Val Thr Gly Gly Ala Gly Phe Ile Gly Ala Asn Phe Val
1               5                   10                  15

Leu Asp Trp Leu Ala Gln Ser Asp Glu Pro Val Val Asn Leu Asp Lys
            20                  25                  30

Leu Thr Tyr Ala Gly Asn Leu Glu Thr Leu Ala Ser Leu Lys Asp Asn
        35                  40                  45

Pro Lys His Ile Phe Val Gln Gly Asp Ile Gly Asp Ser Ala Leu Leu
    50                  55                  60

Asp Arg Leu Leu Ala Glu His Lys Pro Arg Ala Val Val Asn Phe Ala
65                  70                  75                  80

Ala Glu Ser His Val Asp Arg Ser Ile His Gly Pro Glu Asp Phe Val
                85                  90                  95

Gln Thr Asn Val Leu Gly Thr Phe Arg Leu Leu Glu Ser Val Arg Gly
            100                 105                 110

Phe Trp Asn Ala Leu Pro Ala Asp Gln Lys Ala Ala Phe Arg Phe Leu
        115                 120                 125

His Val Ser Thr Asp Glu Val Tyr Gly Ser Leu Ser Lys Thr Asp Pro
    130                 135                 140

Ala Phe Thr Glu Glu Asn Lys Tyr Glu Pro Asn Ser Pro Tyr Ser Ala
145                 150                 155                 160

Ser Lys Ala Ala Ser Asp His Leu Val Arg Ala Trp His His Thr Tyr
                165                 170                 175

Gly Leu Pro Val Val Thr Thr Asn Cys Ser Asn Asn Tyr Gly Pro Phe
            180                 185                 190

His Phe Pro Glu Lys Leu Ile Pro Leu Met Ile Val Asn Ala Leu Ala
        195                 200                 205

Gly Lys Pro Leu Pro Val Tyr Gly Asp Gly Met Gln Val Arg Asp Trp
    210                 215                 220

Leu Tyr Val Lys Asp His Cys Ser Ala Ile Arg Arg Val Leu Glu Ala
225                 230                 235                 240

Gly Lys Leu Gly Glu Thr Tyr Asn Val Gly Gly Trp Asn Glu Lys Pro
                245                 250                 255

Asn Ile Glu Ile Val Asn Thr Val Cys Ala Leu Leu Asp Glu Leu Ser
            260                 265                 270

Pro Lys Ala Gly Gly Lys Pro Tyr Lys Glu Gln Ile Thr Tyr Val Thr
        275                 280                 285

Asp Arg Pro Gly His Asp Arg Arg Tyr Ala Ile Asp Ala Arg Lys Leu
    290                 295                 300

Glu Arg Glu Leu Gly Trp Lys Pro Ala Glu Thr Phe Asp Ser Gly Ile
305                 310                 315                 320

Arg Lys Thr Val Glu Trp Tyr Leu Ala Asn Gly Glu Trp Val Arg Asn
                325                 330                 335

Val Gln Ser Gly Ala Tyr Arg Glu Trp Val Glu Lys Gln Tyr Asp Ala
            340                 345                 350

Ala Pro Ala Lys Ala Thr Ala
        355
```

<210> SEQ ID NO 17
<211> LENGTH: 891
<212> TYPE: DNA
<213> ORGANISM: Variovorax paradoxus

<400> SEQUENCE: 17

-continued

```
atgaagctgc tgctgctggg caagggcgga caggtcggct gggagctgca acgcagcctc      60

gcgcccctgg gcgaactggt ggcgctcgat ttcgacagca ccgacttcaa cgccgacttc     120

agtcgccccg agcagctggc cgagacagtg ctgaaggtgc gccccgacgt catcgtcaat     180

gccgcagcgc acaccgcggt cgacaaggcc gagagcgagc ccgagttcgc gcgcaagctc     240

aacgccacct cgcccggcgt ggtggccgaa gccgcgcagc agatcggcgc gctgatggtt     300

cactactcga ccgactacgt cttcgacggc agcggcagca agccgtggaa agaagacgat     360

gcgaccggcc cgctcagcgt ctacggcagc accaagctcg aaggcgagca actggtggca     420

aagcactgtg cgaagcacct gatctttcgc accagctggg tctatgccgc gcgcggcggc     480

aacttcgcca agaccatgct gcgcatcgcc aaggagcgcg acaagctgac cgtcatcgac     540

gaccagttcg gcgcgcccac cggcgcggaa ctgctggccg acatcaccgc gcacgcgatt     600

cgcgcgacgc tgcaggaccc gtccaaggcc gggctctatc acgcggtggc cggtggcgtg     660

accacgtggc acggctatgc gcgcttcgtg atcgagcagg ccaaggcggc gggcgtggaa     720

ctgaaggccg gccccgaagc ggtcgagccc gtgcccacca cggcattccc gacgccggcc     780

aggcggccgc acaactcgcg cctggacacc accaagctgc aatcgacctt cggcctcgtg     840

ctgcccgagt ggcagtccgg cgtcgcccgc atgttgcgcg aaaccttctg a              891
```

```
<210> SEQ ID NO 18
<211> LENGTH: 296
<212> TYPE: PRT
<213> ORGANISM: Variovorax paradoxus

<400> SEQUENCE: 18

Met Lys Leu Leu Leu Leu Gly Lys Gly Gly Gln Val Gly Trp Glu Leu
1               5                   10                  15

Gln Arg Ser Leu Ala Pro Leu Gly Glu Leu Val Ala Leu Asp Phe Asp
            20                  25                  30

Ser Thr Asp Phe Asn Ala Asp Phe Ser Arg Pro Glu Gln Leu Ala Glu
        35                  40                  45

Thr Val Leu Lys Val Arg Pro Asp Val Ile Val Asn Ala Ala Ala His
    50                  55                  60

Thr Ala Val Asp Lys Ala Glu Ser Glu Pro Glu Phe Ala Arg Lys Leu
65                  70                  75                  80

Asn Ala Thr Ser Pro Gly Val Val Ala Glu Ala Ala Gln Gln Ile Gly
                85                  90                  95

Ala Leu Met Val His Tyr Ser Thr Asp Tyr Val Phe Asp Gly Ser Gly
            100                 105                 110

Ser Lys Pro Trp Lys Glu Asp Asp Ala Thr Gly Pro Leu Ser Val Tyr
        115                 120                 125

Gly Ser Thr Lys Leu Glu Gly Glu Gln Leu Val Ala Lys His Cys Ala
    130                 135                 140

Lys His Leu Ile Phe Arg Thr Ser Trp Val Tyr Ala Ala Arg Gly Gly
145                 150                 155                 160

Asn Phe Ala Lys Thr Met Leu Arg Ile Ala Lys Glu Arg Asp Lys Leu
                165                 170                 175

Thr Val Ile Asp Asp Gln Phe Gly Ala Pro Thr Gly Ala Glu Leu Leu
            180                 185                 190

Ala Asp Ile Thr Ala His Ala Ile Arg Ala Thr Leu Gln Asp Pro Ser
        195                 200                 205

Lys Ala Gly Leu Tyr His Ala Val Ala Gly Gly Val Thr Thr Trp His
    210                 215                 220
```

```
Gly Tyr Ala Arg Phe Val Ile Glu Gln Ala Lys Ala Ala Gly Val Glu
225                 230                 235                 240

Leu Lys Ala Gly Pro Glu Ala Val Glu Pro Val Pro Thr Thr Ala Phe
                245                 250                 255

Pro Thr Pro Ala Arg Arg Pro His Asn Ser Arg Leu Asp Thr Thr Lys
            260                 265                 270

Leu Gln Ser Thr Phe Gly Leu Val Leu Pro Glu Trp Gln Ser Gly Val
        275                 280                 285

Ala Arg Met Leu Arg Glu Thr Phe
    290                 295
```

<210> SEQ ID NO 19
<211> LENGTH: 897
<212> TYPE: DNA
<213> ORGANISM: Variovorax paradoxus

<400> SEQUENCE: 19

```
atgaccaaga cgacgcaacg caaaggcatc atcctcgccg gtggctcggg cacccgcctg      60

caccccgcga cgcttgccat gagcaaacaa ctgctgccgg tgtacgacaa gccgatgatc     120

tattacccgc tgagcacgct gatgctgggc ggcatgcgcg acatcctgat catcagcacg     180

ccgcaggaca cgccgcgttt ccagcaactg ctgggggatg gcagccaatg ggcatcaac      240

ctgcagtacg cggtgcagcc gagcccggat ggtctggcgc aggcgttcat catcggtgac     300

aagttcgtgg gcaacgaccc gagtgcgctg gtgctggggg acaacatctt ctatggccac     360

gacttcgccc atctgctggc cgatgccgac gccaagacct cgggtgcgac ggtgttcgcc     420

taccacgtgc acgaccccga gcgctacggc gtggtggcct tcgatgccaa gggcagggcg     480

agcagcatcg aagaaaagcc gctcaagccc aagagcagct atgcggtcac gggcctctac     540

ttctacgaca accaggtcgt cgacatcgcc aaggccgtga agccgagcgc gcgcggcgaa     600

ctcgagatca ccgcggtcaa ccaggcgtat ctcgacctcg accagctgaa cgtgcagatc     660

atgcagcgcg gctatgcgtg gctcgatacc ggtacgcacg acagcctgct ggaagccggg     720

cagttcattg ccacgctcga gcaccgccag gggctgaaga tcgcatgccc cgaagagatc     780

gcatggcgca atggcttcat ctcaaccgag caactcgaaa agctcgcggc gccgctggaa     840

aagagcggct acggcaagta cctcaagcac ctgctgaacg acgaggtgcg ctcgtga        897
```

<210> SEQ ID NO 20
<211> LENGTH: 298
<212> TYPE: PRT
<213> ORGANISM: Variovorax paradoxus

<400> SEQUENCE: 20

```
Met Thr Lys Thr Thr Gln Arg Lys Gly Ile Ile Leu Ala Gly Gly Ser
1               5                   10                  15

Gly Thr Arg Leu His Pro Ala Thr Leu Ala Met Ser Lys Gln Leu Leu
            20                  25                  30

Pro Val Tyr Asp Lys Pro Met Ile Tyr Tyr Pro Leu Ser Thr Leu Met
        35                  40                  45

Leu Gly Gly Met Arg Asp Ile Leu Ile Ile Ser Thr Pro Gln Asp Thr
    50                  55                  60

Pro Arg Phe Gln Gln Leu Leu Gly Asp Gly Ser Gln Trp Gly Ile Asn
65                  70                  75                  80

Leu Gln Tyr Ala Val Gln Pro Ser Pro Asp Gly Leu Ala Gln Ala Phe
                85                  90                  95
```

-continued

```
Ile Ile Gly Asp Lys Phe Val Gly Asn Asp Pro Ser Ala Leu Val Leu
            100                 105                 110

Gly Asp Asn Ile Phe Tyr Gly His Asp Phe Ala His Leu Leu Ala Asp
        115                 120                 125

Ala Asp Ala Lys Thr Ser Gly Ala Thr Val Phe Ala Tyr His Val His
    130                 135                 140

Asp Pro Glu Arg Tyr Gly Val Val Ala Phe Asp Ala Lys Gly Arg Ala
145                 150                 155                 160

Ser Ser Ile Glu Glu Lys Pro Leu Lys Pro Lys Ser Ser Tyr Ala Val
                165                 170                 175

Thr Gly Leu Tyr Phe Tyr Asp Asn Gln Val Val Asp Ile Ala Lys Ala
            180                 185                 190

Val Lys Pro Ser Ala Arg Gly Glu Leu Glu Ile Thr Ala Val Asn Gln
        195                 200                 205

Ala Tyr Leu Asp Leu Asp Gln Leu Asn Val Gln Ile Met Gln Arg Gly
    210                 215                 220

Tyr Ala Trp Leu Asp Thr Gly Thr His Asp Ser Leu Leu Glu Ala Gly
225                 230                 235                 240

Gln Phe Ile Ala Thr Leu Glu His Arg Gln Gly Leu Lys Ile Ala Cys
                245                 250                 255

Pro Glu Glu Ile Ala Trp Arg Asn Gly Phe Ile Ser Thr Glu Gln Leu
            260                 265                 270

Glu Lys Leu Ala Ala Pro Leu Glu Lys Ser Gly Tyr Gly Lys Tyr Leu
        275                 280                 285

Lys His Leu Leu Asn Asp Glu Val Arg Ser
    290                 295
```

<210> SEQ ID NO 21
<211> LENGTH: 546
<212> TYPE: DNA
<213> ORGANISM: Variovorax paradoxus

<400> SEQUENCE: 21

```
gtgaaggcca cgcccacctc gattcctgac gtgctcgtga tcgagccgaa ggtgtttggc      60

gatgcacggg gcttcttctt cgaaagcttc aaccagaagg ccttcgacga agcgatcggc     120

aagcatgtcg acttcgtgca ggacaaccat tcgcgatcgg ccaagggtgt gctgcggggg     180

ctgcattacc aggtccagca gccgcaaggc aagctcgtgc gggtggtgcg tggtgcggtg     240

ttcgacgtgg ccgtcgacat ccgcaagtcg tcgccgactt ttggcaaatg ggtgggtgtc     300

gagttgaacg aagacaacca caagcagctc tgggtgccgg caggattcgc gcacggtttc     360

ctggtgttga gcgagaccgc ggaattcctc tacaagacca ccgactacta cgcgcccgcc     420

cacgagcgcg cgattgtctg gaacgacccc gctgtcggta ttcgatggcc ggatgtggga     480

ggggcaccgg tcctgtcgaa gaaggacgaa gacgggtgtc ttctgcaagc ggcagaggtt     540

ttctag                                                                546
```

<210> SEQ ID NO 22
<211> LENGTH: 181
<212> TYPE: PRT
<213> ORGANISM: Variovorax paradoxus

<400> SEQUENCE: 22

```
Met Lys Ala Thr Pro Thr Ser Ile Pro Asp Val Leu Val Ile Glu Pro
1               5                   10                  15
```

-continued

```
Lys Val Phe Gly Asp Ala Arg Gly Phe Phe Phe Glu Ser Phe Asn Gln
            20                  25                  30

Lys Ala Phe Asp Glu Ala Ile Gly Lys His Val Asp Phe Val Gln Asp
        35                  40                  45

Asn His Ser Arg Ser Ala Lys Gly Val Leu Arg Gly Leu His Tyr Gln
    50                  55                  60

Val Gln Gln Pro Gln Gly Lys Leu Val Arg Val Val Arg Gly Ala Val
65                  70                  75                  80

Phe Asp Val Ala Val Asp Ile Arg Lys Ser Ser Pro Thr Phe Gly Lys
                85                  90                  95

Trp Val Gly Val Glu Leu Asn Glu Asp Asn His Lys Gln Leu Trp Val
            100                 105                 110

Pro Ala Gly Phe Ala His Gly Phe Leu Val Leu Ser Glu Thr Ala Glu
        115                 120                 125

Phe Leu Tyr Lys Thr Thr Asp Tyr Tyr Ala Pro Ala His Glu Arg Ala
    130                 135                 140

Ile Val Trp Asn Asp Pro Ala Val Gly Ile Arg Trp Pro Asp Val Gly
145                 150                 155                 160

Gly Ala Pro Val Leu Ser Lys Lys Asp Glu Asp Gly Cys Leu Leu Gln
                165                 170                 175

Ala Ala Glu Val Phe
            180
```

<210> SEQ ID NO 23
<211> LENGTH: 1029
<212> TYPE: DNA
<213> ORGANISM: Variovorax paradoxus

<400> SEQUENCE: 23

```
atgggcagca gccatcatca tcatcatcac agcagcggcc tggtgccgcg cggcagccat      60

atgtccttcc cgttcggtgc cgtcgtcgtc acctatttcc cgaccggcga gcaagtggcg     120

aacctccatt cgctggcggc ctcgtgtccg cacctctgcg tggtcgacaa cacgccgcag     180

gtgggcgatt ggcatgcggc gctcgtcgat gcgggcgttt cggtgctgca caacggcaac     240

cgcggcggca tcgcgggcgc cttcaaccgc ggcatcatcg acctcgaagc gcggggcgcc     300

gaactcttct tcctgctcga ccaggattcg aagctgccac ccggctactt cgatgccatg     360

tgcgaggctg cgatggtggc ccgggagcgg aagggcgagg gcaatggtga ggaagacgcg     420

gccttcctga tcggcccgct cgtccacgac acgaacctgg acgcgctgat cccgcaattc     480

ggcctccagg gcaaacgcgt ctaccagttc gacctgcggc agcccttcac cgagccgctg     540

atgcgctgcg ccttcatgat ttcctcgggc tccctgattt cgcgcggcgc ctgggcccgg     600

atcggccggt tcgacgagcg ctatgtgatc gaccacgtgg acaccgacta ctgcatgcgt     660

gccctgggtc gcggcgtgcc gctctacctg aatccgcacg tcgtgctgcg gcaccagatt     720

ggcgacatcc gtgcccggtc gctgttcggc tggaagatcc acttcatcaa ctacccggcc     780

gcgcggcgct actacatcgc gcgcaatgcc atcgatctct cgcgggcgca tgtgcgcgcc     840

tttcccgcga tcctgttcat caacgtttac acgctcaagc agatcctgcc gatgctgatg     900

ttcgagcgcg accgcttcaa gaagaccatc gcgctgatgc tcggctgctt cgatggcctg     960

ttcgggcggc tcgggggcct cggcgaggtg catccgcgga tgggcaaata cctgggccgc    1020

agcgattga                                                            1029
```

<210> SEQ ID NO 24

-continued

```
<211> LENGTH: 342
<212> TYPE: PRT
<213> ORGANISM: Variovorax paradoxus

<400> SEQUENCE: 24

Met Gly Ser Ser His His His His His His Ser Ser Gly Leu Val Pro
1               5                   10                  15

Arg Gly Ser His Met Ser Phe Pro Phe Gly Ala Val Val Val Thr Tyr
            20                  25                  30

Phe Pro Thr Gly Glu Gln Val Ala Asn Leu His Ser Leu Ala Ala Ser
        35                  40                  45

Cys Pro His Leu Cys Val Val Asp Asn Thr Pro Gln Val Gly Asp Trp
    50                  55                  60

His Ala Ala Leu Val Asp Ala Gly Val Ser Val Leu His Asn Gly Asn
65                  70                  75                  80

Arg Gly Gly Ile Ala Gly Ala Phe Asn Arg Gly Ile Ile Asp Leu Glu
                85                  90                  95

Ala Arg Gly Ala Glu Leu Phe Phe Leu Leu Asp Gln Asp Ser Lys Leu
            100                 105                 110

Pro Pro Gly Tyr Phe Asp Ala Met Cys Glu Ala Ala Met Val Ala Arg
        115                 120                 125

Glu Arg Lys Gly Glu Gly Asn Gly Glu Glu Asp Ala Ala Phe Leu Ile
    130                 135                 140

Gly Pro Leu Val His Asp Thr Asn Leu Asp Ala Leu Ile Pro Gln Phe
145                 150                 155                 160

Gly Leu Gln Gly Lys Arg Val Tyr Gln Phe Asp Leu Arg Gln Pro Phe
                165                 170                 175

Thr Glu Pro Leu Met Arg Cys Ala Phe Met Ile Ser Ser Gly Ser Leu
            180                 185                 190

Ile Ser Arg Gly Ala Trp Ala Arg Ile Gly Arg Phe Asp Glu Arg Tyr
        195                 200                 205

Val Ile Asp His Val Asp Thr Asp Tyr Cys Met Arg Ala Leu Gly Arg
    210                 215                 220

Gly Val Pro Leu Tyr Leu Asn Pro His Val Val Leu Arg His Gln Ile
225                 230                 235                 240

Gly Asp Ile Arg Ala Arg Ser Leu Phe Gly Trp Lys Ile His Phe Ile
                245                 250                 255

Asn Tyr Pro Ala Ala Arg Arg Tyr Tyr Ile Ala Arg Asn Ala Ile Asp
            260                 265                 270

Leu Ser Arg Ala His Val Arg Ala Phe Pro Ala Ile Leu Phe Ile Asn
        275                 280                 285

Val Tyr Thr Leu Lys Gln Ile Leu Pro Met Leu Met Phe Glu Arg Asp
    290                 295                 300

Arg Phe Lys Lys Thr Ile Ala Leu Met Leu Gly Cys Phe Asp Gly Leu
305                 310                 315                 320

Phe Gly Arg Leu Gly Gly Leu Gly Glu Val His Pro Arg Met Gly Lys
                325                 330                 335

Tyr Leu Gly Arg Ser Asp
            340
```